US011433051B2

(12) United States Patent
Tyavanagimatt et al.

(10) Patent No.: US 11,433,051 B2
(45) Date of Patent: Sep. 6, 2022

(54) ST-246 (TECOVIRIMAT MONOHYDRATE) SUSPENSION FORMULATIONS

(71) Applicant: SIGA TECHNOLOGIES, INC., Corvallis, OR (US)

(72) Inventors: Shanthakumar R. Tyavanagimatt, Sammamish, WA (US); Kris Holt, Colorado Springs, CO (US); Ying Tan, Millbrae, CA (US); Melialani A. C. L. S. Anderson, Corvallis, OR (US); Dennis E. Hruby, Albany, OR (US)

(73) Assignee: Siga Technologies, Inc., Corvallis, OR (US)

( * ) Notice: Subject to any disclaimer, the term of this patent is extended or adjusted under 35 U.S.C. 154(b) by 1015 days.

(21) Appl. No.: 16/071,119

(22) PCT Filed: Feb. 15, 2017

(86) PCT No.: PCT/US2017/017915
§ 371 (c)(1),
(2) Date: Jul. 19, 2018

(87) PCT Pub. No.: WO2017/142910
PCT Pub. Date: Aug. 24, 2017

(65) Prior Publication Data
US 2021/0212987 A1 Jul. 15, 2021

Related U.S. Application Data

(60) Provisional application No. 62/295,710, filed on Feb. 16, 2016.

(51) Int. Cl.
*A61K 31/403* (2006.01)
*A61K 9/00* (2006.01)
(Continued)

(52) U.S. Cl.
CPC .......... *A61K 31/403* (2013.01); *A61K 9/0053* (2013.01); *A61K 9/0095* (2013.01);
(Continued)

(58) Field of Classification Search
None
See application file for complete search history.

(56) References Cited

U.S. PATENT DOCUMENTS 3,043,747 A   7/1962  Long
4,863,737 A * 9/1989  Stanley .................. A23G 3/368
                                                        424/440
(Continued)

FOREIGN PATENT DOCUMENTS

CN         102406617 A        7/1962
CN         101 011 360 A      8/2007
(Continued)

OTHER PUBLICATIONS

Brecevic et al. (Mechanism of antifoaming action of simethicone, Journal of Applied Toxicology, vol. 14, Issue 3, p. 207-211; May/Jun. 1994) (Year: 1994).*
(Continued)

*Primary Examiner* — Melissa S Mercier
(74) *Attorney, Agent, or Firm* — Charles C. Achkar; Ostrolenk Faber LLP

(57) ABSTRACT

The present invention is directed to a dry suspension for reconstitution containing Tecovirimat (ST-246) powder and simethicone. The dry suspension is dispersed in water to provide an aqueous pharmaceutical suspension formulation for oral administration for treating orthopoxvirus infections and/or eczema vaccinatum. The suspension formulation exhibits excellent stability and good dissolution and has an improved taste and texture.

19 Claims, 9 Drawing Sheets

Figure 1:
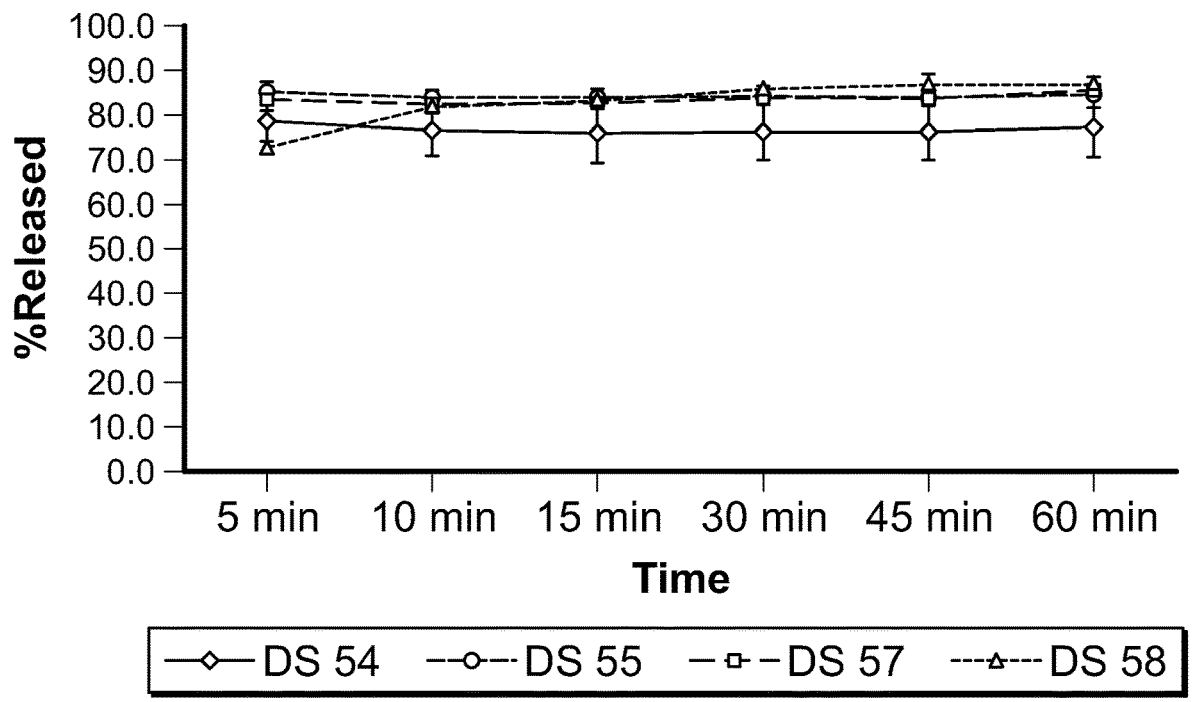

ST-246 Release from DS 54, 55, 57 and 58

(51) Int. Cl.
A61K 9/16 (2006.01)
A61K 47/26 (2006.01)
A61K 47/34 (2017.01)
A61K 47/38 (2006.01)

(52) U.S. Cl.
CPC ............... *A61K 9/16* (2013.01); *A61K 47/26* (2013.01); *A61K 47/34* (2013.01); *A61K 47/38* (2013.01)

(56) References Cited

U.S. PATENT DOCUMENTS 5,093,372 A   3/1992  Uedo et al.
5,458,886 A * 10/1995 Briquet ................. A61K 31/80
                                                          424/451

FOREIGN PATENT DOCUMENTS

| CN | 100571683 C    | 12/2009 |
| CN | 102406617 A *  | 4/2012  |
| CN | 102532901 A    | 4/2012  |
| CN | 105055326 A    | 11/2015 |
| WO | WO 2011/119698 | 9/2011  |

OTHER PUBLICATIONS

Hamel et al. Formulations of Test Articles, Genetic Toxicology Testing, 2016). (Year: 2016).*
International Search Report issued in International Application No. PCT/US17/17915, dated Apr. 28, 2017.
Written Opinion of the International Searching Authority issued in International Application No. PCT/US17/17915, dated Apr. 28, 2017.
Chinese Office Acton issued in counterpart CN application No. 2017800052455 dated Jan. 27, 2021.
Shuguang Lei et al.. Chin J Pharm Anal, vol. 32, No. 2, pp. 296-300, publication date: Feb. 29, 2012. English language abstract included.
Japanese Office Acton issued in counterpart JP application No. 2018-542140 dated Dec. 14, 2020.
International Preliminary Report issued in PCT/US2017/017915, dated Aug. 21, 2018.
Extended EP Search Report issued in counterpart EP applicaton No. 17753732.1 dated Oct. 8, 2019.
G. Yang et al: "An Orally Bioavailable Antipoxvirus Compound (ST-246) Inhibits Extracellular Virus Formation and Protects Mice from Lethal Orthopoxvirus Challenge", Journal of Virology, vol. 79, No. 20, Oct. 15, 2005 (Oct. 15, 2005), pp. 13139-13149, XP055156407 ISSN: 0022-538X, DOI: 10.112 8/JVI.79.20.13139-13149.2005.
"Simethicone or Dimethicone—What's the difference", WikiDiff, pp. 1-1, Retrieved from the Internet:URL:https://wikidiff.com/dimethicone/simethicone, [retrieved on Sep. 6, 2019].
Chinese Officce Acton issued in counterpart CN application No. 2017800052455 dated Jun. 2, 2020.
The International Pharmaceutical Excipients Council of the Americas, Inactive Ingredient Database Issues with ANDAs, Backgrounder Document Dec. 9, 2011.
*Handbook of Pharmaceutical Excipients—Fifth Edition* (2006), edited by Raymond C. Rowe, Paul J. Sheskey, and Siân C. Owen (published by the Pharmaceutical Press, Publications division of the Royal Pharmaceutical Society of Great Britain.
PubChem CID 6433516. https://pubchem.ncbi.nlm.hih.gov/compound/simethicone.
SIGA-2792—compound structures.
Dimethicone drug-drug interactions. Mdg.usg/ovxml.com/drugInt.aspx?name . . . Jun. 10, 2021.
Segesterone acetate. Wikipedia.
Albemarle® Certificates of Analysis (CoAs).
Simethicone Drug Interactions—Drugs.com, downloaded Jun. 10, 2021.
Chinese Office Action issued in counterpart CN application No. 201780005245.5 dated Jul. 28, 2021 with English language summary thereof.
SPECTRUM® Chemical MGF Corp. Specification for Simethicne. USP (S1926)
VWR™ port of avantar, Siimethicone USP.
Disclosure of Confidential Information Under Albemarle/Siga Mutual Confidential Disclosure Agreement, Jaap Louwen report, ST-246 Crystal Structure Claimed in Patent CN101445478A. Feb. 12, 2010.
Japanese Office Action issued in counterpart JP application No. 2018-542140 dated Sep. 13, 2021, with English language summary thereof.
Israeli Office Action issued in counterpart IL application No. 260229 dated Oct. 19, 2021, with English language summary thereof.
AU Office Action issued in counterpart AU application No. 2017221295 dated Sep. 13, 2021.
Israeli Office Acton issued in counterpart IL application No. 260229 dated Sep. 1, 2020.
"Handbook of Pharmaceutical Excipients"; Fifth Ed. Edited by Raymond C Rowe et al., ISBN 978-0-85369-618-6, pp. 336-340, 430-433, 462-465, 652-653.
European Communication pursuant to Article 94(3) issued in counterpart EP Application No. 17 753 732.1, dated Feb. 18, 2021.

* cited by examiner

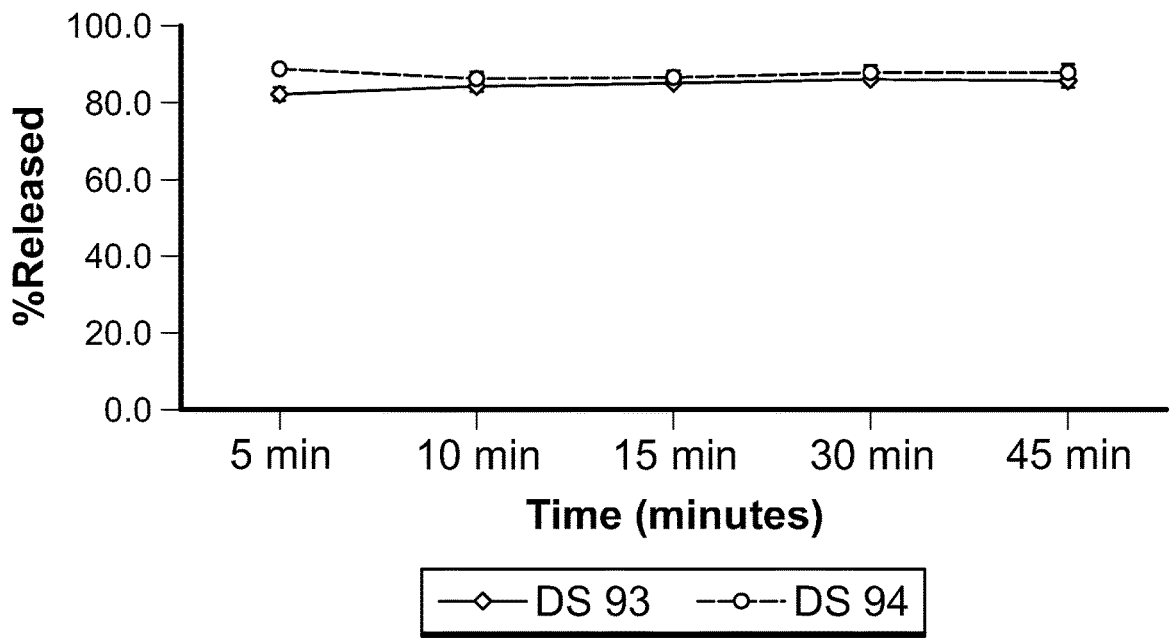

FIG. 10

| Flavor Profile Definitions |
|---|
| Amplitude: Initial overall perception of the balance and fullness of a flavored product; considering the appropriateness of aromas and flavor notes present, their blend and intensity and existence of off-notes. |
| Amplitude Scale: 0 — ½ — 1 — 1½ — 2 — 2½ — 3 / None    Low    Moderate    High |
| Character Notes: Aromatics, basic tastes, and feeling factors (listed in order of appearance along with a measurement of strength). |
| Intensity Scale: 0 — ½ — 1 — 1½ — 2 — 2½ — 3 / None    Slight    Moderate    Strong |
| Aftertaste: Measurement of all sensation remaining at selected time intervals |

FIG. 11

ST-246 (TECOVIRIMAT MONOHYDRATE) SUSPENSION FORMULATIONS

CROSS REFERENCE TO RELATED APPLICATIONS

The present application is a § 371 National Phase application based on PCT/US2017/017915 filed Feb. 15, 2015 which claims the benefit of U.S. provisional application No. 62/295,710 filed Feb. 16, 2016 the subject matter of each of which is incorporated by reference in their entirety.

STATEMENT REGARDING FEDERALLY SPONSORED RESEARCH OR DEVELOPMENT

This invention was made with U.S. government support under Contract No.: HHSO100201100001C awarded by the Biomedical Advanced Research and Development Authority (BARDA). The U.S. government has certain rights in this invention.

FIELD OF THE INVENTION

The present invention relates to a novel oral powder for suspension (dry suspension) containing Tecovirimat (ST-246) powder for reconstitution and a process for making the dry suspension. The dry suspensions are dispersed in water to provide aqueous pharmaceutical suspension formulations for oral administration.

BACKGROUND OF THE INVENTION

Throughout this application, various publications are referenced within the text. The disclosure of these publications in their entireties are hereby incorporated by reference into this application in order to more fully describe the state of the art as known to those skilled in therein as of the date of the invention described and claimed herein.

Historically, variola virus, the etiologic agent of smallpox, has been estimated to have killed, crippled, or disfigured nearly 10% of the human population prior to eradication (1). Smallpox is highly communicable and carries exceptionally high morbidity. Secondary attack rates among unvaccinated members of households in which someone had smallpox have been reported to range from r30% to 80%. Mortality rates range from 1% for variola minor to 30% for variola major. With the advent of biowarfare as an instrument of terrorism, smallpox can no longer be thought of as a disease of historic impact only.

There are currently no therapies other than early vaccination that can alter the outcome of disease or potentially prevent disease in a population that has been exposed to smallpox. Vaccination carries an inherent risk of adverse events for certain immunosuppressed recipients and even some healthy recipients (2). Moreover, vaccination is effective only if administered within 4 days post-exposure. Thus, antiviral drugs used alone or potentially in combination with vaccination can be used to treat individuals during the window of vulnerability which occurs prior to development of protective immunity. Additionally, antiviral drugs could also be used in the treatment of zoonotic poxvirus disease in humans, such as monkeypox.

ST-246 (4-trifluoromethyl-N-(3,3a,4,4a,5,5a,6,6a-octahydro-1,3-dioxo-4,6-ethenocycloprop[f]isoindol-2(1H)-yl)-benzamide)(Tecovirmat), has recently emerged as a potent candidate against orthopoxvirus. Several studies evaluating ST-246 for activity against orthopoxviruses have demonstrated excellent in vitro and in vivo efficacy (3, 4). When evaluated in vitro against vaccinia virus (VV), cowpox virus (CV), ectromelia virus (ECTV), monkeypox, camelpox, and variola viruses, ST-246 inhibited virus replication by 50% (50% effective concentration [EC50]) at or below a concentration of 0.07 µM. With animal models using lethal infections with ECTV, VV, or CV, ST-246 was reported to be nontoxic and highly effective in preventing or reducing mortality even when treatments were delayed up to 72 h post-viral inoculation (3, 4). ST-246 was also evaluated with the nonlethal mouse tail lesion model using intravenous VV. When ST-246 was administered orally twice a day at 15 or 50 mg/kg of body weight for 5 days, the tail lesions were significantly reduced (4). Most recently, an infant was given ST-246 as an FDA-authorized emergency treatment for eczema vaccinatum which developed after exposure to the parent's predeployment military smallpox immunization (5).

Given the high efficacy of ST-246 antiviral therapy against smallpox and a lack of FDA-approved medications for the treatment of smallpox infection, there is clearly a need for developing safe and effective ST-246 formulations that can be administered by various routes of administration. However, the poor solubility of ST-246 in water and in pharmaceutically acceptable pH buffers and commonly used pharmaceutical vehicles such as co-solvents, surfactants, complexing agents, and lipids creates an impediment to making safe and effective ST-246 liquid formulations.

Thus, there is a critical need in the pharmaceutical and other biological based industries to formulate water insoluble ST-246 into liquid suspensions for oral, parenteral, or topical administration.

However, the preparation of an aqueous pharmaceutical suspension formulation from micronized ST-246 presents problems that are difficult to overcome, such as retaining the colloidal stability, preventing particle size growth and foaming.

Furthermore, once an aqueous suspension has been prepared, sedimentation of the suspension should be avoided. However, if sedimentation arises, the restoration of the suspension must be achieved as easily and as quickly as possible and advantageously this should be achieved by simply shaking the mixture by hand.

Failure to attain rapid reconstitution of the suspension results in an unacceptably high risk of a dosage error. Furthermore, rapid reconstitution is crucial given that the suspension is often dispensed using a dropper or a dispensing syringe, thereby requiring a stable liquid suspension which is able to flow freely from the dispensing devices and ensure that significantly less material sticks therein.

Additionally, foaming of the suspension formulation should be avoided, given that this also results in the dosage being imprecise and uncertain.

Finally, suspension formulations that are used for oral administration, particularly for pediatric use, must not have a bitter taste.

SUMMARY OF THE INVENTION

The present invention provides an oral powder for suspension (dry suspension) containing 4-trifluoromethyl-N-(3,3a,4,4a,5,5a,6,6a-octahydro-1,3-dioxo-4,6-ethenocycloprop[f]isoindol-2-(1H)-yl)-benzamide, commonly known as Tecovirimat or ST-246, granulated powder and simethicone, which is suitable for reconstitution.

The present invention also provides a process for making the dry suspension comprising mixing ST-246 powder with simethicone.

The present invention further provides an aqueous pharmaceutical suspension formulation comprising ST-246, simethicone and a suspending agent for oral administration.

Additionally, the present invention provides a process for making the aqueous pharmaceutical suspension formulation comprising dispersing the dry suspension and a suspending agent in water.

The present invention also provides methods of treating orthopoxvirus infections and/or eczema vaccinatum comprising administering to a subject in need thereof an aqueous pharmaceutical suspension formulation according to the present invention.

These and other objects, advantages, and features of the invention will become apparent to those persons skilled in the art upon reading the details of the methods and formulations as more fully described below.

DESCRIPTION OF THE DRAWINGS

FIG. 1 shows the % ST-246 release from formulations DS 54, 55, 57 and 58.

FIG. 2 shows the % ST-246 release from formulations DS 75, 77, 83 and 84.

FIG. 3 shows the dissolution of ST-246 from formulations DS 85, 86, and 87.

FIG. 4 shows the % ST-246 release from formulation DS 88 at different blending times.

FIG. 5 shows the % ST-246 release from DS 88 at different lubrication times.

FIG. 6 shows the % ST-246 release from DS 89 and 90.

FIG. 7 shows the % ST-246 release from DS 91 and 92.

FIG. 8 shows an observation when passing simethicone or co-milled simethicone-Tecovirimat granules through #20 screen. A and B: no-dilution simethicone stuck on screen. C and D: pre-diluted and co-milled simethicone-Tecovirimat granules passed screen easily without sticking.

FIG. 9 shows retained clumps on #20 screen after sieve shaking of 100 g DS-92.

FIG. 10 shows % ST-246 release from DS 93 and 94.

FIG. 11 shows flavor profile definitions, including amplitude, amplitude scale, character notes, intensity scale and aftertaste.

FIG. 12 shows a time intensity profile of musty aromatic off-notes, bitterness and tannin mouthfeel of the Tecovirimat granules lingered at patient-perceptible levels (>1) for about 3 minutes in the aftertaste.

FIG. 13 shows a time intensity profile of Tecovirimat formulation #4 (micronized API).

FIG. 14 shows a time intensity profile of formulation #1 (strawberry)

FIG. 15 shows a time intensity profile of formulation #2(cherry)

DETAILED DESCRIPTION OF THE INVENTION

Tecovirimat (ST-246) is an antiviral agent used for smallpox and related orthopoxviruses. A suitable oral formulation, according to the present invention, is particularly useful in pediatric and/or geriatric populations. The typical maximum dosage is 1200 mg/day. The drug has very low water solubility over the physiologically relevant pH range, namely approximately 2 μg/mL over a pH range of 1.2 to 6.5. Its solubility increases slightly above pH 6.5, however the chemical stability declines. The solution stability is optimum in the pH 4 to 7 range, for example the pH 3 to 5 range.

Due to low solubility, preferably the ST-246 is micronized in order to improve dissolution rate. ST-246 has the potential to undergo supersaturation and crystallization with increased particle size in an aqueous based vehicle, and hence, providing an acceptable ready-to-use liquid/suspension dosage form with better stability and longer shelf-life represents a major challenge.

Additionally, when forming a suspension formulation containing ST-246, a wetting agent, such as a surfactant, is typically used to improve wetting of ST-246 particles, and also to improve dissolution and solubility. However, the presence of a surfactant usually leads to foaming and results in the formulation tasting bitter and having an unpleasant odor.

The present invention provides a powder for a reconstitution product (dry suspension) comprising ST-246 granulated powder and simethicone which when suspended in water exhibits acceptable stability and dissolution. Furthermore it has been found that the use of semithicone with ST-246 provides excellent foam control upon reconstitution.

The present invention provides a similar drug release profile, a critical product attribute for product performance in patients, as compared to capsule oral dosage form of ST-246.

Additionally, the incorporation of additional excipients, flavorings and/or sweeteners to the dry suspension and/or the aqueous pharmaceutical suspension formulation improves the taste and texture of the formulation.

The dry suspension and/or the suspension formulation may also include one or more pharmaceutically acceptable ingredients selected from the group consisting of disintegrants, carriers, diluents, additives, fillers, lubricants, and binders.

Disintegrants may include agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Preferably, the dry suspension further comprises at least one suspending agent.

The suspending agents may include sorbitol syrup; sugar syrup; synthetic polymers such as carbomer and poloxamer; natural gums such as agar, xanthan gum, and tragacanth; cellulose derivatives (e.g., carboxy methyl cellulose, hydroxyl propyl cellulose or methylcellulose); or hydrogenated edible fats; emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid).

The dry suspensions can also contain buffer salts, flavoring, coloring and sweetening agents as appropriate.

Furthermore, the dry suspensions may also contain wetting agents and/or surface active agents as appropriate.

Preferably, the wetting agent or surface active agent is sodium dodecyl sulfate, sodium docusate, tweens, spans, brij, or cetrimide.

Preferably, the suspending agent is methylcellulose and/or hydroxypropyl cellulose, and, advantageously, the dry suspension contains both methylcellulose and hydroxypropyl cellulose.

Preferably, the dry suspension contains methylcellulose 400 cps and/or methycellulose 15 cps and, advantageously, the dry suspension contains both methylcellulose 400 cps and methycellulose 15 cps methylcellulose.

Typically, the dry suspension comprises a lubricant, such as calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof.

Advantageously, the lubricant is magnesium stearate.

Excipients include, but are not limited to, agents used to improve taste, suspendability, texture, and flavor. In one embodiment, when the dry suspension contains an excipient, the excipient is advantageously lactose monohydrate. When present, the total amount of excipients are typically present in an amount of about 10 wt % to about 20 wt %.

The dry suspension may also contain a further antifoaming agent.

Preferably, the dry suspension also contains a sweetener, such as sucralose.

Advantageously, the dry suspension contains a flavoring such as strawberry or black cherry.

The ST-246 may be selected from the group consisting of ST-246 polymorph Form I, ST-246 polymorph Form II, ST-246 polymorph Form III, ST-246 polymorph Form IV, ST-246 polymorph Form V and ST-246 polymorph Form VI.

The ST-246 may be micronized and/or granulated with excipients, but is advantageously micronized and granulated powder.

Furthermore the simethicone may be in granular form or may be in liquid form and adsorbed on lactose monohydrate. Advantageously, the simethicone is in granular form.

The dry suspension typically contains between 10 to 70 wt % of ST-246, and preferably between 15 to 40 wt % of ST-246.

The dry suspension usually contains between 0.2 to 6.0 wt % simethicone, and preferably between 0.4 to 5.0 wt % simethicone.

Preferably, the dry suspension contains between 1 to 5 wt % of methylcellulose, and advantageously, between 2 to 3 wt % of methylcellulose.

Preferably, the dry suspension contains between 1.0 to 30 wt % of hydroxypropylcellulose, and, advantageously, between 2 to 20 wt % of hydroxypropylcellulose.

When the dry suspension contains a lubricant, typically the lubricant is present in the amount 0.1 to 1.0 wt %.

Similarly, when the dry suspension contains a sweetener, typically the sweetener is present in the amount of between 1.0 to 3.0 wt %, and when the dry suspension contains a flavoring, typically the flavoring is also present in the amount of between 0.1 to 1.0 wt %.

The dry suspension preferably has an active pharmaceutical ingredient (API) particle size of ST-246 of between 0.5 to 20 μm, or between 0.5 to 10 m, or between 1 m and 5 m, and, advantageously, between 1 to 10 μm.

It has been found that the higher the API particle size, the slower the dissolution rate.

The present invention also provides an aqueous pharmaceutical suspension formulation comprising the dry suspension dispersed in water.

Typically the suspension, either dry or liquid, contains a suspending agent which is preferably selected from the group consisting of hydromellose, hydroxyethylcellulose, carrageenans, methylcellulose, xanthan gum, povidone, hydroxypropyl cellulose, microcrystalline cellulose, carboxymethylcellulose and sodium alginate.

When the suspension contains water and a suspending agent this is typically referred to as a ‘formulation vehicle’.

Typically, the formulation, upon reconstitution with water, has a pH between 3 and 8, preferably between 5 and 7.

The present invention also provides a method of treating orthopoxvirus infections and/or eczema vaccinatum comprising oral administration to a subject in need thereof the above mentioned formulation. Typically, the formulation of the present invention is administered in an amount such that the dose of ST-246 is 200 mg to 2000 mg per day, preferably 400 mg to 2000 mg per day, and most preferably 600 mg to 1200 mg daily. Dosage is typically adjusted according to body weight, particularly in pediatric populations.

Additionally, the present invention also provides a process of making the dry suspension which involves mixing ST-246 or ST-246 granulated powder with simethicone.

Optionally, at least one suspending agent, at least one lubricant, at least one excipient, at least one further antifoaming agent, at least one sweetener and/or at least one flavoring may be mixed with the ST-246 and the simethicone.

Advantageously, mixing is carried out using geometric mixing.

Finally, the present invention provides a method of making the above mentioned formulation wherein the dry suspension is dispersed in water, and wherein the water advantageously contains a suspending agent as herein described above.

As used herein, “percent,” “percentage” or the symbol “%” means the percent of the component indicated in the composition based on the amount of the carrier present in the composition, on a weight/weight (w/w), weight/volume (w/v) or volume/volume (v/v) concentration, as indicated with respect to any particular component, all based on the amount of the carrier present in the composition. Thus, different types of carriers can be present in an amount of up to 100% as indicated, which does not preclude the presence of the API, the amount of which can be indicated as a % or as a certain number of mg present in the composition or a certain number of mg/mL present, where the % or mg/mL is based on the amount of the total carrier present in the composition. Certain types of carriers can be present in combination to makeup 100% of the carrier.

As used herein, the terms “Tecovirimat” and “ST-246” refer to the compound 4-trifluoromethyl-N-(3,3a,4,4a,5,5a,6,6a-octahydro-1,3-dioxo-4,6-ethenocycloprop[f]isoindol-2-(1H)-yl)-benzamide.

The invention is further described by the examples given below.

EXAMPLES

Example 1. Production of a Dry Suspension Containing Tecrovirimat Monohydrate (ST-246) for Reconstitution, 200 Mg A stable oral powder containing ST-246 was prepared, particularly for pediatric and/or geriatric application. The development of the powder involved the following stages;

1. Formulation and evaluation of various dry suspensions.
2. Optimization and evaluation of various levels of antifoaming agents and lubricant and their effect on product properties.
3. Optimization and evaluation of blending time and lubrication time in the product manufacturing process and its effect on product properties.

4. Manufacture of batches for stability studies.
Materials: The following materials were used.

| S. # | Material | Supplier/Lot# |
|---|---|---|
| 1 | Tecovirimat Monohydrate, micronized, for discriminatory dissolution method development | Siga Technologies Lot # SG-10C12-T1039 (Trial #2, d90 = 21.51 μm) |
| 2 | Tecovirimat Monohydrate, micronized, for discriminatory dissolution method development | Siga Technologies Lot # SG-10C12-T1039 (Trial #3, d90 = 38.74 μm) |
| 3 | Tecovirimat Monohydrate, micronized, for discriminatory dissolution method development | Siga Technologies Lot # SG-10C12-T1039 (Trial #4, d90 = 81.53 μm) |
| 4 | Tecovirimat Granulate | Siga Technologies Lot # 1302679 |
| 5 | Tecovirimat Granulate | Siga Technologies Lot # 1401165 |
| 6 | Colloidal silicon dioxide, NF (Cabosil M5P) | Cabot Lot #1222272 |
| 7 | Croscarmellose sodium, NF (AcDiSol) | FMC Biopolymer Lot # TN12824921 |
| 8 | Lactose monohydrate, NF (SuperTab11SD) | DFE Lot # 10705838 |
| 9 | Lactose monohydrate, NF (SuperTab11SD) | DFE Lot # 10700181 |
| 10 | Lactose monohydrate, NF (SuperTab11SD) | DFE Lot # 10737298 |
| 11 | Microcrystalline cellulose, NF (Avicel PH101) | FMC Biopolymer Lot # P113825526 |
| 12 | Hypromellose, USP (Methocel E3 LV Premium) | Dow Lot # 1B020124L1 |
| 13 | Sodium lauryl sulfate, NF | Spectrum Lot # 1DB0596 |
| 14 | Purified Water, USP | Ricca Chemicals Lot # 4409016 |
| 15 | Sucralose, NF | Spectrum Lot # 1CF0697 |
| 16 | Sucralose, NF | Spectrum Lot # 1DF0586 |
| 17 | Strawberry flavor, #133.16296 | Bell Flavors |
| 18 | Black cherry nat type flavor | Kerry Lot # 260314 |
| 19 | Simethicone, USP (MED-340, simethicone content 100%) | Nusil Technologies Lot # 63865 |
| 20 | Simethicone Granular Solid, USP (MED-342, simethicone content 30%) | Nusil Technologies Lot # 63775 |
| 21 | Simethicone Granular Solid, USP (MED-342, simethicone content 30%) | Nusil Technologies Lot # 66777 |
| 22 | Simethicone Granular Solid, USP (MED-342, simethicone content 30%) | Nusil Technologies Lot # 67719 |
| 23 | Magnesium stearate, NF (HyQual) | Mallinckrodt Lot # 1301000109 |
| 24 | Crospovidone, USP/NF (Kollidon CL-M) | BASF Lot # 10204988Q0 |
| 25 | Povidone, USP/NF (Kollidon 12PF) | BASF Lot # 12714424U0 |
| 26 | Povidone, USP/NF (Kollidon, 90F) | BASF Lot # 45877768E0 |
| 27 | Hypromellose (Methocel F50) | Dow Lot # 2L03012N21 |
| 28 | Hypromellose (Methocel E50) | Dow Lot # 2C01012N23 |
| 29 | Methylcellulose, USP (Methocel A4M Premium) | Dow Lot # 2E19012N11 |
| 30 | Methylcellulose, 400 cps, USP | Spectrum Lot # 2CJ0081 |
| 31 | Methylcellulose, 400 cps, USP | Spectrum Lot # 2DC0205 |
| 32 | Methylcellulose, 15 cps, USP | Spectrum Lot # 2DE0263 |
| 33 | Hydroxypropyl cellulose, NF (Klucel JF Pharm) | Ashland Lot # 38296 |
| 34 | Hydroxypropyl cellulose, NF (Klucel JXF Pharm) | Ashland Lot # 40289 |
| 35 | Hydroxypropyl cellulose, NF (Klucel HF Pharm) | Ashland Lot # 49264 |

-continued

| S. # | Material | Supplier/Lot# |
|---|---|---|
| 36 | Hydroxypropyl cellulose, NF (Klucel MF Pharm) | Ashland Lot # 38949 |
| 37 | Hydroxylethyl cellulose, NF (Natrosol 250L Pharm) | Ashland Lot # J1967 |
| 38 | Carrageenan, NF (Gelcarin GP379) | FMC Biopolymer Lot # 50218031 |
| 39 | Carrageenan, NF (SeaSpen PF) | FMC Biopolymer Lot # 20226021 |
| 40 | Microcrystalline Cellulose and Sodium Carboxymethylcellulose, NF (Avicel RC-581) | FMC Biopolymer Lot # B1204C |
| 41 | Microcrystalline Cellulose and Sodium Carboxymethylcellulose, NF (Avicel CL-611) | FMC Biopolymer Lot # EN13825521 |
| 42 | Microcrystalline Cellulose and Sodium Carboxymethylcellulose, NF (Avicel RC-591) | FMC Biopolymer Lot # DN13825459 |
| 43 | Sodium Alginate, USP/NF (Protanal LFR5/60) | FMC Biopolymer Lot # H191208 |
| 44 | Xanthan gum, USP/NF (Xantural 75) | CP Kelco Lot # 2B4685K |
| 45 | Simethicone 50% Powder | AIC Lot # 4060-50205 |

Two typical dry suspensions are shown in Table 1. The dry suspensions according to the present invention contain granules of ST-246 and additional excipients to improve taste, suspendability, texture and flavor.

TABLE 1

| No. | Ingredient | Composition of Formulation DS83 (mg) | Composition of Formulation DS84 (mg) |
|---|---|---|---|
| 1 | Tecovirimat granulate | 346.5 | 346.5 |
| 2 | Lactose monohydrate (SuperTab 11SD, DMV Fonterra Excipients) | 93.0 | 0.0 |
| 3 | Klucel JF Pharm (Ashland) | 125.0 | 118.0 |
| 4 | Sucralose, USP | 10.0 | 10.0 |
| 5 | Flavor, black cherry (Virginia Dare, #23950) | 3.0 | 3.0 |
| 6 | Simethicone granular solid (NuSil MED-342) | 20.0 | 20.0 |
| 7 | Magnesium stearate | 2.5 | 2.5 |
| | Total | 600.0 | 500.0 |

Example 2: Development of the Dry Suspensions for Reconstitution. 200 mg

The composition of the Tecovirimat granulate is shown in Table 2. An oral powder for suspension using a suspending agent containing microcrystalline cellulose and sodium carboxymethylcellulose (Avicel CL-611) was used as a Target formulation is shown in Table 3. The target formulation exhibits good physical properties. However, the xanthan gum which is co-processed along with microcrystalline cellulose results in coagulation behavior during the dissolution tests due to the interaction with the surfactant used in the dissolution medium and thus poor drug release.

TABLE 2

Composition of ST-246 commercial granules

| S. No | Ingredients | Quantity per Unit (mg) |
|---|---|---|
| 1 | ST-246, Monohydrate, micronized | 209.00 |
| 2 | Microcrystalline Cellulose, NF (Avicel PH101) | 49.628 |
| 3 | Lactose Monohydrate, NF (Supertab 11SD) | 33.15 |
| 4 | Croscarmellose Sodium, NF (Ac-di-sol SD-711) | 31.2 |
| 5 | Colloidal Silicone Dioxide, NF (Cab-O-Sil ® M5P) | 1.95 |
| 6 | Hypromellose, USP (Methocel E3) | 13.65 |
| 7 | Sodium Lauryl Sulfate, NF | 7.80 |
| 8 | Purified Water*, USP | q.s. |
|  | Total | 346.4 |

*water is removed during drying

TABLE 3

ST-246 oral powder for suspension (Target Formulation)

| Ingredient | Prototype 1 (mg per dose) | Prototype 2 (mg per dose) |
|---|---|---|
| ST-246, granulate | 346.5 | 346.5 |
| Lactose monohydrate (SuperTab 11SD, DMV Fonterra Excipients) | 503.3 | 505.1 |
| Simethicone granular solid, (NuSil MED-342) | 10.0 | 10.0 |
| Avicel CL-611, NF (FMC BioPolymer) | 125.0 | 125.0 |
| Sucralose, USP | 10.0 | 10.0 |
| Flavor, strawberry (Kerry Item: U1-721636) | 5.0 | — |
| Flavor, black cherry (Kerry Item: U1-717664) | — | 3.0 |
| FD&C Red #3 | 0.10 | — |
| FD&C red #40 | — | 0.3 |
| Methylparaben, NF | 0.08 | 0.08 |
| Propylparaben, NF | 0.02 | 0.02 |
| Total | 1,000.0 | 1,000.0 |

Example 3: Screening and Selection of Suspending Agent

ST-246 granules prepared for capsule dosage form were used for the preparation of ST-246 oral powder for reconstitution, 200 mg. To evaluate the suspendability of the granules in various suspending agents, various suspending agents were dispersed in 50 mL purified water (Table 4). Concentrations of suspending agents in formulations DS-1 to DS-16 were produced according to the maximum potential from FDA Inactive Ingredient Guide (IIG). A placebo was prepared and compared visually with the target formulation and the concentration of suspending agent was adjusted accordingly in formulation DS-17 to DS-38

TABLE 4

Composition and Observation of Suspending Agent Placebo Solutions/Suspensions.

| Chemicals | Brand name | Formulation ID | Polymer quantity equilvalent to 10 doses (concentration) | Appearance | Disperse speed | Overnight sedimentation | Consistency (Visual observation in comparison with target formulation viscosity +++++) | Viscosity (cps, target formulation viscosity 50-100 cps) |
|---|---|---|---|---|---|---|---|---|
| Crospovidone | Kollidon CL-M | DS-1 | 2.500 g (5%, w/v) | white suspension | fast | sedimentation, easy to redisperse by shaking | less viscous ++ | not measured |
| Povidone (PVP) | Kollidon 90 F | DS-2 | 0.750 g (1.5%, w/v) | colorless solution | fast | none | less viscous + | not measured |
|  |  | DS-17 | 1.500 g (3%, w/v) | colorless solution | fast | none | less viscous + | not measured |
|  |  | DS-29 | 3.000 g (6%, w/v) | colorless solution | fast | none | comparable ++++ | 55.8 |
|  | Kollidon 12 PF | DS-3 | 0.750 g (1.5%, w/v) | colorless solution | fast | none | less viscous + | not measured |
|  |  | DS-18 | 1.500 g (3%, w/v) | colorless solution | fast | none | less viscous + | not measured |
|  |  | DS-30 | 3.000 g (6%, w/v) | colorless solution | fast | none | less viscous ++ | not measured |
| Hypromellose (HPMC) | Methocel F50 | DS-4 | 1.500 g (3%, w/v) | colorless solution | slow | none | comparable +++++ | 43.1 |
|  | Methocel E50 | DS-5 | 1.500 g (3%, w/v) | colorless solution | slow | none | comparable +++++ | 85.6 |
|  |  | DS-19 | 0.750 g (1.5%, w/v) | colorless solution | slow | none | less viscous ++ | not measured |
| Methylcellulose (MC) | Methocel A4MP | DS-6 | 0.595 g (1.19%, w/v) | colorless solution | slow | none | more viscous ++++++ | not measured |
|  |  | DS-26 | 0.250 g (0.5%, w/v) | colorless solution | slow | none | comparable ++++ | 24.9 |

TABLE 4-continued

Composition and Observation of Suspending Agent Placebo Solutions/Suspensions.

| Chemicals | Brand name | Formulation ID | Polymer quantity equilvalent to 10 doses (concentration) | Appearance | Disperse speed | Overnight sedimentation | Consistency (Visual observation in comparison with target formulation viscosity +++++) | Viscosity (cps, target formulation viscosity 50-100 cps) |
|---|---|---|---|---|---|---|---|---|
| | Methyl cellulose, 400 cps | DS-7 | 0.595 g (1.19%, w/v) | colorless solution | slow | none | comparable +++++ | not measured |
| | | DS-27 | 0.250 g (0.5%, w/v) | colorless solution | slow | none | comparable ++++ | 17.1 |
| Hydroxypropyl cellulose (HPC) | Klucel JF Pharm | DS-8 | 3.350 g (6.7%, w/v) | colorless solution | slow | none | more viscous +++++++ | not measured |
| | | DS-20 | 0.750 g (1.5%, w/v) | colorless solution | slow | none | less viscous ++ | not measured |
| | | DS-31 | 1.500 g (3%, w/v) | colorless solution | slow | none | comparable ++++ | 20.4 |
| | Klucel HF Pharm | DS-9 | 3.350 g (6.7%, w/v) | colorless gel | slow | none | more viscous, gel, high viscosity | not measured |
| | | DS-21 | 0.500 g (1.0%, w/v) | colorless solution | slow | none | more viscous ++++++++ | not measured |
| | | DS-33 | 0.375 g (0.75%, w/v) | colorless solution | slow | none | comparable ++++++ | 123.9 |
| | Klucel MF Pharm | DS-10 | 3.350 g (6.7%, w/v) | colorless gel | slow | none | more viscous, gel, high viscosity | not measured |
| | | DS-22 | 0.500 g (1.0%, w/v) | colorless solution | slow | none | more viscous +++++++ | not measured |
| | | DS-34 | 0.375 g (0.75%, w/v) | colorless solution | slow | none | comparable +++++ | 71.0 |
| Hydroxyethyl cellulose (HEC) | Natrosol 250L Pharm | DS-11 | 1.500 g (3%, w/v) | yellowish solution | fast | none | comparable ++++ | 14.9 |
| | | DS-28 | 2.000 g (4%, w/v) | yellowish solution | fast | none | comparable ++++ | not measured |
| Carrageenan | Gelcarin GP379 | DS-12 | 0.750 g (1.5%, w/v) | yellowish gel | slow | none | more viscous, gel, high viscosity | not measured |
| | | DS-23 | 0.200 g (0.4%, w/v) | yellowish solution | slow | none | comparable +++++ | 65.5 |
| | SeaSpen PF | DS-13 | 0.750 g (1.5%, w/v) | milky gel | slow | none | more viscous, gel, high viscosity | not measured |
| | | DS-24 | 0.200 g (0.4%, w/v) | milky solution | slow | none | comparable ++++++ | 20.1 |
| Microcrystalline cellulose/sodium carboxymethyl cellulose (MCC/CMCNa) | Avicel RC-581 | DS-14 | 1.500 g (3%, w/v) | white suspension | fast | none | more viscous +++++++ | not measured |
| | | DS-35 | 1.250 g (2.5%, w/v) | white suspension | fast | none | comparable ++++++ | 84.3 |
| | Avicel CL-611 | DS-15 | 1.500 g (3%, w/v) | white suspension | fast | none | more viscous +++++++ | not measured |
| | | DS-36 | 1.250 g (2.5%, w/v) | white suspension | fast | none | comparable +++++ | 35.4 |
| | Avicel RC-591 | DS-37 | 1.250 g (2.5%, w/v) | white suspension | fast | none | comparable ++++++ | 93.8 |
| Sodium Alginate | Protanal LFR 5/60 | DS-16 | 0.062 g (0.123%, w/v) | colorless solution | fast | none | less viscous + | not measured |
| | | DS-25 | 0.800 g (1.6%, w/v) | yellowish solution | slow | none | less viscous ++ | not measured |
| | | DS-32 | 1.600 g (3.2%, w/v) | yellowish solution | slow | none | less viscous ++++ | not measured |
| | | DS-38 | 2.000 g (4%, w/v) | yellowish solution | slow | none | comparable +++++ | 32.4 |

Povidone (Kollidon 90 F) 6%, Hypromellose (Methocel F 50 and E50) 3%, Methylcellulose (Methocel A4MP), Methyl Cellulose 400 cps 0.5%, Hydroxypropyl cellulose (Klucel HF and MF) 0.75%, Hydroxy Ethyl Cellulose (Natrosol 250 L Pharm) 3%, Avicel RC-581-2.5%, Avicel RC-591-2.5% and Sodium alginate 4% show comparable viscosity to the Target formulation containing Avicel CL-611.

The suspending agent concentrations with comparable consistency to that of the Target formulation (containing Avicel CL-611 as suspending agent) were selected as the formulation viscosity modifier.

Example 4: Formulation of Suspensions by Mixing ST-246 Granules with Formulation Vehicles To evaluate the suspendability of ST-246, ingredients such as sucralose, simethicone (adsorbed on lactose monohydrate) and suspension polymers were added. Lactose monohydrate was added to make up the weight of the composition. These ingredients were mixed with the selected suspending agent vehicle concentration from Example 3. The resultant compositions are given in Table 5.

The formulation procedure included:

1. Adsorbing 1 g of simethicone (MED-340, liquid) on 19 g lactose monohydrate (SuperTab 11SD).
2. Geometric mixing of the ST-246 granules, sucralose, simethicone adsorbed on lactose, and lactose monohydrate to make 5 g (5 doses) blends considering the quantity of polymer quantity sufficient (Q.S.) to 25 mL of vehicle.
3. Dispersing the blend in Q.S. to 25 mL of formulation vehicle prepared in Example 3.
4. Evaluation of the sedimentation, redispersibility, and pH of the suspensions.
5. Transfer of each of about 5 mL of suspension in screw cap glass vials, to store the samples at room temperature, at 2 to 8° C. and at 40° C./75% RH for 14 Days and recording the observations. Table 6 shows the results of physical properties of suspensions.

TABLE 5

Composition of suspensions - Suspending Agent Selection

| S.# | Ingredients | DS-39 | DS-40 | DS-41 | DS-42 | DS-43 | DS-44 | DS-45 | DS-46 |
|---|---|---|---|---|---|---|---|---|---|
| | | Quantity (g) Equivalent to 5 doses | | | | | | | |
| 1 | ST-246 Granules | 1.733 | 1.733 | 1.733 | 1.733 | 1.733 | 1.733 | 1.733 | 1.733 |
| 2 | Sucralose, NF | 0.050 | 0.050 | 0.050 | 0.050 | 0.050 | 0.050 | 0.050 | 0.050 |
| 3 | Simethicone, USP (MED-340) | 0.025 | 0.025 | 0.025 | 0.025 | 0.025 | 0.025 | 0.025 | 0.025 |
| 4 | Lactose Monohydrate, NF (SuperTab 11SD) | 0.475 | 0.475 | 0.475 | 0.475 | 0.475 | 0.475 | 0.475 | 0.475 |
| 5 | Lactose Monohydrate, NF (SuperTab 11SD) | 1.967 | 1.967 | 1.967 | 2.617 | 2.617 | 2.592 | 2.592 | 1.217 |
| 6 | Hypromellose (Methocel F 50), 3% Dispersion | 25.750 | — | — | — | — | — | — | — |
| | Hypromellose (Methocel E 50), 3% Dispersion | — | 25.750 | — | — | — | — | — | — |
| | Hydroxyethyl cellulose (Natrosol 250L), 3% Dispersion | — | — | 25.750 | — | — | — | — | — |
| | Carrageenan (Iota) (Gelcarin GP379), 0.4% Dispersion | — | — | — | 25.100 | — | — | — | — |
| | Carrageenan (Iota) (SeaSpen PF), 0.4% Dispersion | — | — | — | — | 25.100 | — | — | — |
| | Methyl Cellulose (Methocel A4MP), 0.5% Dispersion | — | — | — | — | — | 25.125 | — | — |
| | Methyl Cellulose, 400 cps, 0.5% Dispersion | — | — | — | — | — | — | 25.125 | — |
| | Povidone (Kollidon 90F), 6% Dispersion | — | — | — | — | — | — | — | 26.500 |
| | Hydroxypropyl cellulose (Klucel JF Pharm), 3% Dispersion | — | — | — | — | — | — | — | — |
| | Hydroxypropyl cellulose (Klucel HF Pharm), 0.75% Dispersion | — | — | — | — | — | — | — | — |
| | Hydroxypropyl cellulose (Klucel MF Pharm), 0.75% Dispersion | — | — | — | — | — | — | — | — |
| | Microcrystalline cellulose and carboxymethyl cellulose (Avicel RC-581), 2.5% Dispersion | — | — | — | — | — | — | — | — |
| | Microcrystalline cellulose and carboxymethyl cellulose (Avicel CL-611), 2.5% Dispersion | — | — | — | — | — | — | — | — |
| | Microcrystalline cellulose and carboxymethyl cellulose (Avicel RC-591), 2.5% Dispersion | — | — | — | — | — | — | — | — |
| | Sodium Alginate (Protanal LFR 5/60), 4% Dispersion | — | — | — | — | — | — | — | — |

| S.# | Ingredients | DS-47 | DS-48 | DS-49 | DS-50 | DS-51 | DS-52 | DS-53 |
|---|---|---|---|---|---|---|---|---|
| | | Quantity (g) Equivalent to 5 doses | | | | | | |
| 1 | ST-246 Granules | 1.733 | 1.733 | 1.733 | 1.733 | 1.733 | 1.733 | 1.733 |
| 2 | Sucralose, NF | 0.050 | 0.050 | 0.050 | 0.050 | 0.050 | 0.050 | 0.050 |
| 3 | Simethicone, USP (MED-340) | 0.025 | 0.025 | 0.025 | 0.025 | 0.025 | 0.025 | 0.025 |

TABLE 5-continued Composition of suspensions - Suspending Agent Selection

| | | | | | | | | |
|---|---|---|---|---|---|---|---|---|
| 4 | Lactose Monohydrate, NF (SuperTab 11SD) | 0.475 | 0.475 | 0.475 | 0.475 | 0.475 | 0.475 | 0.475 |
| 5 | Lactose Monohydrate, NF (SuperTab 11SD) | 1.967 | 2.530 | 2.530 | 2.092 | 2.092 | 2.092 | 1.717 |
| 6 | Hypromellose (Methocel F 50), 3% Dispersion | — | — | — | — | — | — | — |
|   | Hypromellose (Methocel E 50), 3% Dispersion | — | — | — | — | — | — | — |
|   | Hydroxyethyl cellulose (Natrosol 250L), 3% Dispersion | — | — | — | — | — | — | — |
|   | Carrageenan (Iota) (Gelcarin GP379), 0.4% Dispersion | — | — | — | — | — | — | — |
|   | Carrageenan (Iota) (SeaSpen PF), 0.4% Dispersion | — | — | — | — | — | — | — |
|   | Methyl Cellulose (Methocel A4MP), 0.5% Dispersion | — | — | — | — | — | — | — |
|   | Methyl Cellulose, 400 cps, 0.5% Dispersion | — | — | — | — | — | — | — |
|   | Povidone (Kollidon 90F), 6% Dispersion | — | — | — | — | — | — | — |
|   | Hydroxypropyl cellulose (Klucel JF Pharm), 3% Dispersion | 25.750 | — | — | — | — | — | — |
|   | Hydroxypropyl cellulose (Klucel HF Pharm), 0.75% Dispersion | — | 25.187 | — | — | — | — | — |
|   | Hydroxypropyl cellulose (Klucel MF Pharm), 0.75% Dispersion | — | — | 25.187 | — | — | — | — |
|   | Microcrystalline cellulose and carboxymethyl cellulose (Avicel RC-581), 2.5% Dispersion | — | — | — | 25.625 | — | — | — |
|   | Microcrystalline cellulose and carboxymethyl cellulose (Avicel CL-611), 2.5% Dispersion | — | — | — | — | 25.625 | — | — |
|   | Microcrystalline cellulose and carboxymethyl cellulose (Avicel RC-591), 2.5% Dispersion | — | — | — | — | — | 25.625 | — |
|   | Sodium Alginate (Protanal LFR 5/60), 4% Dispersion | — | — | — | — | — | — | 26.000 |

The sedimentation coefficients were determined by measuring the height of the suspension in a 40 cc vial divided by the height of the sediment in a vial. Sedimentation coefficient versus time is used as an indicator as to the stability of suspension over the time.

The redispersibility was evaluated by centrifuging the suspension in Eppendorf tube at 5000 rpm for 10 minutes followed by shaking manually or with wrist action shaker, if the sediment in centrifuge suspended again, it was recorded as "redispersible."

TABLE 6

Characterization of Physical Stability of Selected Formulations

| | | Formulation ID | | | | |
|---|---|---|---|---|---|---|
| | | DS-39 | DS-40 | DS-41 | DS-42 | DS-43 |
| | | | | Polymer | | |
| | | Methocel F50 3% w/v | Methocel E50 3% w/v | Natrosol 250L 3% w/v | Gelcarin GP379 0.4% w/v | SeaSpen PF 0.4% w/v |
| | | | | Observations | | |
| 1 | Appearance | White dispersion | White dispersion | White dispersion | White dispersion | White dispersion |
| 2 | Sedimentation Coeff (10 min) | 1.00 | 1.00 | 1.00 | 1.00 | 1.00 |
| 3 | Sedimentation Coeff (30 min) | 1.00 | 1.00 | 1.00 | 1.00 | 1.00 |
| 4 | Sedimentation Coeff (12 h) | 1.00 | 1.00 | 0.72 | 0.46 | 1.00 |
| 5 | Sedimentation Coeff (24 h) | 1.00 | 1.00 | 0.58 | 0.38 | 1.00 |
| 6 | Observation at the time of mixing the solids with the formulation vehicle | None | None | None | None | None |

TABLE 6-continued

Characterization of Physical Stability of Selected Formulations

|   |   |   |   |   |   |   |
|---|---|---|---|---|---|---|
| 7 | Redispersibility after 24 hours (gentle shaking) | No sedimentation | No sedimentation | Redispersible | Redispersible | No sedimentation |
| 8 | pH | 5.62 | 5.81 | 5.57 | 5.30 | 6.67 |

Observations
Stability: 2-8° C. for 14 days

|   |   |   |   |   |   |   |
|---|---|---|---|---|---|---|
| 1 | Appearance (Color) | white | white | white | white | white |
| 2 | Signs of Creaming, flocculation | two layers | two layers | almost clear supernatant | clear supernatant | uniform |
| 3 | Sedimentation Coeff | 0.98 | 0.99 | 0.34 | 0.34 | 0.97 |
| 4 | Redispersibility | redispersible | redispersible | redispersible | redispersible | redispersible |

Stability: 40° C./75% RH for 14 days

|   |   |   |   |   |   |   |
|---|---|---|---|---|---|---|
| 1 | Appearance (Color) | white | white | white | white | white |
| 2 | Signs of Creaming, flocculation | two layers | two layers | clear supernatant | clear supernatant | clear supernatant |
| 3 | Sedimentation Coeff | 0.97 | 0.98 | 0.34 | 0.37 | 0.34 |
| 4 | Redispersibility | redispersible | redispersible | redispersible | redispersible | redispersible |

Stability: Room temperature for 14 days

|   |   |   |   |   |   |   |
|---|---|---|---|---|---|---|
| 1 | Appearance (Color) | white | white | white | white | white |

Observations

|   |   |   |   |   |   |   |
|---|---|---|---|---|---|---|
| 2 | Signs of Creaming, flocculation | two layers | two layers | clear supernatant | clear supernatant | clear supernatant |
| 3 | Sedimentation Coeff | 0.98 | 0.97 | 0.30 | 0.32 | 0.76 |
| 4 | Redispersibility | redispersible | redispersible | redispersible | redispersible | redispersible |
| 5 | pH | 5.62 | 5.58 | 5.49 | 5.25 | 6.77 |

| | Formulation ID | | | | |
|---|---|---|---|---|---|
| | DS-44 | DS-45 | DS-46 | DS-47 | DS-48 |
| | | | Polymer | | |
| | Methocel A4MP 0.5% w/v | MC, 400 cps 0.5% w/v | Kollidon 90F 6% w/v | Klucel JF 3% w/v | Klucel HF 0.75% w/v |

Observations

|   |   |   |   |   |   |   |
|---|---|---|---|---|---|---|
| 1 | Appearance | White dispersion | White dispersion | White dispersion | White dispersion | White dispersion |
| 2 | Sedimentation Coeff (10 min) | 1.00 | 1.00 | 1.00 | 1.00 | 1.00 |
| 3 | Sedimentation Coeff (30 min) | 1.00 | 1.00 | 1.00 | 1.00 | 1.00 |
| 4 | Sedimentation Coeff (12 h) | 1.00 | 1.00 | 0.51 | 1.00 | 1.00 |
| 5 | Sedimentation Coeff (24 h) | 1.00 | 0.92 | 0.41 | 1.00 | 1.00 |
| 6 | Observation at the time of mixing the solids with the formulation vehicle | None | None | None | Thickening of formulation | Thickening of formulation, gel |
| 7 | Redispersibility after 24 hours (gentle shaking) | No sedimentation | Redispersible | Redispersible | No sedimentation | No sedimentation |
| 8 | pH | 5.71 | 5.78 | 5.67 | 5.76 | Not checked |

Observations
Stability: 2-8° C. for 14 days

|   |   |   |   |   |   |   |
|---|---|---|---|---|---|---|
| 1 | Appearance (Color) | white | white | white | white | Not checked |
| 2 | Signs of Creaming, flocculation | two layers | two layers | clear supernatant | two layers | |
| 3 | Sedimentation Coeff | 0.97 | 0.95 | 0.31 | 0.98 | |
| 4 | Redispersibility | redispersible | redispersible | redispersible | redispersible | |

TABLE 6-continued

Characterization of Physical Stability of Selected Formulations

Stability: 40° C./75% RH for 14 days

| | | | | | | |
|---|---|---|---|---|---|---|
| 1 | Appearance (Color) | white | white | white | white | Not checked |
| 2 | Signs of Creaming, flocculation | clear supernatant, sedimentation two layers | clear supernatant, sedimentation two layers | clear supernatant | a thin clear supernatant, a thick flocculation layer | |
| 3 | Sedimentation Coeff | 0.52 | 0.56 | 0.34 | 0.59 | |
| 4 | Redispersibility | redispersible | redispersible | redispersible | redispersible | |

Stability: Room temperature for 14 days

| | | | | | | |
|---|---|---|---|---|---|---|
| 1 | Appearance (Color) | white | white | white | white | white |

Observations

| | | | | | | |
|---|---|---|---|---|---|---|
| 2 | Signs of Creaming, flocculation | two layers | two layers | opaque supernatant | opaque supernatant | very viscous gel |
| 3 | Sedimentation Coeff | 0.65 | 0.94 | 0.30 | 0.42 | 1.00 |
| 4 | Redispersibility | redispersible | redispersible | redispersible | redispersible | too viscous |
| 5 | pH | 5.65 | 5.66 | 5.44 | 5.49 | 4.74 |

| | | Formulation ID | | | | |
|---|---|---|---|---|---|---|
| | | DS-49 | DS-50 | DS-51 | DS-52 | DS-53 |
| | | | | Polymer | | |
| | | Klucel MF 0.75% w/v | Avicel RC-581 2.5% w/v | Avicel CL-611 2.5% w/v | Avicel RC-591 2.5% w/v | Protanal LFR5/60 4% w/v |

Observations

| | | | | | | |
|---|---|---|---|---|---|---|
| 1 | Appearance | White dispersion | White dispersion | White dispersion | White dispersion | White dispersion |
| 2 | Sedimentation Coeff (10 min) | 1.00 | 1.00 | 1.00 | 1.00 | 1.00 |
| 3 | Sedimentation Coeff (30 min) | 1.00 | 1.00 | 1.00 | 1.00 | 1.00 |
| 4 | Sedimentation Coeff (12 h) | 1.00 | 1.00 | 1.00 | 1.00 | 0.27 |
| 5 | Sedimentation Coeff (24 h) | 1.00 | 1.00 | 1.00 | 1.00 | 0.23 |
| 6 | Observation at the time of mixing the solids with the formulation vehicle | Thickening of formulation, gel | None | None | None | Thinning of formulation after overnight standing |
| 7 | Redispersibility after 24 hours (gentle shaking) | No sedimentation | No sedimentation | No sedimentation | No sedimentation | Redispersible, but agglomerates were found |
| 8 | pH | Not checked | 5.58 | 5.56 | 5.57 | 5.16 |

Observations
Stability: 2-8° C. for 14 days

| | | | | | | |
|---|---|---|---|---|---|---|
| 1 | Appearance (Color) | Not checked | white | white | white | white |
| 2 | Signs of Creaming, flocculation | | creamy, phase separation | uniform | creamy | clear supernatant |
| 3 | Sedimentation Coeff | | 0.83 | 1.00 | 1.00 | 0.21 |
| 4 | Redispersibility | | redispersible | redispersible | redispersible | redispersible |

Stability: 40° C./75% RH for 14 days

| | | | | | | |
|---|---|---|---|---|---|---|
| 1 | Appearance (Color) | Not checked | white | white | white | white |
| 2 | Signs of Creaming, flocculation | | creamy, phase separation | uniform | creamy | clear supernatant |
| 3 | Sedimentation Coeff | | 0.78 | 1.00 | 1.00 | 0.34 |
| 4 | Redispersibility | | redispersible | redispersible | redispersible | redispersible |

TABLE 6-continued

Characterization of Physical Stability of Selected Formulations

Observations

Stability: Room temperature for 14 days

| | | | | | | |
|---|---|---|---|---|---|---|
| 1 | Appearance (Color) | white | white | white | white | white |
| 2 | Signs of Creaming, flocculation | very viscous gel | creamy, phase separation | uniform | uniform | clear supernatant |
| 3 | Sedimentation Coeff | 1.00 | 0.84 | 1.00 | 1.00 | 0.33 |
| 4 | Redispersibility | too viscous | redispersible | redispersible | redispersible | redispersible |
| 5 | pH | 5.65 | 5.53 | 5.49 | 5.50 | 5.14 |

Suspensions were prepared using 3% Methocel F50, 3% Methocel E50, 0.5% Methocel A4MP, 0.5% Methylcellulose 400 cps, or 3% Klucel JF as suspending agents and showed comparable physical properties as the Target formulation using 2.5% Avicel CL-611 as a vehicle, and also showed comparable results of physical stability when stored at 2 to 8° C., room temperature and at 40° C./75% RH for the reconstitution study.

Example 5: Formulation and Evaluation of Powders for Reconstitution Using Selected Polymers Solid blends (including suspending agents selected in Example 4) were formulated, and the rates of reconstitution (hydration time) in water were evaluated. Compositions are given in Table 7.

The formulation procedure was as follows;
1. Adsorbing of 1 g of simethicone (MED-340, liquid) on 19 g lactose monohydrate (SuperTab 11SD)
2. Geometric mixing of Tecovirimat granules, sucralose, and simethicone adsorbed lactose, then weighing of quantity equivalent to 10 units of blend and then geometric mixing with other components for each formulation;
3. Dispersing of the blend in purified water to make Q.S. to 50 mL;
4. Observing the rate of reconstitution, sedimentation, redispersibility, and pH of the suspensions (see Table 8);
5. Storing the samples at room temperature, at 2 to 8° C. and at 40° C./75% RH for 14 Days and recording the observations (see Table 9);

TABLE 7

Composition of solid blends (including suspending agents) for reconstitution (40 mg/ml).

| | | Quantity per unit (mg) | | | | |
|---|---|---|---|---|---|---|
| S.# | Ingredients | DS-54 | DS-55 | DS-56 | DS-57 | DS-58 |
| 1 | ST-246 Granules* | 346.50 | 346.50 | 346.50 | 346.50 | 346.50 |
| 2 | Sucralose, NF | 10.00 | 10.00 | 10.00 | 10.00 | 10.00 |
| 3 | Simethicone, USP (MED-340) | 5.00 | 5.00 | 5.00 | 5.00 | 5.00 |
| 4 | Lactose Monohydrate, NF (SuperTab 11SD) | 95.00 | 95.00 | 95.00 | 95.00 | 95.00 |
| 5 | Lactose Monohydrate, NF (SuperTab 11SD) | 393.50 | 393.50 | 518.50 | 518.50 | 393.50 |
| 6 | Hypromellose (Methocel F50) | 150.00 | — | — | — | — |
| | Hypromellose (Methocel E50) | — | 150.00 | — | — | — |
| | Methyl Cellulose (Methocel A4MP), USP | — | — | 25.00 | — | — |
| | Methyl Cellulose, 400 cps, USP | — | — | — | 25.00 | — |
| | Hydroxypropyl cellulose (Klucel JF Pharm), NF | — | — | — | — | 150.00 |
| 7 | Purified water, USP, Q.S. to 5 mL | — | — | — | — | — |
| | Total | 1000.00 | 1000.00 | 1000.00 | 1000.00 | 1000.00 |

*granules equivalent to 200 mg Tecovirimat

6. Conducting a freeze-thawing cycle of 3-day −10° C. and 3-day room temperature and repeating 5 times and recording the observations (see Table 10 and 11).

TABLE 8

Observation of reconstitution and 1-day sedimentation of DS-54 to DS-58

| | | Formulation ID | | | | |
|---|---|---|---|---|---|---|
| | | DS-54 | DS-55 | DS-56 | DS-57 | DS-58 |
| | | | | Polymer | | |
| | | Methocel F50 3% w/v | Methocel E50 3% w/v | Methocel A4MP 0.5% w/v | MC, 400 cps 0.5% w/v | Klucel JF 3% w/v |
| | Observations T = 0, room temperature | | | | | |
| 1 | Time for reconstitution (min) | 7 | 7 | 1 | 1 | 2 |
| 2 | Observation for reconstitution | Still chunks remaining at bottom after shaking | Still chunks remaining at bottom after shaking | No chunks remaining, easy to disperse | No chunks remaining, easy to disperse | Small chunks remaining at bottom after shaking |
| 3 | Appearance (visual) | white, uniform | white, uniform | white, uniform | white, uniform | white, uniform |
| 4 | pH | 5.76 | 5.81 | 5.86 | 5.89 | 5.78 |
| 5 | Particle size (µm) | 3.20 ± 2.56 | 3.03 ± 1.91 | 3.85 ± 3.11 | 3.31 ± 2.43 | 3.86 ± 3.31 |
| 6 | Forced settling and Redispersibility | redispersible | redispersible | redispersible | redispersible | redispersible |
| | Observations T = 30 min, room temperature | | | | | |
| 1 | Sedimentation Coefficient | 1.00 | 1.00 | 1.00 | 1.00 | 1.00 |
| 2 | Appearance (visual) | white, uniform | white, uniform | white, uniform | white, uniform | white, uniform |
| 3 | Redispersibility | redispersible | redispersible | redispersible | redispersible | redispersible |
| | Observations T = 1 hr, room temperature | | | | | |
| 1 | Sedimentation Coefficient | 1.00 | 1.00 | 1.00 | 1.00 | 1.00 |
| 2 | Appearance (visual) | white, uniform | white, uniform | white, uniform | white, uniform | white, uniform |
| 3 | Redispersibility | redispersible | redispersible | redispersible | redispersible | redispersible |
| | Observations T = 24 hr, room temperature | | | | | |
| 1 | Sedimentation Coefficient | 1.00 | 1.00 | 1.00 | 0.98 | 0.95 |
| 2 | Appearance (visual) | white, uniform | white, uniform | two layers | two layers | opaque supernatant with floccules |
| 3 | Redispersibility | redispersible | redispersible | redispersible | redispersible | redispersible |

TABLE 9

14-Days stability of DS-54 to DS-58

| | | Formulation ID | | | | |
|---|---|---|---|---|---|---|
| | | DS-54 | DS-55 | DS-56 | DS-57 | DS-58 |
| | | | | Polymer | | |
| | | Methocel F50 3% w/v | Methocel E50 3% w/v | Methocel A4MP 0.5% w/v | MC, 400 cps 0.5% w/v | Klucel JF 3% w/v |
| | Observations T = 7 days, room temperature | | | | | |
| 1 | Sedimentation Coefficient | 0.95 | 0.97 | 0.95 | 0.96 | 0.65 |
| 2 | Appearance (visual) | two layers | two layers | two layers | two layers | opaque supernatant with floccules |
| 3 | Redispersibility | redispersible | redispersible | redispersible | redispersible | redispersible |
| 4 | pH | 5.72 | 5.79 | 5.77 | 5.78 | 5.70 |
| 5 | Particle size (µm) | 3.33 ± 2.67 | 3.37 ± 2.29 | 3.11 ± 1.88 | 3.37 ± 1.96 | 3.20 ± 2.13 |
| | Observations T = 7 days, 2-8° C. | | | | | |
| 1 | Sedimentation Coefficient | 0.97 | 0.97 | 0.98 | 0.99 | 0.87 |
| 2 | Appearance (visual) | two layers | two layers | two layers | two layers | opaque supernatant with floccules |
| 3 | Redispersibility | redispersible | redispersible | redispersible | redispersible | redispersible |
| 4 | pH | 5.75 | 5.82 | 5.81 | 5.79 | 5.75 |
| 5 | Particle size (µm) | 3.13 ± 2.18 | 3.20 ± 2.30 | 3.51 ± 2.37 | 3.37 ± 2.08 | 3.57 ± 2.52 |
| | Observations T = 7 days, 40° C./75%RH | | | | | |
| 1 | Sedimentation Coefficient | 0.35 | 0.43 | 0.44 | 0.41 | 0.81 |
| 2 | Appearance (visual) | milky supernatant | opaque supernatant | clear supernatant with floccules | opaque supernatant | opaque supernatant with floccules |

TABLE 9-continued

14-Days stability of DS-54 to DS-58

| | | Formulation ID | | | | |
|---|---|---|---|---|---|---|
| | | DS-54 | DS-55 | DS-56 | DS-57 | DS-58 |
| | | | | Polymer | | |
| | | Methocel F50 3% w/v | Methocel E50 3% w/v | Methocel A4MP 0.5% w/v | MC, 400 cps 0.5% w/v | Klucel JF 3% w/v |
| 3 | Redispersibility | redispersible | redispersible | redispersible | redispersible | redispersible |
| 4 | pH | 5.48 | 5.55 | 5.53 | 5.57 | 5.44 |
| 5 | Particle size (μm) | 3.51 ± 2.49 | 3.45 ± 2.54 | 3.86 ± 2.55 | 3.96 ± 3.00 | 3.81 ± 2.37 |
| | | | Observations T = 14 days, room temperature | | | |
| 1 | Sedimentation Coefficient | 0.96 | 0.96 | 0.49 | 0.96 | 0.69 |
| 2 | Appearance (visual) | two layers | two layers | two layers, clear supernatant with floccules | two layers | opaque supernatant with floccules |
| 3 | Redispersibility | redispersible | redispersible | redispersible; sedimentation occurs at 30 min after shaking | redispersible | redispersible |
| 4 | pH | 5.68 | 5.69 | 5.72 | 5.71 | 5.64 |
| 5 | Particle size (μm) | 3.69 ± 2.45 | 3.54 ± 2.68 | 3.51 ± 2.78 | 3.68 ± 2.95 | 3.48 ± 2.66 |
| | | | Observations T = 14 days, 2-8°C. | | | |
| 1 | Sedimentation Coefficient | 0.96 | 0.96 | 0.96 | 0.95 | 0.90 |
| 2 | Appearance (visual) | two layers | two layers | two layers | two layers | opaque supernatant with floccules |
| 3 | Redispersibility | redispersible | redispersible | redispersible | redispersible | redispersible |
| 4 | pH | 5.74 | 5.75 | 5.75 | 5.78 | 5.76 |
| 5 | Particle size (μm) | 3.86 ± 2.86 | 3.57 ± 2.44 | 3.46 ± 2.58 | 3.76 ± 2.74 | 3.78 ± 2.68 |
| | | | Observations T = 14 days, 40° C./75%RH | | | |
| 1 | Sedimentation Coefficient | 0.74 | 0.78 | 0.39 | 0.33 | 0.60 |
| 2 | Appearance (visual) | clear supernatant with floccules | clear supernatant with floccules | clear supernatant with floccules, an opaque flocculation layer between clear supernatant and sedimentation | clear supernatant with floccules, an opaque flocculation layer between clear supernatant and sedimentation | clear supernatant with floccules, an opaque flocculation layer between clear supernatant and sedimentation |
| 3 | Redispersibility | redispersible | redispersible | redispersible; curdy, loose sedimentation right away after shaking | redispersible; curdy, loose sedimentation right away after shaking | redispersible |
| 4 | pH | 5.32 | 5.32 | 5.40 | 5.40 | 5.32 |
| 5 | Particle size (μm) | 3.93 ± 3.00 | 3.86 ± 3.08 | 3.94 ± 3.03 | 3.96 ± 3.10 | 3.83 ± 2.72 |

TABLE 10

Observations for freeze-thawing cycles of −10° C. (3-day) and RT (3-day)

| | | Formulation ID | | | | |
|---|---|---|---|---|---|---|
| | | DS-54 | DS-55 | DS-56 | DS-57 | DS-58 |
| | | | | Polymer | | |
| | | Methocel F50 3% w/v | Methocel E50 3% w/v | Methocel A4MP 0.5% w/v | MC, 400 cps 0.5% w/v | Klucel JF 3% w/v |
| | | Observations after Freeze-Thawing Cycle: storage at −10° C. for 3 days followed by at RT for 3 days | | | | |
| Sedimentation Coefficient | 1 Cycle | 0.96 | 0.96 | 0.48 | 0.34 | 0.66 |
| | 2 Cycle | 0.96 | 0.96 | 0.50 | 0.34 | 0.67 |
| | 3 Cycle | 0.96 | 0.96 | 0.50 | 0.34 | 0.54 |
| | 4 Cycle | 0.96 | 0.96 | 0.49 | 0.30 | 0.70 |
| | 5 Cycle | 0.96 | 0.96 | 0.49 | 0.38 | 0.79 |
| Appearance (visual) | 1 Cycle | uniform | uniform | clear supernatant with floccules, a thin opaque flocculation layer between clear supernatant and sedimentation | sedimentation two layers, opaque supernatant with floccules | opaque supernatant with floccules |

TABLE 10-continued

Observations for freeze-thawing cycles of −10° C. (3-day) and RT (3-day)

| | | Formulation ID | | | | |
|---|---|---|---|---|---|---|
| | | DS-54 | DS-55 | DS-56 | DS-57 | DS-58 |
| | | Polymer | | | | |
| | | Methocel F50 3% w/v | Methocel E50 3% w/v | Methocel A4MP 0.5% w/v | MC, 400 cps 0.5% w/v | Klucel JF 3% w/v |
| | | Observations after Freeze-Thawing Cycle: storage at −10° C. for 3 days followed by at RT for 3 days | | | | |
| | 2 Cycle | sedimentation two layers | uniform | clear supernatant | sedimentation two layers, opaque supernatant with floccules | opaque supernatant with floccules |
| | 3 Cycle | sedimentation two layers | uniform | clear supernatant, sedimentation two layers | opaque to clear supernatant, sedimentation two layers | A thin clear supernatant on top, a thick opaque flocculation layer between clear supernatant and sedimentation |
| | 4 Cycle | uniform | uniform | clear supernatant | clear supernatant, a milky flocculation layer between clear supernatant and sedimentation | opaque supernatant with floccules |
| | 5 Cycle | uniform | uniform | clear supernatant | clear supernatant, a milky flocculation layer between clear supernatant and sedimentation, sedimentation two layers | opaque supernatant with floccules |
| Redispersibility | 1 Cycle | redispersible | redispersible | redispersible; sedimentation occurs at 10 min after shaking | redispersible | redispersible |
| | 2 Cycle | redispersible | redispersible | redispersible; sedimentation occurs at 10 min after shaking | redispersible | redispersible |
| | 3 Cycle | redispersible | redispersible | redispersible; sedimentation occurs at 10 min after shaking, sedimentation appears loose and curdy | redispersible; sedimentation occurs at 10 min after shaking | redispersible |
| | 4 Cycle | redispersible | redispersible | redispersible; sedimentation occurs at 10 min after shaking, sedimentation appears loose and curdy | redispersible; sedimentation occurs at 10 min after shaking | redispersible |
| | 5 Cycle | redispersible | redispersible | redispersible; sedimentation occurs at 10 min after shaking, sedimentation appears loose and curdy | redispersible; sedimentation occurs at 10 min after shaking | redispersible |
| pH | 1 Cycle | 5.66 | 5.66 | 5.69 | 5.70 | 5.64 |
| | 2 Cycle | 5.62 | 5.63 | 5.66 | 5.69 | 5.57 |
| | 3 Cycle | 5.60 | 5.58 | 5.62 | 5.66 | 5.52 |
| | 4 Cycle | 5.61 | 5.56 | 5.60 | 5.61 | 5.54 |
| | 5 Cycle | 5.65 | 5.67 | 5.62 | 5.59 | 5.50 |
| Particle size (μm) | 1 Cycle | 3.89 ± 3.33 | 3.88 ± 3.21 | 3.86 ± 2.81 | 3.92 ± 3.20 | 3.82 ± 2.46 |
| | 2 Cycle | 3.94 ± 2.87 | 3.98 ± 2.97 | 3.97 ± 3.09 | 4.05 ± 3.25 | 3.99 ± 2.87 |
| | 3 Cycle | 4.02 ± 3.25 | 4.08 ± 3.83 | 4.12 ± 3.15 | 4.06 ± 3.09 | 4.07 ± 3.69 |
| | 4 Cycle | 4.21 ± 3.07 | 4.27 ± 3.01 | 4.26 ± 3.29 | 4.25 ± 2.78 | 4.26 ± 2.86 |
| | 5 Cycle | 4.31 ± 3.04 | 4.29 ± 2.85 | 4.28 ± 2.99 | 4.32 ± 3.32 | 4.30 ± 3.30 |

TABLE 11

Observations for Freeze-Thaw cycles of RT (3-day) and 2-8° C. (3-day)

| | | Formulation ID | | | | |
|---|---|---|---|---|---|---|
| | | DS-54 | DS-55 | DS-56 | DS-57 | DS-58 |
| | | Polymer | | | | |
| | | Methocel F50 3% w/v | Methocel E50 3% w/v | Methocel A4MP 0.5% w/v | MC, 400 cps 0.5% w/v | Klucel JF 3% w/v |
| | | Observations after Thawing-freeze Cycle: storage at RT for 3 days followed by at 2-8° C. for 3 days | | | | |
| Sedimentation Coefficient | 1 Cycle | 0.97 | 0.97 | 0.53 | 0.96 | 0.62 |
| | 2 Cycle | 0.96 | 0.96 | 0.55 | 0.24 | 0.77 |
| | 3 Cycle | 0.96 | 0.96 | 0.53 | 0.23 | 0.70 |
| | 4 Cycle | 0.96 | 0.96 | 0.54 | 0.53 | 0.78 |
| | 5 Cycle | 0.94 | 0.90 | 0.52 | 0.51 | 0.56 |
| Appearance (visual) | 1 Cycle | sedimentation two layers | sedimentation two layers | clear supernatant, a thin opaque flocculation layer between clear supernatant and sedimentation, sedimentation two layers | sedimentation two layers | opaque supernatant with floccules |
| | 2 Cycle | sedimentation two layers | sedimentation two layers | clear supernatant | sedimentation two layers, milky supernatant with floccules | opaque supernatant with floccules |
| | 3 Cycle | sedimentation two layers | sedimentation two layers | clear supernatant | An opaque supernatant on top, a thick milky flocculation layer between opaque supernatant and sedimentation, sedimentation two layers | opaque supernatant with floccules |
| | 4 Cycle | sedimentation two layers | sedimentation two layers | clear supernatant | clear supernatant, sedimentation two layers | opaque supernatant with floccules |
| | 5 Cycle | sedimentation two layers | clear to opaque supernatant, sedimentation two layers | clear supernatant | clear supernatant, sedimentation two layers | A thin clear supernatant on top, a thick opaque flocculation layer between clear supernatant and sedimentation |
| Redispersibility | 1 Cycle | redispersible | redispersible | redispersible; sedimentation occurs at 10 min after shaking | redispersible | redispersible |
| | 2 Cycle | redispersible | redispersible | redispersible; sedimentation occurs at 10 min after shaking | redispersible | redispersible |
| | 3 Cycle | redispersible | redispersible | redispersible; sedimentation occurs at 10 min after shaking | redispersible | redispersible |
| | 4 Cycle | redispersible | redispersible | redispersible; sedimentation occurs at 10 min after shaking, sedimentation appears loose and curdy | redispersible; sedimentation occurs at 30 min after shaking | redispersible |
| | 5 Cycle | redispersible | redispersible | redispersible; sedimentation occurs at 10 min after shaking, sedimentation appears loose and curdy | redispersible; sedimentation occurs at 10 min after shaking | redispersible |
| pH | 1 Cycle | 5.70 | 5.72 | 5.71 | 5.70 | 5.63 |
| | 2 Cycle | 5.67 | 5.68 | 5.67 | 5.73 | 5.61 |
| | 3 Cycle | 5.61 | 5.58 | 5.70 | 5.65 | 5.53 |
| | 4 Cycle | 5.57 | 5.58 | 5.62 | 5.64 | 5.55 |
| | 5 Cycle | 5.62 | 5.58 | 5.57 | 5.62 | 5.47 |

TABLE 11-continued

Observations for Freeze-Thaw cycles of RT (3-day) and 2-8° C. (3-day)

| | | Formulation ID | | | | |
|---|---|---|---|---|---|---|
| | | DS-54 | DS-55 | DS-56 | DS-57 | DS-58 |
| | | | | Polymer | | |
| | | Methocel F50 3% w/v | Methocel E50 3% w/v | Methocel A4MP 0.5% w/v | MC, 400 cps 0.5% w/v | Klucel JF 3% w/v |
| | | Observations after Thawing-freeze Cycle: storage at RT for 3 days followed by at 2-8° C. for 3 days | | | | |
| Particle size (μm) | 1 Cycle | 4.10 ± 2.63 | 4.09 ± 3.04 | 3.96 ± 2.41 | 4.09 ± 3.14 | 4.08 ± 2.76 |
| | 2 Cycle | 4.31 ± 3.66 | 4.37 ± 3.29 | 4.13 ± 2.77 | 4.22 ± 2.45 | 4.16 ± 2.58 |
| | 3 Cycle | 4.36 ± 3.43 | 4.37 ± 3.01 | 4.36 ± 3.20 | 4.41 ± 3.42 | 4.41 ± 3.11 |
| | 4 Cycle | 4.44 ± 3.31 | 4.38 ± 3.19 | 4.47 ± 3.05 | 4.48 ± 3.23 | 4.46 ± 3.00 |
| | 5 Cycle | 4.47 ± 2.87 | 4.49 ± 2.98 | 4.47 ± 3.28 | 4.50 ± 3.06 | 4.48 ± 2.92 |

It was observed that suspensions with 3% Methocel F50 or 3% Methocel E50 as suspending agents showed good stability for 14 days and after 5 freeze-thawing cycles, but slow reconstitution rates were observed when dispersing blends in purified water.

Suspensions using 0.5% Methocel A4MP as suspending agent showed loose and curdy sedimentation during stability study, indicating incompatibility.

However, 0.5% Methylcellulose (400 cps) or 3% Klucel JF Pharm as suspending agents showed good reconstitution rate and acceptable stability and therefore could be used as alternative suspending agents for the target formulation.

Example 6: Optimization of Suspending Agent Concentration for Dispersibility Study (Using Simethicone Granular MED-342)

According to the observations of DS-54 to DS-58, concentrations of Methocel F50, Methocel E50, and KlucelJF Pharm were decreased for better dispersibility, while concentration of Methylcellulose 400 cps was increased for a balance between dispersibility and viscosity. Simethicone in the formulations was changed to the granular solid form (MED-342), which simplifies the process by avoiding adsorbing liquid simethicone on lactose. The compositions are shown in Table 12.

TABLE 12

Composition of blends using Simethicone granular solid

| | | Quantity per unit (mg) | | | | | | |
|---|---|---|---|---|---|---|---|---|
| S.# | Ingredients | DS-54 | DS-55 | DS-57 | DS-58 | DS-63 | DS-64 | DS-65 |
| 1 | Tecovirimat Granules | 346.50 | 346.50 | 346.50 | 346.50 | 346.50 | 346.50 | 346.50 |
| 2 | Sucralose, NF | 10.00 | 10.00 | 10.00 | 10.00 | 10.00 | 10.00 | 10.00 |
| 3 | Simethicone granular solid, USP (MED-342) | 10.00 | 10.00 | 10.00 | 10.00 | 10.00 | 10.00 | 10.00 |
| 4 | Lactose Monohydrate, NF (SuperTab 11SD) | 483.50 | 483.50 | 608.50 | 483.50 | 508.50 | 508.50 | 583.50 |
| 5 | Hypromellose (Methocel F 50) | 150.00 | — | — | — | 125.00 | — | — |
| | Hypromellose (Methocel E 50) | — | 150.00 | — | — | — | 125.00 | — |
| | Methyl Cellulose, 400 cps, USP | — | — | 25.00 | — | — | — | 50.00 |
| | Hydroxypropyl cellulose (Klucel JF Pharm), NF | — | — | — | 150.00 | — | — | — |
| 6 | Purified water, USP, Q.S. to 5 mL | — | — | — | — | — | — | — |
| | Total | 1000.00 | 1000.00 | 1000.00 | 1000.00 | 1000.00 | 1000.00 | 1000.00 |

| | | Quantity per unit (mg) | | | | |
|---|---|---|---|---|---|---|
| S.# | Ingredients | DS-66 | DS-67 | DS-68 | DS-69 | DS-70 |
| 1 | Tecovirimat Granules | 346.50 | 346.50 | 346.50 | 346.50 | 346.50 |
| 2 | Sucralose, NF | 10.00 | 10.00 | 10.00 | 10.00 | 10.00 |
| 3 | Simethicone granular solid, USP (MED-342) | 10.00 | 10.00 | 10.00 | 10.00 | 10.00 |
| 4 | Lactose Monohydrate, NF (SuperTab 11SD) | 508.50 | 533.50 | 533.50 | 558.50 | 533.50 |

TABLE 12-continued

Composition of blends using Simethicone granular solid

| S.# | Component | | | | | |
|---|---|---|---|---|---|---|
| 5 | Hypromellose (Methocel F 50) | — | 100.00 | — | — | — |
| | Hypromellose (Methocel E 50) | — | — | 100.00 | — | — |
| | Methyl Cellulose, 400 cps, USP | — | — | — | 75.00 | — |
| | Hydroxypropyl cellulose (Klucel JF Pharm), NF | 125.00 | — | — | — | 100.00 |
| 6 | Purified water, USP, Q.S. to 5 mL | — | — | — | — | — |
| | Total | 1000.00 | 1000.00 | 1000.00 | 1000.00 | 1000.00 |

In general, the formulation procedures include:
1. blending of Tecovirimat granules and simethicone granular solid (VED-342), then passing through Quadro Comil equipped with 2B039R03125173*(991) screen;
2. weighing of quantity equivalent to 40 g of Simethicone-Tecovirimat granules blend and mixing geometrically with other components;
3. passing again of the blend through Quadro Comil using 2B039R03125173*(991) screen and
4. dispersing of 1 dose in purified water to make Q.S. to 5 mL, followed by evaluation of dispersibility and dissolution (Table 13).

The % ST-246 is shown in FIG. 1.

It was observed that when concentrations of Methocel F50 and Methocel E50 decreased to 2.0% w/v (DS-67 and DS-68), there were still chunks remaining after shaking manually. Hydration rates of these two polymers are fast such that the gel layers developed inhibit the wetting of inside materials, leading to fish eyes and bad dispersibility. Concentration of 0.5-1.0% w/v Methylcellulose 400 cps and 2.0-2.5% w/v Klucel JF Pharm can reach a balance between good dispersibility and viscosity.

TABLE 13

Observation of reconstitution and dissolution

| S.# | Properties | | DS-54 | | DS-55 | | DS-57 | | DS-58 | |
|---|---|---|---|---|---|---|---|---|---|---|
| 1 | Chunks remaining at bottom after shaking | | Big chunks | | Big chunks | | None | | Very small chunks | |

| | | Time (mins) | % Released | SD | % Released | SD | % Released | SD | % Released | SD |
|---|---|---|---|---|---|---|---|---|---|---|
| 2 | Dissolution (n = 3) | 5 | 78.5 | 4.5 | 85.3 | 2.3 | 83.6 | 2.6 | 72.7 | 1.5 |
| | | 10 | 76.6 | 5.7 | 83.7 | 1.9 | 82.4 | 1.9 | 81.8 | 1.5 |
| | | 15 | 76.0 | 6.7 | 84.2 | 1.6 | 82.5 | 1.1 | 83.2 | 1.6 |
| | | 30 | 76.1 | 6.3 | 84.2 | 2.0 | 84.0 | 0.2 | 85.8 | 0.8 |
| | | 45 | 76.1 | 6.2 | 84.0 | 2.0 | 83.7 | 1.1 | 86.7 | 2.3 |

| S.# | Properties | DS-63 | DS-64 | DS-65 | DS-66 | DS-67 | DS-68 | DS-69 | DS-70 |
|---|---|---|---|---|---|---|---|---|---|
| 1 | Chunks remaining at bottom after shaking | Medium chunks | Medium chunks | Small chunks | None | Small chunks | Small chunks | Small chunks | None |

Example 7: Evaluation of a Combination of Suspending Agents

Combinations of suspending agents were used for dissolution study. Compositions are given in Table 14. The Target formulation using Avicel CL-611 as a suspending agent exhibits floating in the form of lumps in dissolution test.

TABLE 14

Composition of solid blends using combination of suspending agents

| | | Quantity per unit (mg) | | | |
|---|---|---|---|---|---|
| S. # | Ingredients | Prototype 1 (DS-59) | Prototype 2 (DS-60) | Prototype 3 (DS-61) | Prototype 4 (DS-62) |
| 1 | Tecovirimat Granules | 346.50 | 346.50 | 346.50 | 346.50 |
| 2 | Simethicone granular solid, USP (MED-342) | 10.00 | 10.00 | 10.00 | 10.00 |
| 3 | Lactose Monohydrate, NF (SuperTab 11SD) | 328.50 | 348.50 | 373.50 | 370.50 |
| 4 | Avicel CL-611, NF | 50.00 | 25.00 | — | — |
| 5 | Methyl Cellulose, 400 cps, USP | 15.00 | 20.00 | 15.00 | 20.00 |
| 6 | Xantural 75 | — | — | 5.00 | 3.00 |
| 7 | Purified water, USP, Q.S. to 5 mL | — | — | — | — |
| | Total | 750.00 | 750.00 | 750.00 | 750.00 |

The formulation procedures was as follows;
1. blending of Tecovirimat granules and Simethicone granular solid (MED-342), then passing through Quadro Comil equipped with 2B039R03125173*(991) screen;
2. weighing of the quantity equivalent to 30 units of Simethicone-Tecovirimat blend and then geometric mixing with other components; shaking and mixing of blend in a zip-lock bag;
3. dispersing of 1 dose in purified water to make Q.S. to 5 mL for dissolution test (Table 15).

TABLE 15

Dissolution of suspensions using combination of suspending agents

| | | Formulation ID | | | |
|---|---|---|---|---|---|
| S. # | Properties | Prototype 1 (DS-59) | Prototype 2 (DS-60) | Prototype 3 (DS-61) | Prototype 4 (DS-62) |
| 1 | Dispersibility | Small chunks remaining after shaking | Small chunks remaining after shaking | Small chunks remaining after shaking | Small chunks remaining after shaking |
| 2 | Viscosity | Good viscosity | Watery | Watery | Watery |
| 3 | Dissolution | Instant dispersion with formation of coarse particulates | Instant dispersion with formation of fine particulates | Gel clumps | Gel clumps |

Example 8: Optimizing Anti-foaming Agent and Viscosity

The suspensions were optimized for defoaming and viscosity of suspension by changing the level of simethicone solid granular and methylcellulose 400 cps in reference formulation DS-60. The methylcellulose 400 cps was replaced with Klucel JF Pharm and formulated to test the effect on foaminess. The compositions are given in Table 16.

TABLE 16

Composition of DS-60A to DS-60E and DS-71

| | | Quantity per unit (mg) | | | | | |
|---|---|---|---|---|---|---|---|
| S.# | Ingredients | DS-60A | DS-60B | DS-60C | DS-60D | DS-60E | DS-71 |
| 1 | Tecovirimat Granules | 346.50 | 346.50 | 346.50 | 346.50 | 346.50 | 346.50 |
| 2 | Simethicone granular solid, USP (MED-342) | 16.67 | 25.00 | 16.67 | 16.67 | 16.67 | 16.67 |
| 3 | Lactose Monohydrate, NF (SuperTab 11SD) | 341.83 | 333.50 | 336.83 | 331.83 | 331.83 | 341.83 |
| 4 | Avicel CL-611, NF | 25.00 | 25.00 | 25.00 | 25.00 | 25.00 | 25.00 |
| | Methyl Cellulose, 400 cps, USP | 20.00 | 20.00 | 25.00 | 30.00 | 37.50 | — |
| | Hydroxypropyl cellulose (Klucel JF Pharm), NF | — | — | — | — | — | 20.00 |
| 5 | Purified water, USP, Q.S. to 5 mL | — | — | — | — | — | — |
| | Total | 750.00 | 750.00 | 750.00 | 750.00 | 757.50 | 750.00 |

The formulation procedures included
1. geometric mixing of quantity equivalent to 30 units of lactose monohydrate and simethicone (MED-342), then geometric mixing with other components;
2. passing of the blend through Quadro Comil equipped with 2B039R03125173*(991) screen and
3. dispersing of 1 dose in purified water to make Q.S. to 5 mL to test foaminess and viscosity (Table 17).

TABLE 17

Observation of foaminess and viscosity of DS-60A to DS-60E and DS-71

| | | Formulation ID | | | | | |
|---|---|---|---|---|---|---|---|
| S.# | Properties | DS-60A | DS-60B | DS-60C | DS-60D | DS-60E | DS-71 |
| 1 | Dispersibility | Easy to disperse, no chunks remaining | Easy to disperse, no chunks remaining | Easy to disperse, no chunks remaining | Easy to disperse, no chunks remaining | Small chunks remaining after shaking | Easy to disperse, no chunks remaining |
| 2 | Foaminess | Less foam than DS-60 | Decreased foam | Decreased foam | Decreased foam | Decreased foam | Less foam than DS-60A |
| 3 | Viscosity | Watery | Watery | Watery | Watery | Good viscosity | Watery |

It was observed that the level of 16.67-25 mg per unit of Simethicone (MED-342) attains a good anti-foaming effect. The replacement of KlucelJF Pharm with Methylcellulose 400 cps also decreases foaminess. Good viscosity in suspension was observed when Methylcellulose 400 cps level reached 0.75% w/v.

Example 9: Methylcellulose (400 cps and 15 cps) Combination as Suspending Agents The level of Methylcellulose 15 cps was adjusted for better dispersibility. Compositions are given in Table 18.

TABLE 18

Composition of DS-72 to DS-74

| | | Quantity per unit (mg) | | |
|---|---|---|---|---|
| S. # | Ingredients | DS-72 | DS-73 | DS-74 |
| 1 | Tecovirimat Granules | 346.50 | 346.50 | 346.50 |
| 2 | Simethicone granular solid, USP (MED-342) | 16.67 | 16.67 | 16.67 |
| 3 | Lactose Monohydrate, NF (SuperTab 11SD) | 349.33 | 349.33 | 349.33 |
| 4 | Methyl Cellulose, 400 cps, USP | 37.50 | 33.50 | 30.00 |
| | Methyl Cellulose, 15 cps, USP | — | 4.00 | 7.50 |
| 5 | Purified water, USP, Q.S. to 5 mL | — | — | — |
| | Total | 750.00 | 750.00 | 750.00 |

The formulation procedure included
1. geometric mixing of Tecovirimat granules, lactose monohydrate and Simethicone (MED-342) and passing of blend through Quadro Comil equipped with 2B039R03125173*(991) screen;

2. weighing of quantity equivalent to 10 units of blend and then geometric mixing with polymer(s) and
3. dispersing of 1 dose in purified water to make Q.S. to 5 mL to test dispersibility.

It was observed that all three formulations were easy to disperse with no chunks remaining after shaking. With decreased level of Methylcellulose 400 cps in formulation, suspension was more watery, suggesting it's better to keep Methylcellulose 400 cps more than 0.75% w/v.

Example 10: Optimizing levels of Methylcellulose 15 cps and Simethicone in Methylcellulose Combination for Rapid Hydration Methylcellulose 400 cps concentration was kept as 1.0% w/v, and the amount of Methylcellulose 15 cps was adjusted for better dispersibility/hydration and the level of Simethicone (MED-342) adjusted to investigate the anti-foaming effect. Compositions are given in Table 19. Total blends were decreased to 500 mg per unit.

TABLE 19

Composition of DS-75 to DS-82

| S.# | Ingredients | Quantity per unit (mg) | | | | | | | |
|---|---|---|---|---|---|---|---|---|---|
| | | DS-75 | DS-76 | DS-77 | DS-78 | DS-79 | DS-80 | DS-81 | DS-82 |
| 1 | Tecovirimat Granules | 346.50 | 346.50 | 346.50 | 346.50 | 346.50 | 346.50 | 346.50 | 346.50 |
| 2 | Sucralose, NF | 10.00 | 10.00 | 10.00 | 10.00 | 10.00 | 10.00 | 10.00 | 10.00 |
| 3 | Simethicone granular solid, USP (MED-342) | 20.00 | 20.00 | 20.00 | 20.00 | 20.00 | 25.00 | 30.00 | 35.00 |
| 4 | Lactose Monohydrate, NF (SuperTab 11SD) | 43.50 | 63.50 | 53.50 | 43.50 | 58.50 | 53.50 | 53.50 | 53.50 |
| 5 | Methyl Cellulose, 400 cps, USP | 50.00 | 50.00 | 50.00 | 50.00 | 50.00 | 50.00 | 50.00 | 50.00 |
| | Methyl Cellulose, 15 cps, USP | — | 5.00 | 15.00 | 25.00 | 10.00 | 15.00 | 15.00 | 15.00 |
| 6 | Strawberry flavor, #133.16296 | 5.00 | 5.00 | 5.00 | 5.00 | 5.00 | 5.00 | 5.00 | 5.00 |
| 7 | Purified water, USP, Q.S. to 5 mL | — | — | — | — | — | — | — | — |
| | Total | 475.00 | 500.00 | 500.00 | 500.00 | 500.00 | 505.00 | 510.00 | 515.00 |

The formulation procedure was as follows;
1. geometric mixing of quantity equivalent to 100 units of Tecovirimat granules, sucralose, lactose monohydrate, Simethicone (MED-342) and Methylcellulose 400 cps in DS-75, then passing of blend through Quadro Comil equipped with 2B039R03125173*(991) screen;
2. for DS-75, weigh quantity equivalent to 50 units of blend and then geometric mixing with strawberry flavor;
3. for DS-77, weigh quantity equivalent to 30 units of blend and then geometric mixing with strawberry flavor, Methylcellulose 15 cps, and lactose monohydrate;
4. for DS-76 to DS-79, weigh quantity equivalent to 10 units of DS-75 and then geometric mixing with other components;
5. for DS-80 to DS-82, weigh quantity equivalent to 5 units of DS-77 and then geometric mixing with other components and
6. dispersing of 1 dose in purified water to make Q.S. to 5 mL to test dispersibility, foaminess and sedimentation (Table 20).

TABLE 20

Observation of suspensions of DS-75 to DS-82

| S.# | Properties | | Formulation ID | | | | | | | |
|---|---|---|---|---|---|---|---|---|---|---|
| | | | DS-75 | DS-76 | DS-77 | DS-78 | DS-79 | DS-80 | DS-81 | DS-82 |
| 1 | Dispersibility (chunks remaining at bottom after shaking) | | small chunks | very tiny chunk | no chunks | no chunks | no chunks | big chunks | big chunks | big chunks |
| 2 | Settlement/ foaminess | T = 0 | No sedimentation. Foam is similar in all formulations | | | | | | | |
| | | T = 30 min | No sedimentation. Individual bubbles are smaller in DS-80, DS-81, DS-82 | | | | | | | |
| | | T = 1 hr | No sedimentation. Individual bubbles are smaller in DS-80, DS-81, DS-82. Quantity of foam is less in DS-80, DS-81, DS-82 | | | | | | | |
| | | T = 2 hr | No sedimentation. A very thin layer of foam in DS-80 and DS-81. No foam in DS-82. | | | | | | | |

TABLE 20-continued

Observation of suspensions of DS-75 to DS-82

| S.# | Properties | DS-75 | DS-76 | DS-77 | DS-78 | DS-79 | DS-80 | DS-81 | DS-82 |
|---|---|---|---|---|---|---|---|---|---|
| | T = 17 hr Foaminess | No foam in all formulations | | | | | | | |
| | Sedimentation coefficient | 0.82 | 0.84 | 0.86 | 0.86 | 0.86 | 0.86 | 0.82 | 0.82 |
| | Second layer (mm) | 4 | 4 | 4 | 4 | 4 | 4 | 5 | 5 |

It was observed that ethylcellulose 15 cps level of 10-25 mg per Tecovirimat dosage unit can lead to good dispersibility/hydration. There was no significant difference in foaminess of suspensions initially and after 17 hours of reconstitution informations with Simethicone level of 20-35 mg per unit. The big chunks in formulation with 25-35 mg Simethicone per unit may be caused by Simethicone agglomeration, suggesting that it is advantageous to keep Simethicone as 20 mg per unit. All formulations showed good viscosity with 100 w/v Methylcellulose 400 cps.

Example 11: Scale-Up of the Optimized Compositions

Scale-up batches using methylcellulose (400 cps) and Klucel JXF Pharm as suspending agents were prepared and evaluated. Compositions are given in Table 21.

The batch size of each composition was 0.500 kg. In general, the formulation procedure involved the following steps:

1. Sieving of the Tecovirimat granules and granular Simethicone through Quadro Comil equipped with 2B039R03125173*(991) screen.
2. Sieving of the Tecovirimat granulate and granular Simethicone through a #20 screen.
3. Sieving of lactose through a #20 screen, then addition of Flavor on lactose with geometric mixing using spatula.
4. Sieving of polymer and sucralose through a #40 screen.
5. Blending of the Tecovirimat-Simethicone blend and other extra-granular components in the V-blender for 15 minutes.

TABLE 21

Composition of Scale-Up batches

| S. # | Ingredients | Batch: FSIG-20140826-1 (DS-75) | Batch: FSIG-20140826-2 (DS-77) | Batch: FSIG-20141216-1 (DS-83) | Batch: FSIG-20141216-2 (DS-84) |
|---|---|---|---|---|---|
| | | Quantity per unit (mg) | | | |
| | | Goal: Using Methylcellulose (400 cps and 15 cps) as a suspending agent (500 g scale). | | Goal: Using Hydroxypropyl Cellulose (Klucel JXF Pharm) as a suspending agent (500 g scale). | |
| 1 | Tecovirimat Granulate | 346.49 | 346.49 | 346.50 | 346.50 |
| 2 | Lactose monohydrate, NF (SuperTab 11SD) | 66.01 | 51.01 | 93.00 | — |
| 3 | Methylcellulose, 400 cps, USP | 50.00 | 50.00 | — | — |
| 4 | Methylcellulose, 15 cps, USP | — | 15.00 | — | — |
| 5 | Hydroxylpropyl Cellulose (Klucel JXF Pham) | — | — | 125.00 | 118.00 |
| 6 | Sucralose, NF | 10.00 | 10.00 | 10.00 | 10.00 |
| 7 | Strawberry flavor, #133.16296 | 5.00 | 5.00 | — | — |
| 8 | Black cherry Nat type flavor | — | — | 3.00 | 3.00 |
| 9 | Simethicone Granular Solid (MED-342), USP | 20.00 | 20.00 | 20.00 | 20.00 |
| 10 | Magnesium stearate, NF | 2.50 | 2.50 | 2.50 | 2.50 |
| | Total weight (mg) | 500.00 | 500.00 | 600.00 | 500.00 |

6. Passing of magnesium stearate through a #40 screen, then addition as a lubricant to above milled blend and lubricate for 5 minutes.
7. Evaluation of the physicochemical properties of blend (Table 22).
8. Transfer of 10 doses of blend to a 100 cc glass bottle. Add water Q. S. to 50 mL. Shake well to mix the content. Evaluate the physicochemical properties of suspension (Table 21).
9. Packing of 20 doses of blend in Stick pack PAKVF2.5M Fin seal pouches (part #25M0275FS06) Size 2.5 inch×6 inch. Heat-seal properly. Prepare 15-20 pouches for stability/dissolution study (Table 24).

TABLE 22

Physicochemical properties of blends of scale-up batches

| S# | Property | Batch: FSIG-20140826-1 | Batch: FSIG-20140826-2 | Batch: FSIG-20141216-1 | Batch: FSIG-20141216-2 |
|---|---|---|---|---|---|
| 1 | Appearance | White powder | White powder | White powder | White powder |
| 2 | Flow of Lubricated Blend (Flodex Orifice mm) | 24 | 26 | 26 | 28 |
| 3 | Bulk Density (g/cc) | 0.541 | 0.520 | 0.505 | 0.468 |
|   | Tap Density (g/cc) | 0.693 | 0.667 | 0.640 | 0.607 |
|   | Compressibility Index (%) | 21.9 | 22.0 | 21.1 | 22.9 |
| 4 | Granules Retained on Sieve # 20 (opening size 0.850 mm) (%) | 0.01 | 0.01 | 0.02 | 0.02 |
|   | Granules Retained on Sieve # 30 (opening size 0.600 mm) (%) | 1.85 | 2.22 | 3.29 | 3.52 |
|   | Granules Retained on Sieve # 40 (opening size 0.425 mm) (%) | 9.37 | 10.46 | 8.60 | 10.61 |
|   | Granules Retained on Sieve # 50 (opening size 0.300 mm) (%) | 8.64 | 9.72 | 10.72 | 12.48 |
|   | Granules Retained on Sieve # 60 (opening size 0.250 mm) (%) | 4.12 | 4.36 | 4.06 | 5.24 |
|   | Granules Retained on Sieve # 80 (opening size 0.180 mm) (%) | 10.53 | 11.84 | 12.33 | 12.29 |
|   | Retained on Pan (size <0.180 mm) (%) | 65.47 | 61.40 | 60.96 | 55.84 |
|   | Mean Size (mm) | 0.106 | 0.119 | 0.121 | 0.139 |

TABLE 23

Physicochemical properties of suspensions of scale-up batches

| S# | Property | Batch: FSIG-20140826-1 | | | Batch: FSIG-20140826-2 | | |
|---|---|---|---|---|---|---|---|
| 1 | Reconstitution | After manual shaking, fish eyes were observed at 4 positions at bottom of bottle. | | | After manual shaking, fish eye was observed at only one position at bottom of bottle. | | |
| 2 | Appearance after reconstitution | White dispersion | | | White dispersion | | |
| 3 | pH of suspension | 5.98 | | | 6.00 | | |
| 4 | Microscopic observation | Particle size 3.16 ± 2.37 μm. No agglomeration observed. | | | Particle size 3.20 ± 2.63 μm. No agglomeration observed. | | |
| 5 | Physical stability | No phase separation or agglomeration. | | | No phase separation or agglomeration. | | |
| 6 | Forced settling and redispersibility | Redispersible | | | Redispersible | | |
| 7 | Observation of sedimentation | 10 min | 30 min | 24 hr | 10 min | 30 min | 24 hr |
| | | At 25° C. | | | | | |
| | Sedimentation coefficient | 1.00 | 1.00 | 1.00 | 1.00 | 1.00 | 1.00 |
| | Separation | None | None | Second layer (29% height) | None | None | Second layer (29% height) |
| | Redispersibility | Redispersible | Redispersible | Redispersible | Redispersible | Redispersible | Redispersible |
| | | At 5° C. | | | | | |
| | Sedimentation coefficient | 1.00 | 1.00 | 1.00 | 1.00 | 1.00 | 1.00 |
| | Separation | None | None | Second layer (23% height) | None | None | Second layer (20% height) |
| | Redispersibility | Redispersible | Redispersible | Redispersible | Redispersible | Redispersible | Redispersible |
| S# | Property | Batch: FSIG-20141216-1 | | | Batch: FSIG-20141216-2 | | |
| 1 | Reconstitution | After manual shaking, fish eyes were observed at 2 positions at bottom of bottle. | | | After manual shaking, no fish eye was observed, disperse very well. | | |

TABLE 23-continued

Physicochemical properties of suspensions of scale-up batches

| | | | | | | | |
|---|---|---|---|---|---|---|---|
| 2 | Appearance after reconstitution | White dispersion | | | White dispersion | | |
| 3 | pH of suspension | 5.99 | | | 6.15 | | |
| 4 | Microscopic observation | Particle size 3.04 ± 2.11 μm. No agglomeration observed. | | | Particle size 3.13 ± 2.53 μm. No agglomeration observed. | | |
| 5 | Physical stability | No phase separation. Small agglomerations are observed when pouring out. | | | No phase separation. Small agglomerations are observed when pouring out. | | |
| 6 | Forced settling and redispersibility | Redispersible | | | Redispersible | | |
| 7 | Observation of sedimentation | 10 min | 30 min | 24 hr | 10 min | 30 min | 24 hr |

At 25° C.

| | | | | | | |
|---|---|---|---|---|---|---|
| Sedimentation coefficient | 1.00 | 1.00 | 0.56 | 1.00 | 1.00 | 0.58 |
| Separation | None | None | None | None | None | None |
| Redispersibility | Redispersible | Redispersible | Redispersible | Redispersible | Redispersible | Redispersible |

At 5° C.

| | | | | | | |
|---|---|---|---|---|---|---|
| Sedimentation coefficient | 1.00 | 1.00 | 0.89 | 1.00 | 1.00 | 0.88 |
| Separation | None | None | None | None | None | None |
| Redispersibility | Redispersible | Redispersible | Redispersible | Redispersible | Redispersible | Redispersible |

TABLE 24

Stability and dissolution of scale-up batches

| | Property | Batch: FSIG-20140826-1 (DS75) | | Batch: FSIG-20140826-2 (DS77) | | Batch: FSIG-20141216-1 (DS83) | | Batch: FSIG-20141216-2 (DS84) | |
|---|---|---|---|---|---|---|---|---|---|
| S# | Time (mins) | % Released | SD | % Released | SD | % Released | SD | % Released | SD |
| 1 | Dissolution (n = 6) 5 | 88.6 | 1.3 | 88.4 | 1.5 | 84.2 | 6.7 | 92.4 | 4.2 |
| | 10 | 90.2 | 1.7 | 92.3 | 1.5 | 93.9 | 4.4 | 97.6 | 1.7 |
| | 15 | 89.4 | 1.5 | 90.5 | 2.8 | 94.1 | 2.0 | 99.3 | 1.7 |
| | 30 | 90.4 | 1.3 | 90.2 | 1.4 | 96.9 | 0.9 | 101.4 | 2.2 |
| | 45 | 93.6 | 2.5 | 90.7 | 1.5 | 97.1 | 1.0 | 100.3 | 0.7 |

Figure 2:
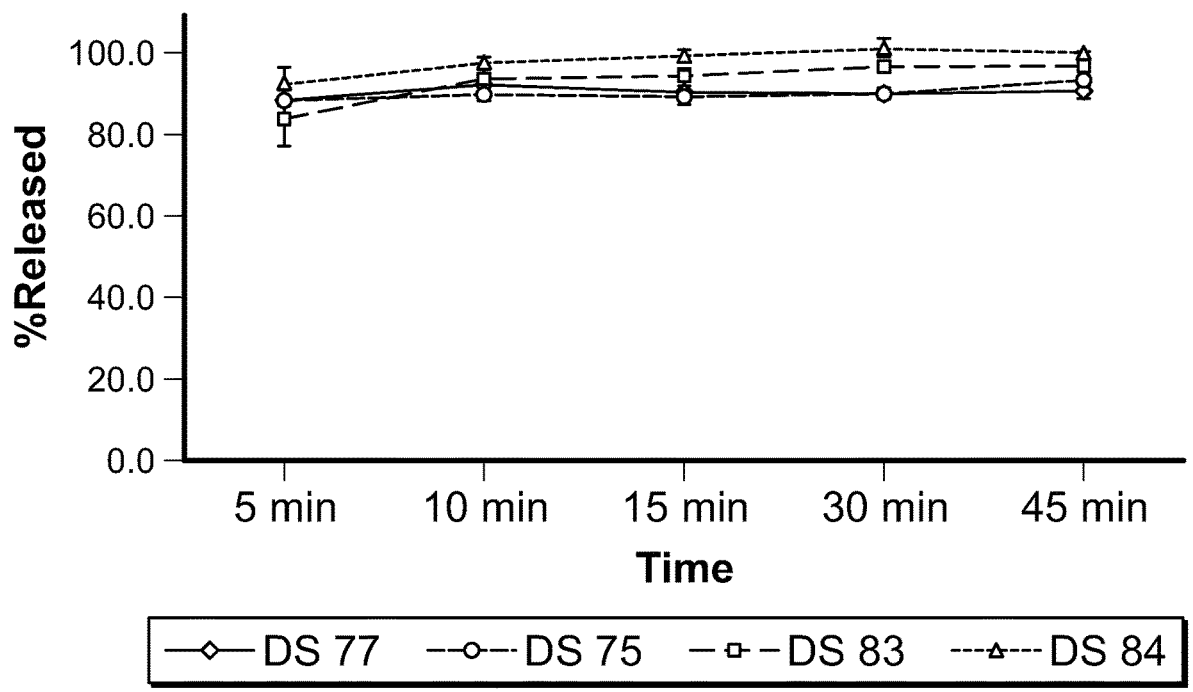

The % ST-246 released is shown in FIG. 2.

Example 12: Effect of Particle Sizes of API on Formulation Properties

To study the effect of particle sizes of API on formulation performance properties, such as dissolution, use API of different particle sizes for granulation process. Compositions are given in Table 25.

TABLE 25

Composition of DS-85 to DS-87 using API of different particle sizes

Quantity per unit (mg)
Goal: Using API of different particle sizes for granulation process
(288.6 g scale).
Ref. DS-77
(Batch # FSIG-20140826-2)

| S. # | Ingredients | Batch: FSIG-20150120-1 (DS-85) | Batch: FSIG-20150120-2 (DS-86) | Batch: FSIG-20150120-3 (DS-87) |
|---|---|---|---|---|
| | Intragranular Ingredients: | | | |
| 1 | Tecovirimat monohydrate, micronized | 209.0 using API Lot# SG-10C12-T1039 (Trial #2, d90 = 21.51 μm) | 209.0 using API Lot# SG-10C12-T1039 (Trial #3, d90 = 38.74 μm) | 209.0 using API Lot# SG-10C12-T1039 (Trial #4, d90 = 81.53 μm) |

TABLE 25-continued

Composition of DS-85 to DS-87 using API of different particle sizes

Quantity per unit (mg)
Goal: Using API of different particle sizes for granulation process
(288.6 g scale).
Ref. DS-77
(Batch # FSIG-20140826-2)

| S. # | Ingredients | Batch: FSIG-20150120-1 (DS-85) | Batch: FSIG-20150120-2 (DS-86) | Batch: FSIG-20150120-3 (DS-87) |
|---|---|---|---|---|
| 2 | Colloidal silicon dioxide, NF (Cabosil M5P) | 1.95 | 1.95 | 1.95 |
| 3 | Croscarmellose sodium, NF (AcDiSol) | 31.32 | 31.32 | 31.32 |
| 4 | Lactose monohydrate, NF (SuperTab 11SD) | 33.15 | 33.15 | 33.15 |
| 5 | Microcrystalline cellulose, NF (Avicel PH 101) | 49.62 | 49.62 | 49.62 |
| | Intragranular Ingredients Total | 325.04 | 325.04 | 325.04 |
| | Granulating Fluid: | | | |
| 6 | Hypromellose, USP (Methocel E3 LV Prem.) | 13.65 | 13.65 | 13.65 |
| 7 | Sodium lauryl sulfate, NF | 7.80 | 7.80 | 7.80 |
| 8 | Purified water, USP* | 170.1 | 170.1 | 170.1 |
| | Granulating Fluid Solids Total | 21.45 | 21.45 | 21.45 |
| | Granulate Solids | 346.49 | 346.49 | 346.49 |
| | Extragranular Ingredients: | | | |
| 9 | Lactose monohydrate, NF (SuperTab 11SD) | 51.01 | 51.01 | 51.01 |
| 10 | Methylcellulose, 400 cps, USP | 50.0 | 50.0 | 50.0 |
| 11 | Methylcellulose, 15 cps, USP | 15.0 | 15.0 | 15.0 |
| 12 | Sucralose, NF | 10.0 | 10.0 | 10.0 |
| 13 | Strawberry flavor, #133.16296 | 5.0 | 5.0 | 5.0 |
| 14 | Simethicone Granular Solid (MED-342), USP | 20.0 | 20.0 | 20.0 |
| 15 | Magnesium stearate, NF | 2.5 | 2.5 | 2.5 |
| | Powder for Reconstitution Blend Total | 500.00 | 500.00 | 500.00 |

*Removed during the drying process.

The batch size of each composition was 0.2886 Kg. Detailed experimental procedures and results of each trial formulation were recorded in the executed batch records. In general, the formulation procedure involved the following steps:

1. Passing of intragranular components through a #20 screen.
2. Mixing of intragranular components containing diluents, disintegrant, in GMX-High Shear Granulator/Mixer (1 L bowl) at impeller blade speed 460 rpm and chopper speed of 2000 rpm for 2 minutes.
3. Addition of granulating solution containing surfactant, binder (7.1% w/w Hypromellose Methocel E3 solution) and mixing with the intragranular components in GMX-High Shear Granulator/Mixer at impeller blade speed 460 rpm and chopper blade 2000 rpm for 8-10 minutes.
4. Addition of about 1.5 g water to rinse the container, granulation for additional 2 minutes, recording of the visual observation of the wet mixture.
5. Drying of wet granular mass using a Midi-Glatt fluid bed dryer/processor at inlet temperature 35-40° C. until the loss on drying (LOD) of the granules reached the range of 4.00-5.50% w/w. following are the typical drying parameters.

| Parameters | Units |
|---|---|
| Product Air Pressure (bar) | 0.25-0.30 |
| Inlet Air Temperature (° C.) | 35 |
| Filter Blowing Rate (Sec) | 1 |
| Product Temperature (° C.)- at end | 20-21 |

6. Passing of the dried granules through Quadro Comil equipped with 2B039R03125173*(991) screen.
7. Weighing of the granules, then recalculation and weighing of extragranular ingredients.
8. Passing of the Tecovirimat granules and granular Simethicone through Quadro Comil equipped with 2B039R03125173*(991) screen.
9. Passing of the Tecovirimat granulate and granular Simethicone through a #20 screen.
10. Passing of lactose through a #20 screen and addition of Flavor on lactose with geometric mixing using spatula.
11. Passing of polymer and sucralose through a #40 screen.
12. Blending of the Tecovirimat-Simethicone blend and other extragranular components in the V-blender for 15 minutes.

13. Passing of magnesium stearate through a #40 screen, then addition as a lubricant to above milled blend and lubricate for 5 minutes.
14. Evaluation of the physicochemical properties of blend (Table 26).
15. Transfer of 10 doses of blend to a 100 cc glass bottle. Add water Q. S. to 50 mL. Shake well to mix the content. Evaluate the physicochemical properties of suspension (Table 27).
16. Packing of 20 doses of blend in Stick pack PAKVF2.5M Fin seal pouches (part #25M0275FS06); size 2.5 inch×6 inch. Heat-seal properly. Prepare 3 pouches for dissolution study (Table 28).

TABLE 26

Characterization of blends DS-85 to DS-87

| S# | Property | Batch: FSIG-20150120-1 (DS-85) | Batch: FSIG-20150120-2 (DS-86) | Batch: FSIG-20150120-3 (DS-87) |
|---|---|---|---|---|
| 1 | Appearance | White powder | White powder | White powder |
| 2 | Flow of Lubricated Blend (Flodex Orifice mm) | 24 | 24 | 24 |
| 3 | Bulk Density (g/cc) | 0.454 | 0.436 | 0.426 |
|   | Tap Density (g/cc) | 0.605 | 0.590 | 0.568 |
|   | Compressibility Index (%) | 25.0 | 26.1 | 25.0 |
| 4 | Granules Retained on Sieve # 20 (opening size 0.850 mm) (%) | 0.02 | 0.02 | 0.02 |
|   | Granules Retained on Sieve # 30 (opening size 0.600 mm) (%) | 8.03 | 4.84 | 2.04 |
|   | Granules Retained on Sieve # 40 (opening size 0.425 mm) (%) | 18.50 | 18.50 | 8.81 |
|   | Granules Retained on Sieve # 50 (opening size 0.300 mm) (%) | 14.86 | 12.11 | 10.99 |
|   | Granules Retained on Sieve # 60 (opening size 0.250 mm) (%) | 5.32 | 3.60 | 6.14 |
|   | Granules Retained on Sieve # 80 (opening size 0.180 mm) (%) | 37.04 | 28.28 | 38.65 |
|   | Retained on Pan (size <0.180 mm) (%) | 16.24 | 32.65 | 33.35 |
|   | Mean Size (mm) | 0.252 | 0.204 | 0.168 |

TABLE 27

Characterization of suspensions of DS-85 to DS-87

| S# | Property | Batch: FSIG-20150120-1 (DS-85) | | | Batch: FSIG-20150120-2 (DS-86) |
|---|---|---|---|---|---|
| 1 | Reconstitution | After manual shaking, no fish eyes is observed, disperse very well. | | | After manual shaking, no fish eye is observed, disperse very well. |
| 2 | Appearance after reconstitution | White dispersion | | | White dispersion |
| 3 | pH of suspension | 6.11 | | | 6.10 |
| 4 | Microscopic observation | Particle size 4.10 ± 3.42 μm. No agglomeration observed. | | | Particle size 4.40 ± 3.52 μm. No agglomeration observed. |
| 5 | Physical stability | No phase separation or agglomeration. | | | No phase separation or agglomeration. |
| 6 | Forced settling and redispersibility | Redispersible | | | Redispersible |
| 7 | Observation of sedimentation | 10 min | 30 min | 24 hr | 10 min |
| | | At 25° C. | | | |
| | Sedimentation coefficient | 1.00 | 1.00 | 1.00 | 1.00 |
| | Separation | None | None | Second layer (22% height) | None |
| | Redispersibility | Redispersible | Redispersible | Redispersible | Redispersible |
| | | At 5° C. | | | |
| | Sedimentation coefficient | 1.00 | 1.00 | 1.00 | 1.00 |
| | Separation | None | None | Second layer (22% height) | None |
| | Redispersibility | Redispersible | Redispersible | Redispersible | Redispersible |

| S# | Batch: FSIG-20150120-2 (DS-86) | Batch: FSIG-20150120-3 (DS-87) |
|---|---|---|
| 1 | After manual shaking, no fish eye is observed, disperse very well. | After manual shaking, no fish eye is observed, disperse very well. |
| 2 | White dispersion | White dispersion |

TABLE 27-continued

Characterization of suspensions of DS-85 to DS-87

| | | | | | |
|---|---|---|---|---|---|
| 3 | 6.10 | | 6.12 | | |
| 4 | Particle size 4.40 ± 3.52 µm. No agglomeration observed. | | Particle size 4.84 ± 4.22 µm. No agglomeration observed. | | |
| 5 | No phase separation or agglomeration. | | No phase separation or agglomeration. | | |
| 6 | Redispersible | | Redispersible | | |
| 7 | 30 min | 24 hr | 10 min | 30 min | 24 hr |

At 25° C.

| | | | | |
|---|---|---|---|---|
| 1.00 | 1.00 | 1.00 | 1.00 | 1.00 |
| None | Second layer (22% height) | None | None | Second layer (26% height) |
| Redispersible | Redispersible | Redispersible | Redispersible | Redispersible |

At 5° C.

| | | | | |
|---|---|---|---|---|
| 1.00 | 1.00 | 1.00 | 1.00 | 1.00 |
| None | Second layer (25% height) | None | None | Second layer (25% height) |
| Redispersible | Redispersible | Redispersible | Redispersible | Redispersible |

TABLE 28

Dissolution profile of DS-85 to DS-87

| Property | | Batch: FSIG-20150120-1 | | Batch: FSIG-20150120-2 | | Batch: FSIG-20150120-3 | |
|---|---|---|---|---|---|---|---|
| | Time | (DS-85) | | (DS-86) | | (DS-87) | |
| S# | (mins) | % Released | SD | % Released | SD | % Released | SD |
| 1 Dissolution (n = 6) | 5 | 72.5 | 1.6 | 58.8 | 1.5 | 36.0 | 1.2 |
| | 10 | 82.2 | 0.7 | 66.7 | 3.0 | 46.0 | 0.9 |
| | 15 | 85.5 | 1.1 | 71.8 | 2.3 | 51.7 | 0.8 |
| | 30 | 88.2 | 2.3 | 75.7 | 3.3 | 60.2 | 1.7 |
| | 45 | 90.3 | 2.0 | 80.4 | 3.0 | 64.7 | 1.0 |

Figure 3:
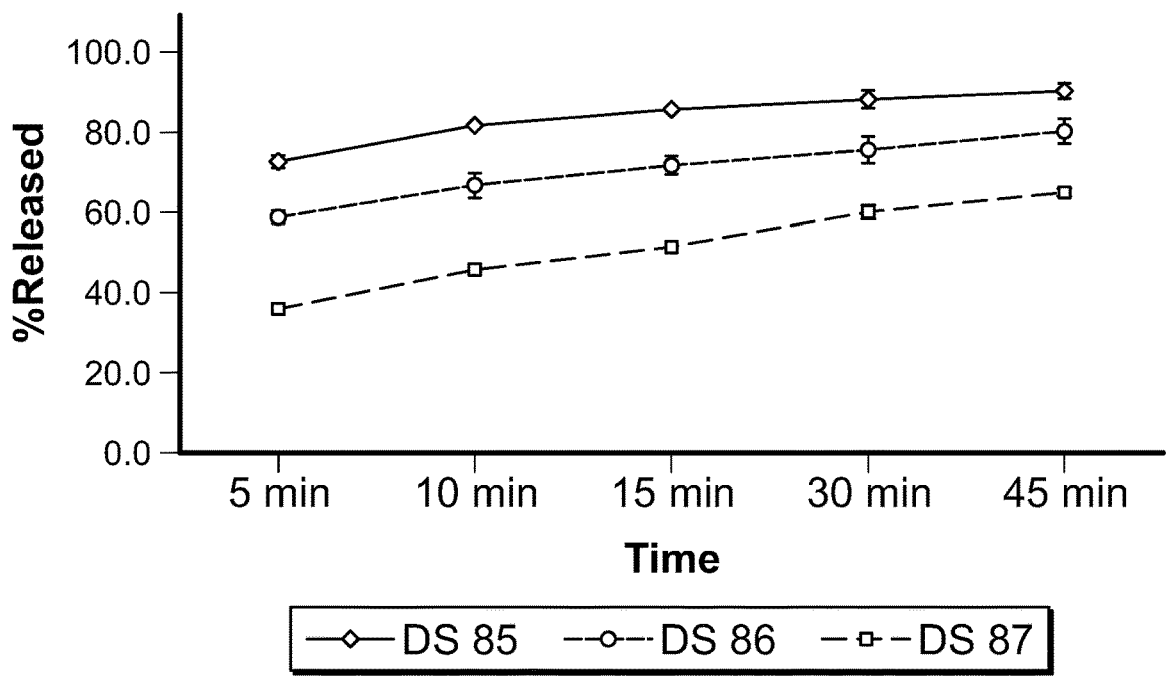

It was observed that DS-85 (API D90=21.51 m) showed higher dissolution rate compared to DS-86 (API D90=38.74 m) and DS-87 (API D90=81.53 m). The particle size of the Tecovirimat monohydrate used for granulation is inversely proportional to the dissolution rate. Smaller particle API batches showed higher dissolution rate as; DS-85>DS-86>DS-87 (see FIG. 3).

Example 13: Optimization of Blending and Lubrication Time Tecovirimat Monohydrate Powder for Reconstitution To study the effect of blend/lubrication time on blend uniformity and dissolution, sample where taken at different time points during a blending range of 10-25 minutes and a lubrication of 3-10 minutes. Composition is given in Table 29.

TABLE 29

Composition of DS-88

| S. # | Ingredients | Quantity per unit (mg) Goal: Blend or lube time DOE study (500 g scale). Ref. DS-75 (Batch # FSIG-20140826-1) Batch: FSIG-20150317-1 (DS-88) |
|---|---|---|
| 1 | Tecovirimat Granulate | 346.49 |
| 2 | Lactose monohydrate, NF (SuperTab 11SD) | 66.01 |
| 3 | Methylcellulose, 400 cps, USP | 50.00 |
| 4 | Sucralose, NF | 10.00 |
| 5 | Strawberry flavor, #133.16296 | 5.00 |
| 6 | Simethicone Granular Solid (MED-342), USP | 20.00 |
| 7 | Magnesium stearate, NF | 2.50 |
| | Total weight (mg) | 500.00 |

The batch size was 0.500 Kg. In general, the formulation procedure involved the following steps:

1. Passing of the Tecovirimat granules and granular Simethicone through Quadro Comil equipped with 2B039R03125173*(991) screen;
2. Passing of the Tecovirimat granulate and granular Simethicone through a #20 screen;
3. Passing of lactose through a #20 screen, then addition of Flavor on lactose with geometric mixing using spatula;
4. Passing of polymer and sucralose through a #40 screen;
5. Blending of the Tecovirimat-Simethicone blend and other extragranular components in the V-blender, taking a 10 g sample at 10, 15, and 20 minutes. Halt the process at 25 minutes and repeat sampling;
6. Passing of magnesium stearate through a #40 screen, then addition of 2.3 g as a lubricant to the remaining blend for lubrication. Take a 10 g sample at 3, 5, and 7.5 minutes. Final lubrication time is 10 minutes and repeat sampling;
7. Evaluation of the physicochemical properties of blend (Table 30);
8. Transfer of 10 doses of blend to a 100 cc glass bottle. Add water Q. S. to 50 mL. Shake well to mix the content. Evaluate the physicochemical properties of suspension (Table 31);
9. Addition of Q.S. purified water to 10 g samples at different blending or lube time points to make 100 mL, then stirring well for tests of reconstitution and dissolution (Table 32A and 32 B).

TABLE 30

Characterization of Blend DS-88

| S# | Property | Batch: FSIG-20150317-1 (DS-88) |
|---|---|---|
| 1 | Appearance | White powder |
| 2 | Flow of Lubricated Blend (Flodex Orifice mm) | 24 |
| 3 | Bulk Density (g/cc) | 0.518 |
|   | Tap Density (g/cc) | 0.700 |
|   | Compressibility Index (%) | 26.0 |
| 4 | Granules Retained on Sieve # 20 (opening size 0.850 mm) (%) | 0.01 |
|   | Granules Retained on Sieve # 30 (opening size 0.600 mm) (%) | 4.09 |
|   | Granules Retained on Sieve # 40 (opening size 0.425 mm) (%) | 10.36 |
|   | Granules Retained on Sieve # 50 (opening size 0.300 mm) (%) | 9.20 |
|   | Granules Retained on Sieve # 60 (opening size 0.250 mm) (%) | 4.03 |
|   | Granules Retained on Sieve # 80 (opening size 0.180 mm) (%) | 14.76 |
|   | Retained on Pan (size <0.180 mm) (%) | 57.55 |
|   | Mean Size (mm) | 0.133 |

TABLE 31

Characterization of suspension of DS-88

| S# | Property | Batch: FSIG-20150317-1 (DS-88) | | |
|---|---|---|---|---|
| 1 | Reconstitution | After manual shaking, 1 fish eye is observed at bottom of bottle. | | |
| 2 | Appearance after reconstitution | White dispersion | | |
| 3 | pH of suspension | 6.13 | | |
| 4 | Microscopic observation | Particle size 3.28 ± 2.72 μm. No agglomeration observed. | | |
| 5 | Physical stability | No phase separation or agglomeration. | | |
| 6 | Forced settling and redispersibility | Redispersible | | |
| 7 | Observation of sedimentation | 10 min | 30 min | 24 hr |
|   | At 25° C. | | | |
|   | Sedimentation coefficient | 1.00 | 1.00 | 1.00 |
|   | Separation | None | None | Second layer (22% height) |
|   | Redispersibility | Redispersible | Redispersible | Redispersible |
|   | At 5° C. | | | |
|   | Sedimentation coefficient | 1.00 | 1.00 | 1.00 |
|   | Separation | None | None | Second layer (20% height) |
|   | Redispersibility | Redispersible | Redispersible | Redispersible |

TABLE 32A

Figure 4:
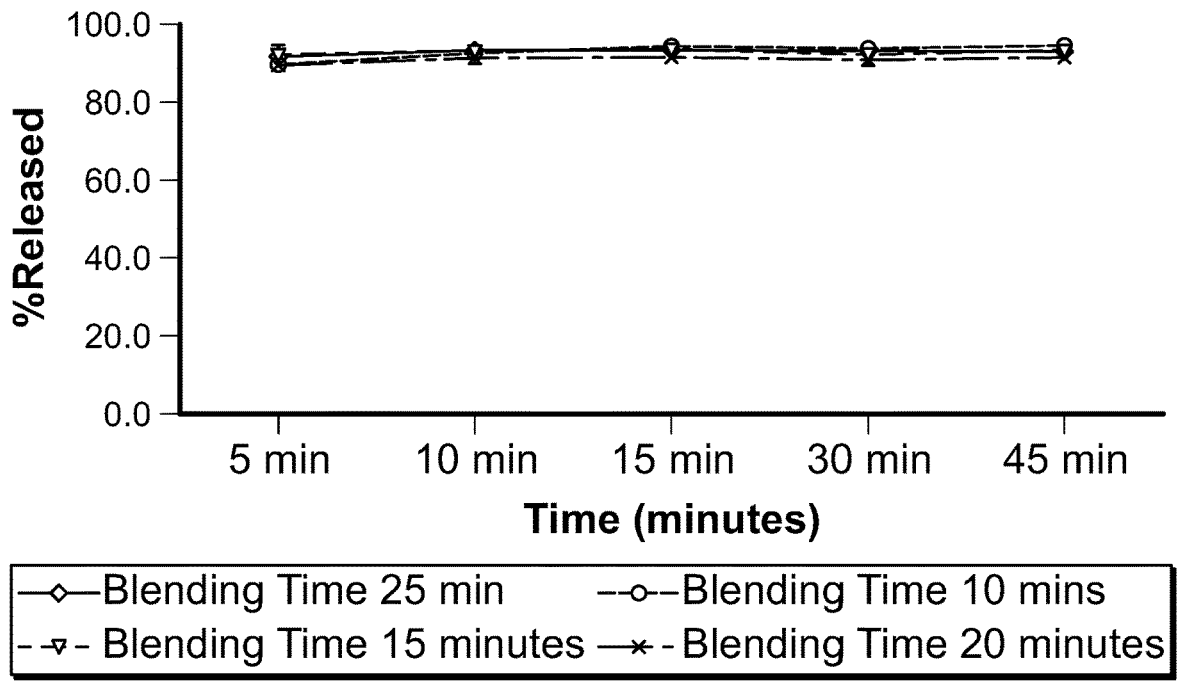

Reconstitution and Dissolution of Samples at Different Blending Times (see FIG. 4)

Batch: FSIG-20150317-1 (DS-88)

| S# | Property | | Blending 10 minutes (no lubricant) | | Blending 15 minutes (no lubricant) | | Blending 20 minutes (no lubricant) | | Blending 25 minutes (no lubricant) | |
|---|---|---|---|---|---|---|---|---|---|---|
| 1 | Reconstitution | | Tiny lumps, a little foam | | Tiny lumps, a little foam | | Tiny lumps, a little foam | | Tiny lumps, a little foam | |
| | | Time (mins) | % Released | SD | % Released | SD | % Released | SD | % Released | SD |
| 2 | Dissolution (n = 6) | 5 | 90.6 | 1.0 | 92.5 | 2.4 | 90.2 | 1.1 | 92.3 | 1.2 |
| | | 10 | 92.8 | 1.7 | 93.6 | 0.5 | 91.8 | 1.7 | 93.3 | 1.4 |
| | | 15 | 94.7 | 0.7 | 93.7 | 1.4 | 91.8 | 1.0 | 94.0 | 1.0 |
| | | 30 | 94.2 | 0.9 | 92.6 | 1.9 | 91.5 | 1.8 | 93.2 | 1.0 |
| | | 45 | 94.8 | 0.7 | 93.6 | 1.9 | 91.9 | 1.1 | 93.2 | 0.8 |

TABLE 32B

Figure 5:
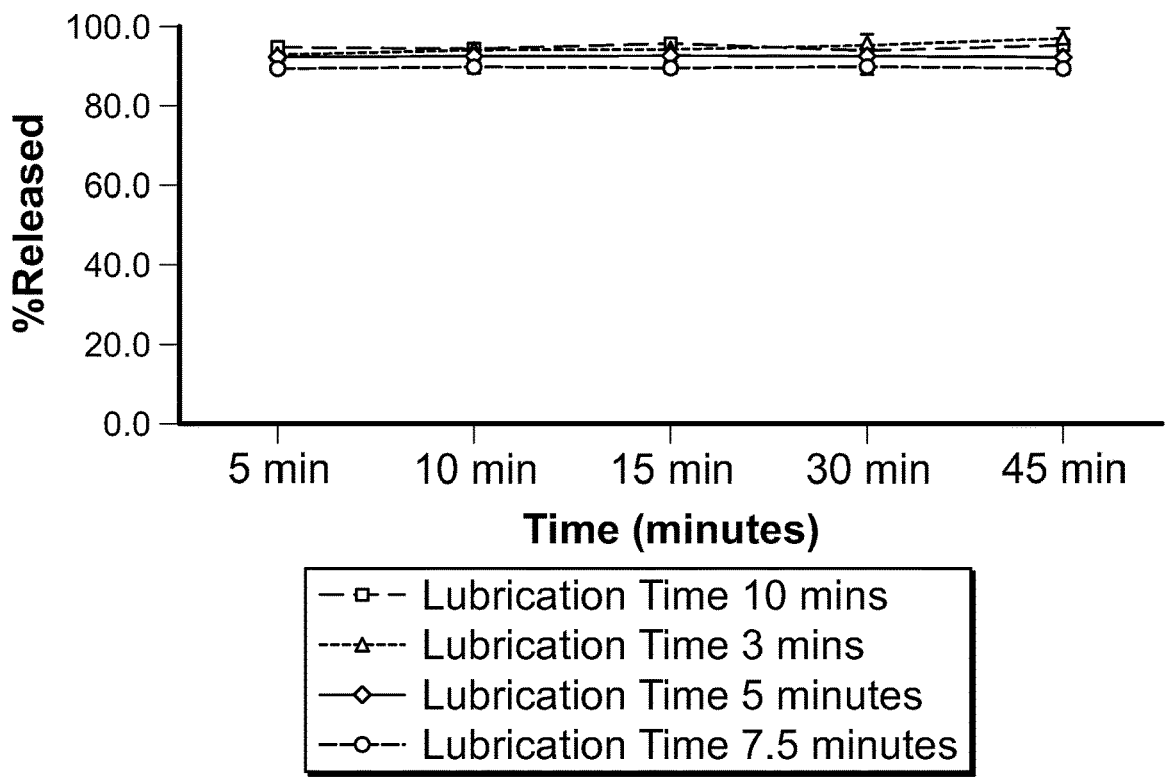

Reconstitution and Dissolution of Samples at Different Lubrication Time (see FIG. 5)

Batch: FSIG-20150317-1 (DS-88)

| S# | Property | Lubrication 3 minutes (with lubricant) | | Lubrication 5 minutes (with lubricant) | | Lubrication 7.5 minutes (with lubricant) | | Lubrication 10 minutes (with lubricant) | |
|---|---|---|---|---|---|---|---|---|---|
| 1 | Reconstitution | Tiny lumps, a little foam | | Tiny lumps, a little foam | | Tiny lumps, a little foam | | Tiny lumps, a little foam | |
| | | % Released | SD | % Released | SD | % Released | SD | % Released | SD |
| 2 | Dissolution (n = 6) | 93.6 | 1.6 | 92.9 | 1.1 | 90.0 | 1.1 | 95.5 | 1.3 |
| | | 94.8 | 1.7 | 93.3 | 0.8 | 90.6 | 1.6 | 94.9 | 1.2 |
| | | 94.6 | 2.3 | 93.4 | 0.7 | 90.1 | 1.5 | 96.4 | 1.5 |
| | | 96.2 | 2.6 | 93.3 | 1.1 | 90.5 | 1.9 | 94.4 | 1.1 |
| | | 97.7 | 2.3 | 92.9 | 1.1 | 90.0 | 1.5 | 96.1 | 1.4 |

It was observed that all samples showed above 90% dissolution in 5 minutes, indicating that a blending range of 10-25 minutes and a lubrication range of 3-10 minutes have no significant effect on sample dissolution. Blending time and lubrication time is now fixed as 15 minutes and 5 minutes respectively as previous trials.

Example 31: Evaluation of Effect of High/Low Lubrication

To evaluate the effect of lubrication on +/−50% deviation of magnesium stearate level was used to test the effect of lubricant level on formulation physicochemical properties and dissolution. Compositions are given in Table 33.

TABLE 33

Composition of DS-89 and 90

Quantity per unit (mg)
Goal: High/low lubricant DOE study
(500 g scale).
Ref. DS-75
(Batch # FSIG-20140826-1)

| S. # | Ingredients | Batch: FSIG-20150325-1 (DS-89) 0.25% magnesium stearate | Batch: FSIG-20150325-2 (DS-90) 0.75% magnesium stearate |
|---|---|---|---|
| 1 | Tecovirimat Granulate | 346.49 | 346.49 |
| 2 | Lactose monohydrate, NF (SuperTab 11SD) | 67.26 | 64.76 |
| 3 | Methylcellulose, 400 cps, USP | 50.00 | 50.00 |
| 4 | Sucralose, NF | 10.00 | 10.00 |

TABLE 33-continued

Composition of DS-89 and 90

Quantity per unit (mg)
Goal: High/low lubricant DOE study
(500 g scale).
Ref. DS-75
(Batch # FSIG-20140826-1)

| S. # | Ingredients | Batch: FSIG-20150325-1 (DS-89) 0.25% magnesium stearate | Batch: FSIG-20150325-2 (DS-90) 0.75% magnesium stearate |
|---|---|---|---|
| 5 | Strawberry flavor, #133.16296 | 5.00 | 5.00 |
| 6 | Simethicone Granular Solid (MED-342), USP | 20.00 | 20.00 |
| 7 | Magnesium stearate, NF | 1.25 | 3.75 |
|  | Total weight (mg) | 500.00 | 500.00 |

The batch size of each composition was 0.500 kg. In general, the formulation procedure involved the following steps:

1. Passing of the Tecovirimat granules and granular Simethicone through Quadro Comil equipped with 2B039R03125173*(991) screen.
2. Passing of the Tecovirimat granulate and granular Simethicone through a #20 screen.
3. Passing of lactose through a #20 screen, then addition of Flavor on lactose with geometric mixing using spatula.
4. Passing of polymer and sucralose through a #40 screen.
5. Blending of the Tecovirimat-Simethicone blend and other extragranular components in the V-blender for 15 minutes.
6. Passing of magnesium stearate through a #40 screen, then addition as a lubricant to above milled blend and lubricate for 5 minutes.
7. Evaluation of the physicochemical properties of blend (Table 34).
8. Transfer of 10 doses of blend to 100 cc glass bottle. Add water Q.S. to 50 mL. Shake well to mix the content. Evaluate the physicochemical properties of suspension (Table 35).
9. Packing of 20 doses of blend in Stick pack PAKVF2.5M Fin seal pouches (part #25M0275FS06); size 2.5 inch×6 inch. Heat-seal properly. Prepare 3 pouches for dissolution study (Table 36).

TABLE 34

Characterization of blend DS-89 and DS-90

| S# | Property | Batch: FSIG-20150325-1 (DS-89) | Batch: FSIG-20150325-2 (DS-90) |
|---|---|---|---|
| 1 | Appearance | White powder | White powder |
| 2 | Flow of Lubricated Blend (Flodex Orifice mm) | 24 | 24 |
| 3 | Bulk Density (g/cc) | 0.544 | 0.531 |
|   | Tap Density (g/cc) | 0.706 | 0.698 |
|   | Compressibility Index (%) | 22.9 | 23.9 |
| 4 | Granules Retained on Sieve # 20 (opening size 0.850 mm) (%) | 0.01 | 0.06 |
|   | Granules Retained on Sieve # 30 (opening size 0.600 mm) (%) | 4.32 | 4.30 |
|   | Granules Retained on Sieve # 40 (opening size 0.425 mm) (%) | 10.01 | 9.89 |
|   | Granules Retained on Sieve # 50 (opening size 0.300 mm) (%) | 10.89 | 13.49 |
|   | Granules Retained on Sieve # 60 (opening size 0.250 mm) (%) | 6.16 | 5.92 |
|   | Granules Retained on Sieve # 80 (opening size 0.180 mm) (%) | 15.86 | 16.26 |
|   | Retained on Pan (size <0.180 mm) (%) | 52.74 | 50.08 |
|   | Mean Size (mm) | 0.145 | 0.153 |

TABLE 35

Characterization of suspension of DS-89 and DS-90

| S# | Property | Batch: FSIG-20150325-1 (DS-89) | | | Batch: FSIG-20150325-2 (DS-90) | | |
|---|---|---|---|---|---|---|---|
| 1 | Reconstitution | After manual shaking, no fish eye is observed, disperse very well. | | | After manual shaking, 2 fish eyes are observed at bottom of bottle. | | |
| 2 | Appearance after reconstitution | White dispersion | | | White dispersion | | |
| 3 | pH of suspension | 6.07 | | | 6.12 | | |
| 4 | Microscopic observation | Particle size 3.22 ± 2.91 µm. No agglomeration observed. | | | Particle size 3.26 ± 3.00 µm. No agglomeration observed. | | |
| 5 | Physical stability | No phase separation or agglomeration. | | | No phase separation or agglomeration. | | |
| 6 | Forced settling and redispersibility | Redispersible | | | Redispersible | | |
| 7 | Observation of sedimentation | 10 min | 30 min | 24 hr | 10 min | 30 min | 24 hr |
| | | At 25° C. | | | | | |
| | Sedimentation coefficient | 1.00 | 1.00 | 1.00 | 1.00 | 1.00 | 1.00 |
| | Separation | None | None | Second layer (22% height) | None | None | Second layer (23% height) |
| | Redispersibility | Redispersible | Redispersible | Redispersible | Redispersible | Redispersible | Redispersible |
| | | At 5° C. | | | | | |
| | Sedimentation coefficient | 1.00 | 1.00 | 1.00 | 1.00 | 1.00 | 1.00 |
| | Separation | None | None | Second layer (20% height) | None | None | Second layer (36% height) |
| | Redispersibility | Redispersible | Redispersible | Redispersible | Redispersible | Redispersible | Redispersible |

TABLE 36

Figure 6:
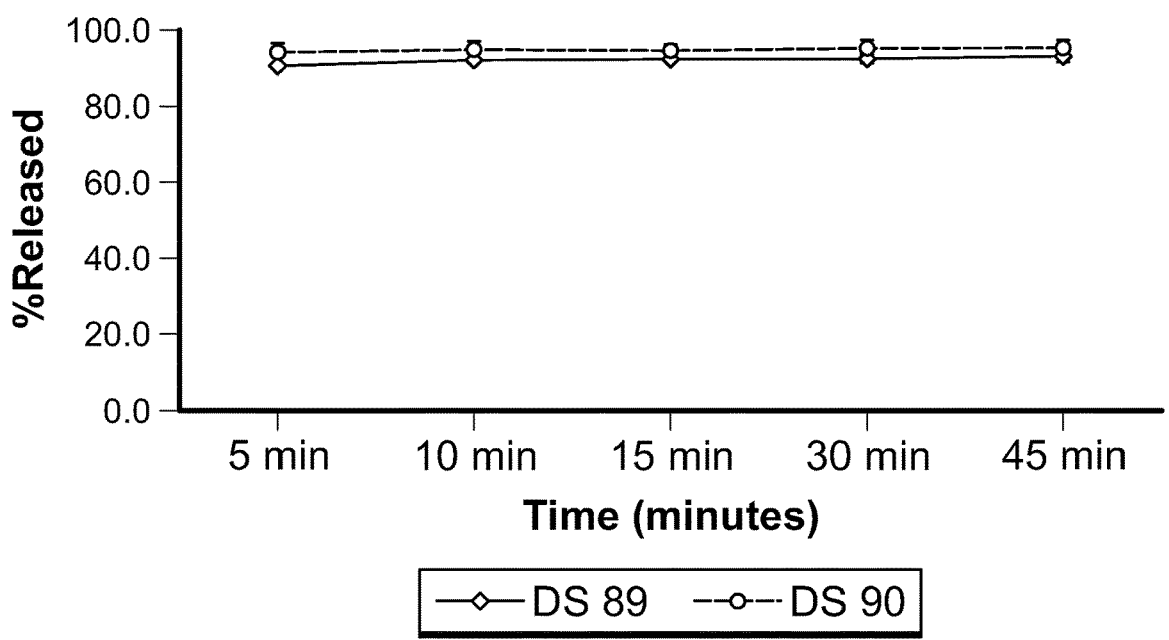
Figure 7:
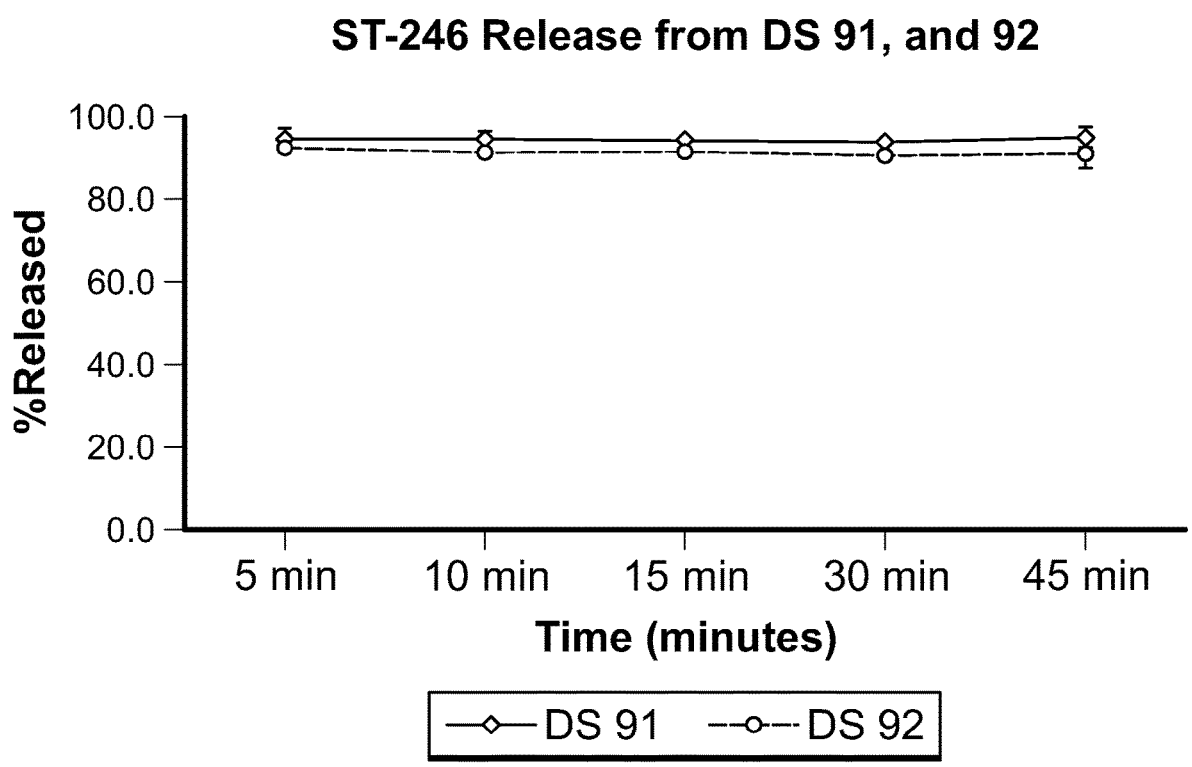
Figure 8B:
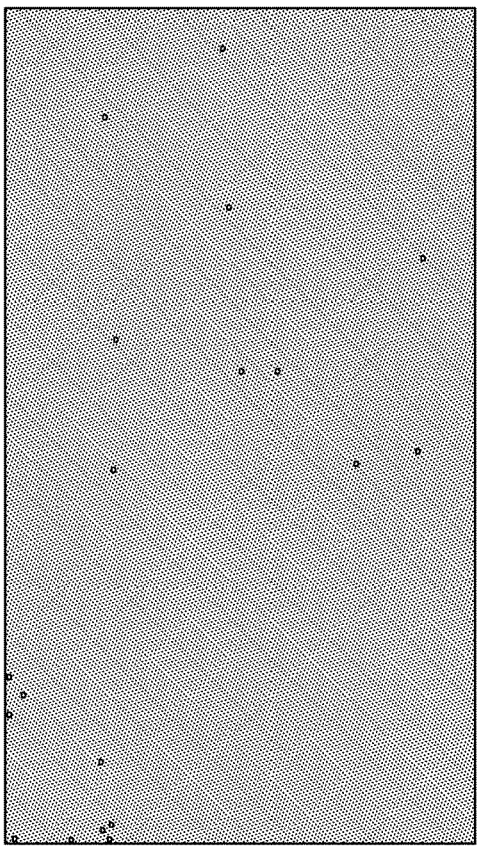
Figure 8D:
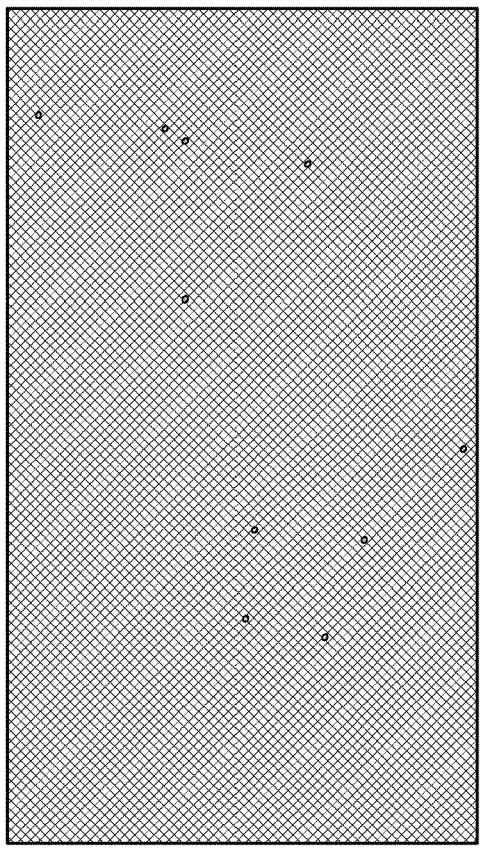
Figure 8A:
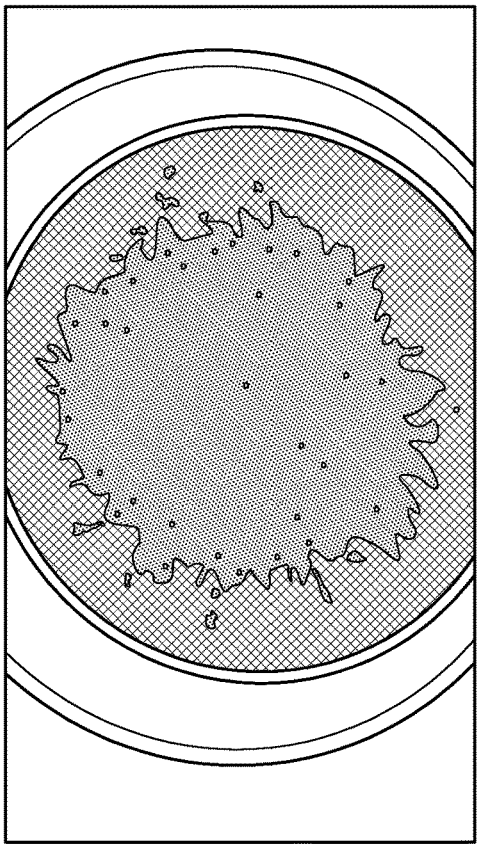
Figure 8C:
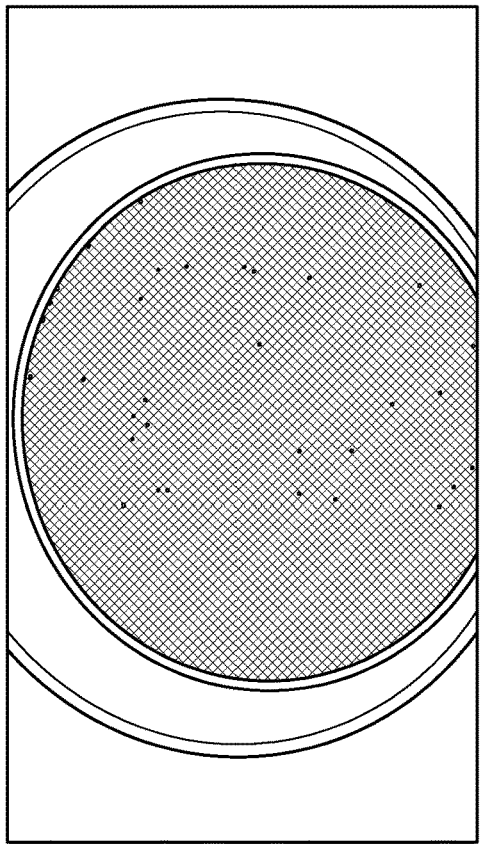

Dissolution of DS-89 and DS-90 (see FIG. 6)

| | Property | | Batch: FSIG-20150325-1 (DS-89) | | Batch: FSIG-20150325-2 (DS-90) | |
|---|---|---|---|---|---|---|
| S# | | Time (min) | % Released | SD | % Released | SD |
| 1 | Dissolution (n = 6) | 5 | 91.2 | 0.7 | 94.8 | 2.2 |
| | | 10 | 92.6 | 0.5 | 95.5 | 1.8 |
| | | 15 | 92.9 | 1.1 | 95.1 | 1.5 |
| | | 30 | 92.8 | 1.1 | 95.6 | 2.3 |
| | | 45 | 93.8 | 1.8 | 95.8 | 2.0 |

The quantity of magnesium stearate at 0.2500 and 0.7500 level of the formulation did not show any difference in physicochemical properties as well as dissolution of the product.

Example 15: Effect of Milling on Particle Size and Size Distribution of Tecovirimat Granules The purpose is to study the effect of milling on particle size and size distribution of Tecovirimat granules. 100 of Tecovirimat granules from Siga were used to test the size distribution. 110 g of Tecovirimat granules from the same Siga Lot # were passed through Quadra Comil equipped with 2B039R03125173*(991) screen, from which 100 g were weighed for size distribution test. The results are shown in Table 37.

TABLE 37

Particle size and size distribution of Tecovirimat Granules before/after milling

| S# | Property | Lot # 1401165 (before milling) | Lot # 1401165 (after milling) |
|---|---|---|---|
| 1 | Granules Retained on Sieve # 20 (opening size 0.850 mm) (%) | 0.05 | 0.04 |
|  | Granules Retained on Sieve # 30 (opening size 0.600 mm) (%) | 6.38 | 4.47 |
|  | Granules Retained on Sieve # 40 (opening size 0.425 mm) (%) | 10.34 | 12.31 |
|  | Granules Retained on Sieve # 50 (opening size 0.300 mm) (%) | 10.80 | 11.64 |
|  | Granules Retained on Sieve # 60 (opening size 0.250 mm) (%) | 5.05 | 5.36 |
|  | Granules Retained on Sieve # 80 (opening size 0.180 mm) (%) | 8.48 | 8.55 |
|  | Granules Retained on Sieve # 100 (opening size 0.150 mm) (%) | 4.74 | 4.70 |
|  | Retained on Pan (size <0.150 mm) (%) | 54.17 | 52.93 |
|  | Mean Size (mm) | 0.150 | 0.150 |

It was observed that no significant different between the size distribution of Tecovirimat granules before or after milling.

Example 16: Evaluation of Pre-dilution and as is Simethicone Before Mixing/Blending Simethicone granular grade is currently prediluted/milled with Tecovirimat granules. The pre-dilution and no-dilution/as is Simethicone before mixing were compared, to establish the method of dilution that can be commercially reproduced at large scale. Compositions are given in Table 38.

TABLE 38

Composition of DS-91 and DS-92

| | | Quantity per unit (mg) Goal: Simethicone pre-dilution or no-dilution (500 g scale). Ref. DS-75 (Batch # FSIG-20140826-1) | |
|---|---|---|---|
| S. # | Ingredients | Batch: FSIG-20150407-1 (DS-91) pre-diluted Simethicone | Batch: FSIG-20150407-2 (DS-92) undiluted Simethicone |
| 1 | Tecovirimat Granulate | 346.49 | 346.49 |
| 2 | Lactose monohydrate, NF (SuperTab 11SD) | 66.01 | 66.01 |
| 3 | Methylcellulose, 400 cps, USP | 50.00 | 50.00 |
| 4 | Sucralose, NF | 10.00 | 10.00 |
| 5 | Strawberry flavor, #133.16296 | 5.00 | 5.00 |
| 6 | Simethicone Granular Solid (MED-342), USP | 20.00 | 20.00 |
| 7 | Magnesium stearate, NF | 2.50 | 2.50 |
|  | Total weight (mg) | 500.00 | 500.00 |

The batch size of each composition was 0.500 kg. In general, the formulation procedure involved the following steps:
1. For DS-91, passing of the Tecovirimat granules and granular Simethicone through Quadra Comil equipped with 2B039R03125173*(991) screen, then passing of the Tecovirimat granulate and granular Simethicone through a #20 screen;
2. For DS-92, passing of the Tecovirimat granulate through Quadra Comil equipped with 2B039R03125173*(991) screen; then passing of granular Simethicone through a #20 screen;
3. Passing of lactose through a #20 screen, then addition of Flavor on lactose with geometric mixing using spatula;
4. Passing of polymer and sucralose through a #40 screen;
5. Blending of Tecovirimat granulate and all the extragranular components in the V-blender for 15 minutes;
6. Passing of magnesium stearate through a #40 screen, then addition as a lubricant to above milled blend and lubricate for 5 minutes;
7. Evaluation of the physicochemical properties of blend (Table 39);
8. Transfer of 10 doses of blend to a 100 cc glass bottle. Add water Q. S. to 50 mL. Shake well to mix the content. Evaluate the physicochemical properties of suspension (Table 40);
9. Packing of 20 doses of blend in Stick pack PAKVF2.5M Fin seal pouches (part #25M0275FS06); size 2.5 inch×6 inch. Heat-seal properly. Prepare 3 pouches for dissolution study (Table 41).

TABLE 39

Characterization of blend DS-91 and DS-92

| S# | Property | Batch: FSIG-20150407-1 (DS-91) | Batch: FSIG-20150407-2 (DS-92) |
|---|---|---|---|
| 1 | Appearance | White powder | White powder |
| 2 | Flow of Lubricated Blend (Flodex Orifice mm) | 24 | 26 |
| 3 | Bulk Density (g/cc) | 0.533 | 0.525 |
|  | Tap Density (g/cc) | 0.701 | 0.700 |
|  | Compressibility Index (%) | 24.0 | 25.0 |
| 4 | Granules Retained on Sieve # 20 (opening size 0.850 mm) (%) | 0.03 | 0.06 |
|  | Granules Retained on Sieve # 30 (opening size 0.600 mm) (%) | 4.26 | 4.06 |
|  | Granules Retained on Sieve # 40 (opening size 0.425 mm) (%) | 10.10 | 10.49 |
|  | Granules Retained on Sieve # 50 (opening size 0.300 mm) (%) | 10.87 | 10.11 |
|  | Granules Retained on Sieve # 60 (opening size 0.250 mm) (%) | 3.50 | 4.18 |
|  | Granules Retained on Sieve # 80 (opening size 0.180 mm) (%) | 12.92 | 13.80 |
|  | Retained on Pan (size <0.180 mm) (%) | 58.32 | 57.30 |
|  | Mean Size (mm) | 0.133 | 0.135 |

TABLE 40

Physicochemical Properties of Suspension of DS-91 and DS-92

| S# | Property | Batch: FSIG-20150407-1 (DS-91) | | | Batch: FSIG-20150407-2 (DS-92) | | |
|---|---|---|---|---|---|---|---|
| 1 | Reconstitution | After manual shaking, no fish eye is observed, disperse very well. | | | After manual shaking, no fish eye is observed, disperse very well. | | |
| 2 | Appearance after reconstitution | White dispersion. Foaminess similar to DS-92 | | | White dispersion. Foaminess similar to DS-91. | | |
| 3 | pH of suspension | 6.11 | | | 6.05 | | |
| 4 | Microscopic observation | Particle size 3.02 ± 2.03 µm. No agglomeration observed. | | | Particle size 3.14 ± 2.47 µm. No agglomeration observed. | | |
| 5 | Physical stability | No phase separation or agglomeration. | | | No phase separation or agglomeration. | | |
| 6 | Forced settling and redispersibility | Redispersible | | | Redispersible | | |
| 7 | Observation of sedimentation | 10 min | 30 min | 24 hr | 10 min | 30 min | 24 hr |
|  | At 25° C. | | | | | | |
|  | Sedimentation coefficient | 1.00 | 1.00 | 1.00 | 1.00 | 1.00 | 1.00 |
|  | Separation | None | None | Second layer (28% height) | None | None | Second layer (33% height) |
|  | Redispersibility | Redispersible | Redispersible | Redispersible | Redispersible | Redispersible | Redispersible |
|  | At 5° C. | | | | | | |
|  | Sedimentation coefficient | 1.00 | 1.00 | 1.00 | 1.00 | 1.00 | 1.00 |
|  | Separation | None | None | Second layer (28% height) | None | None | Second layer (33% height) |
|  | Redispersibility | Redispersible | Redispersible | Redispersible | Redispersible | Redispersible | Redispersible |

TABLE 41

Dissolution of DS-91 and DS-92

| | | | Batch: FSIG-20150407-1 (DS-91) | | Batch: FSIG-20150407-2 (DS-92) | |
|---|---|---|---|---|---|---|
| S# | Property | Time (min) | % Released | SD | % Released | SD |
| 1 | Dissolution (n = 6) | 5 | 94.7 | 2.3 | 92.2 | 1.2 |
|  |  | 10 | 94.6 | 1.9 | 91.3 | 1.2 |

TABLE 41-continued

Dissolution of DS-91 and DS-92

| | Property | Batch: FSIG-20150407-1 | | Batch: FSIG-20150407-2 | |
|---|---|---|---|---|---|
| | Time | (DS-91) | | (DS-92) | |
| S# | (min) | % Released | SD | % Released | SD |
| | 15 | 94.2 | 1.2 | 91.6 | 1.3 |
| | 30 | 93.8 | 1.1 | 90.6 | 1.2 |
| | 45 | 94.9 | 2.4 | 91.0 | 4.0 |

It was observed that before blending when passing through the #20 screen, Simethicone with no-dilution partly stuck on sieve (FIGS. 8 A and B), while the pre-diluted and co-milled Simethicone and Tecovirimat granules passed through #20 screen easily (FIGS. 8 C and D). After sieve shaking for size distribution analysis, big clumps from DS-92 remained on #20 screen (FIG. 9), indicating the formation of big Simethicone lumps when no-dilution before mixing.

FIG. 8 shows an observation when passing simethicone or co-milled simethicone-Tecovirimat granules through #20 screen. A and B: no-dilution simethicone stuck on screen. C and D: pre-diluted and co-milled simethicone-Tecovirimat granules passed screen easily without sticking.

Figure 9:
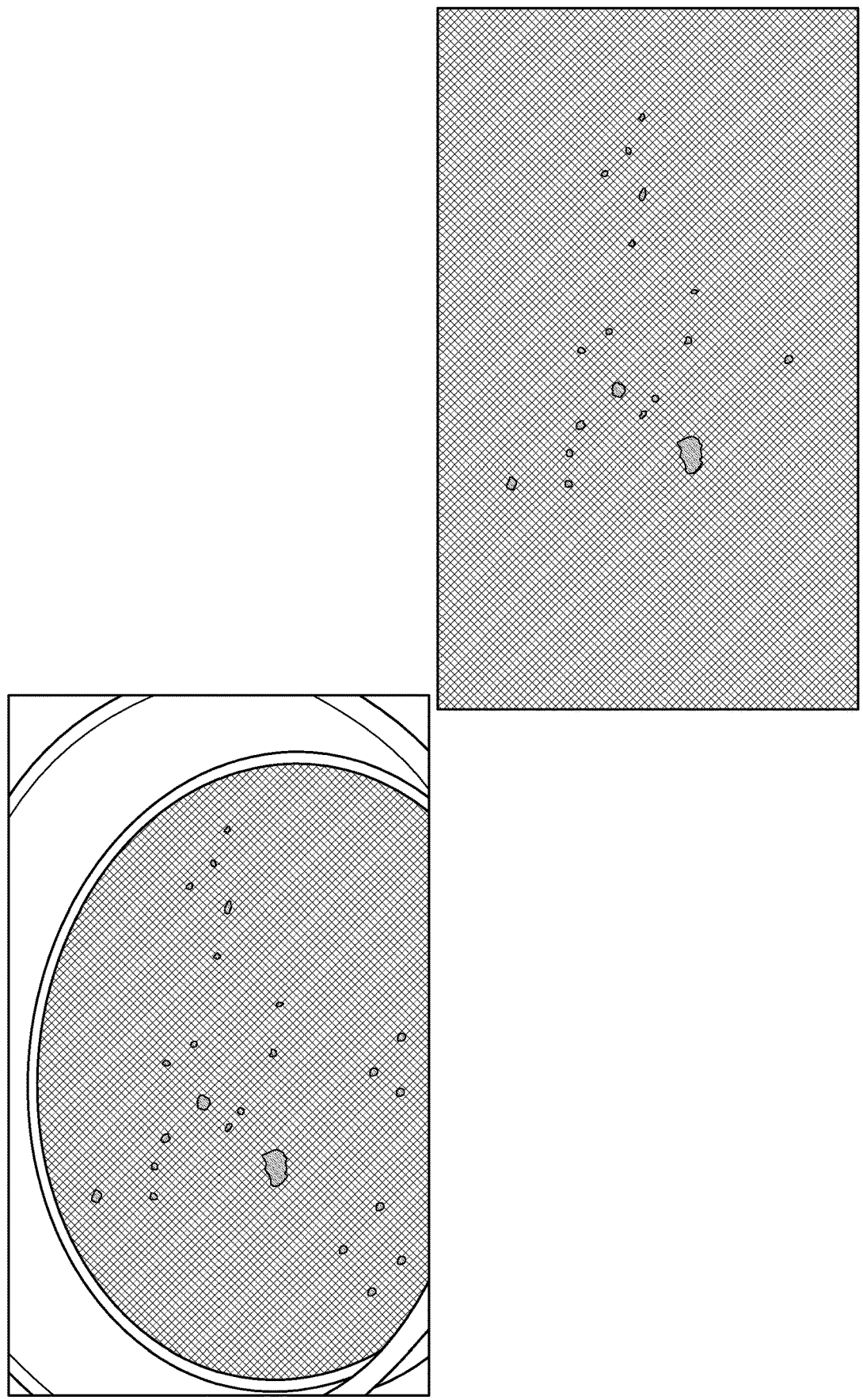

FIG. 9 shows retained clumps on #20 screen after sieve shaking of 100 g DS-92.

Example 17: Evaluation of Simethicone from Alternate Source

Currently Simethicone Granular Solid (MED-342) from Nusil Technologies was used. An alternate source of Simethicone-Simethicone 50% Powder from AIC was used to test the effect on formulation. The pre-dilution and no-dilution of simethicone before mixing were compared. Compositions are given in Table 41.

The batch size of each composition was 0.500 Kg. Detailed experimental procedures and results of each trial formulation were recorded in the executed batch records. In general, the formulation procedure involved the following steps:

1. For DS-93, passing of the Tecovirimat granules and Simethicone powder through Quadro Comil equipped with 2B039R03125173*(991) screen, then passing of the Tecovirimat granulate and Simethicone powder through a #20 screen;
2. For DS-94, passing of the Tecovirimat granulate through Quadro Comil equipped with 2B039R03125173*(991) screen; then passing of Simethicone powder through a #20 screen;
3. Passing of lactose through a #20 screen, then addition of Flavor on lactose with geometric mixing using spatula;
4. Passing of polymer and sucralose through a #40 screen;
5. Blending of Tecovirimat granulate and all the extra-granular components in the V-blender for 15 minutes;
6. Passing of magnesium stearate through a #40 screen, then addition as a lubricant to above milled blend and lubricate for 5 minutes;
7. Evaluation of the physicochemical properties of blend (Table 43);

TABLE 41

Composition of DS-93 and DS-94

| | | Quantity per unit (mg) Goal: Simethicone alternate source (500 g scale). Ref. DS-75 (Batch # FSIG-20140826-1) | |
|---|---|---|---|
| | | Batch: FSIG-20150421-1 (DS-93) pre-diluted simethicone | Batch: FSIG-20150421-2 (DS-94) Undiluted simethicone |
| S. # | Ingredients | | |
| 1 | Tecovirimat Granulate | 346.49 | 346.49 |
| 2 | Lactose monohydrate, NF (SuperTab 11SD) | 74.01 | 74.01 |
| 3 | Methylcellulose, 400 cps, USP | 50.00 | 50.00 |
| 4 | Sucralose, NF | 10.00 | 10.00 |
| 5 | Strawberry flavor, #133.16296 | 5.00 | 5.00 |
| 6 | Simethicone 50% Powder | 12.00 | 12.00 |
| 7 | Magnesium stearate, NF | 2.50 | 2.50 |
| | Total weight (mg) | 500.00 | 500.00 |

8. Transfer of 10 doses of blend to a 100 cc glass bottle. Add water Q.S. to 50 mL. Shake well to mix the content. Evaluate the physico chemical properties of suspension (Table 44);
9. Packing of 20 doses of blend in Stick pack PAKVF2.5M Finseal pouches (part #25M0275FS06); size 2.5 inch×6 inch. Heat-seal properly. Prepare 3 pouches for dissolution study (Table 45).

TABLE 43

Characterization of blend DS-93 and DS-94

| S# | Property | Batch: FSIG-20150421-1 (DS-93) | Batch: FSIG-20150421-2 (DS-94) |
|---|---|---|---|
| 1 | Appearance | White powder | White powder |
| 2 | Flow of Lubricated Blend (Flodex Orifice mm) | 20 | 20 |
| 3 | Bulk Density (g/cc) | 0.547 | 0.540 |
|   | Tap Density (g/cc) | 0.720 | 0.720 |
|   | Compressibility Index (%) | 24.0 | 25.0 |
| 4 | Granules Retained on Sieve # 20 (opening size 0.850 mm) (%) | 0.02 | 0.02 |
|   | Granules Retained on Sieve # 30 (opening size 0.600 mm) (%) | 3.23 | 2.81 |
|   | Granules Retained on Sieve # 40 (opening size 0.425 mm) (%) | 8.73 | 8.52 |
|   | Granules Retained on Sieve # 50 (opening size 0.300 mm) (%) | 9.28 | 8.48 |
|   | Granules Retained on Sieve # 60 (opening size 0.250 mm) (%) | 3.56 | 3.75 |
|   | Granules Retained on Sieve # 80 (opening size 0.180 mm) (%) | 13.96 | 11.28 |
|   | Retained on Pan (size <0.180 mm) (%) | 61.23 | 65.15 |
|   | Mean Size (mm) | 0.118 | 0.108 |

TABLE 44

Physicochemical properties of suspension of DS-93 and DS-94

| S# | Property | Batch: FSIG-20150421-1 (DS-93) | | | Batch: FSIG-20150421-2 (DS-94) | | |
|---|---|---|---|---|---|---|---|
| 1 | Reconstitution | After manual shaking, no fish eye is observed, disperse very well. | | | After manual shaking, no fish eye is observed, disperse very well. | | |
| 2 | Appearance after reconstitution | White dispersion, foaminess similar to DS-94, more foam than DS-91 and DS-92. | | | White dispersion, foaminess similar to DS-93, more foam than DS-91 and DS-92. | | |
| 3 | pH of suspension | 6.11 | | | 6.07 | | |
| 4 | Microscopic observation | Particle size 3.40 ± 3.04 μm. No agglomeration observed. | | | Particle size 3.46 ± 2.96 μm. No agglomeration observed. | | |
| 5 | Physical stability | No phase separation or agglomeration. | | | No phase separation or agglomeration. | | |
| 6 | Forced settling and redispersibility | Redispersible | | | Redispersible | | |
| 7 | Observation of sedimentation At 25° C. | 10 min | 30 min | 24 hr | 10 min | 30 min | 24 hr |
|   | Sedimentation coefficient | 1.00 | 1.00 | 1.00 | 1.00 | 1.00 | 1.00 |
|   | Separation | None | None | Second layer (26% height) | None | None | Second layer (29% height) |
|   | Redispersibility | Redispersible | Redispersible | Redispersible | Redispersible | Redispersible | Redispersible |
|   | At 5° C. | | | | | | |
|   | Sedimentation coefficient | 1.00 | 1.00 | 1.00 | 1.00 | 1.00 | 1.00 |
|   | Separation | None | None | Second layer (25% height) | None | None | Second layer (25% height) |
|   | Redispersibility | Redispersible | Redispersible | Redispersible | Redispersible | Redispersible | Redispersible |

TABLE 45

| | | Dissolution of DS-93 and DS-94 | | | |
|---|---|---|---|---|---|
| | Property | Batch: FSIG-20150421-1 | | Batch: FSIG-20150421-2 | |
| | Time | (DS-93) | | (DS-94) | |
| S# | (min) | % Released | SD | % Released | % Released |
| 1 | Dissolution | 5 | 82.5 | 1.7 | 89.3 | 89.3 |
| | (n = 6) | 10 | 84.7 | 1.4 | 86.8 | 86.8 |
| | | 15 | 85.4 | 0.7 | 86.9 | 86.9 |
| | | 30 | 86.5 | 1.1 | 88.2 | 88.2 |
| | | 45 | 86.2 | 1.9 | 88.4 | 88.4 |

It was observed that the undiluted simethicone 50% powder passed #20 screen easily without any sticking. The flowability of DS-93 and DS-94 using simethicone powder was better than that of previous batches using granular simethicone. The suspensions of DS-93 and DS-94 after reconstitution were similarly foamy, both containing much more foam than DS-91 and DS-92. Therefore the antifoaming effect of simethicone powder is not as efficient as that of granular simethicone.

Example 18: Taste Assessment of the Aqueous Pharmaceutical Suspension Formulations The taste of the aqueous pharmaceutical suspension formulations according to the present invention is critically important to the successful oral administration.

Consequently the present invention provides a palatable powder for suspension dosage form of Tecovirimat which is suitable for pediatric and geriatric dosing The following examples identify and quantify the sensory attributes (basic tastes, e.g., bitterness; aromatics and trigeminal effects) of a series of Tecovirimat aqueous suspensions.

Six experienced pharmaceutical sensory panelists were used to evaluate the above mentioned sensory attributes.

Samples were evaluated using the Flavor Profile method 1 of descriptive sensory analysis to identify, characterize and quantify the sensory attributes of the study samples. The Flavor Profile method was originally developed to assist The Upjohn Company in identifying off tastes in their gelatin capsules and provides a complete description of the sensory attributes of products, e.g., texture, aroma, taste, mouthfeel.

The method consists of formal procedures for describing and assessing the aroma (if appropriate) and flavor of a product in a reproducible manner. The Flavor Profile terms are shown in FIG. 11.

Flavor Profile is used to identify the individual attributes of product flavor, including:
1. Basic tastes: sweet, sour, salty, and bitter;
2. Aromatics: volatile components perceived by the olfactory system via the nasopharyngeal passage (retronasal) and
3. Feeling factors: numbing, cooling, warming, burning, drying, oily, astringent, etc.

Flavor Profile also includes measures of the strength, or intensity, at which these character notes appear; the order in which the character notes appear; and a description of all sensations i.e. basic tastes, feeling factors, and aromatics remaining at specified time intervals after swallowing.

For some oral pharmaceuticals texture attributes such as hardness (chewable tablets) or particulates/grittiness (chewable tablets, sachets, suspensions) are also noted and assessed.

For oral pharmaceuticals, both the initial flavor quality and the aftertaste flavor quality are important to patient acceptability, and therefore it is important that each be evaluated. The initial flavor characteristics of the study products were evaluated during the first 10-20 seconds, and the aftertaste attributes were evaluated at multiple time intervals to 30 minutes as described below.

Sample Constitution and Taste Evaluation Protocols

The compounded Tecovirimat powder for suspension, micronized tecovirimat API as well as tecovirimat granules taste assessment samples were constituted immediately prior to evaluations as follows:
1. The API-containing powder in an amber bottle was agitated to ensure the powder moves around freely.
2. The purified (reverse osmosis) water premeasured was added to each bottle containing the powder.
3. The bottles were mixed by hand for a few minutes. The unflavored bottles were mixed vigorously and the flavored bottles were mixed gently.
4. 5 mL samples were taken from each test formulation and dispensed to each panelist for evaluation.

The panelists evaluated the constituted samples as follows:
1. The panelists cleansed their palates with spring water and unsalted crackers.
2. 5 mL of sample was dispensed into individual 1-ounce plastic cups using a graduated oral syringe and distributed to each panelist.
3. Starting at the same time, the panelists poured the sample directly in to their mouths, swished the contents around the oral cavity for 10 seconds and expectorated. During this time the panelists independently evaluated and recorded the initial flavor characteristics.
4. The panelists then independently evaluated and recorded the aftertaste characteristics at periodic intervals out to 30 minutes as flavor persisted.
5. The panelists recited their individual results and a preliminary Flavor Profile was generated for the sample.
6. Steps 1 through 4 were repeated for a second evaluation of the sample using the preliminary Flavor Profile from Step 5 as a guide, with the panelists noting any necessary modifications.
7. The panelists recited their individual results and a final Flavor Profile was developed for the sample.

Flavor Leadership Criteria

The flavor quality of the flavored drug product prototypes was interpreted using the relevant Flavor Leadership Criteria. Research reveals that the perennial sales leaders in many categories, including pharmaceuticals, have a set of sensory characteristics in common, which are known as the Flavor Leadership Criteria. The flavor profiles associated with products typically having the highest sales within a product category possess the following characteristics:
1. Have a quickly recognizable identifying flavor;
2. Develop full flavor that rapidly blends with and covers the active and base characteristics;
3. Have no unpleasant mouth sensations (e.g., tongue sting);
4. Have no off-notes in the early impression or in the aftertaste;
5. Have a short (or appropriate) aftertaste.

The concepts of Flavor Leadership were used to interpret the sensory analysis results and are described more fully below.

Immediate Impact of the Identifying Flavor.

Flavor Leaders exhibit an immediate impact of the identifying flavor. When a consumer tastes a product, the first character notes provide for product identification and set expectations for the remainder of the flavor experience. For example, many inexpensive chocolates have an initial waxy impression whereas high-quality chocolates are identified by an initial chocolate flavor and cocoa butter mouthfeel. Unfortunately for many oral pharmaceuticals, the first impression is bitterness or an aromatic off-note (e.g., green stemmy, musty, chalky) that many patients find unacceptable.

Rapid Development of Balanced, Full Flavor.

A well-blended flavor is key to product success. Flavor Leaders have a flavor that develops rapidly and is full bodied and well balanced. Blended flavor means that a complex body of underlying sensory impressions that are not separately identified support the expected character notes. For example, Coca-Cola® comprises hundreds of individual flavoring components that are hard to single out individually, the components are very well blended. Unlike most foods and beverages, the challenge for pharmaceuticals is to "blend away" the negative sensory attributes of the drug substance, while simultaneously minimizing the number of excipients in the formulation. Amplitude is an integrative measure of balance and fullness (see FIG. 11). It is an overall measure of the quality of the initial flavor and has been shown to correlate with palatability and patient acceptance. Amplitude of 1 is appropriate for most oral pharmaceuticals.

Compatible Mouthfeel Factors.

Flavor leaders have a mouthfeel that is compatible with consumers' expectations. Many drug actives and excipients can cause trigeminal effects such as tongue sting or throat burn that may be unacceptable to patients and consumers. For example, a slight amount of mouth irritation would be acceptable in a citrus flavored formulation ("citrus rind mouth irritation") but would be totally out-of-context in a bubblegum flavored formulation. Unexpected or stronger than expected mouthfeel factors can have an adverse effect on patient acceptability.

Examples of excipients that produce trigeminal effects include:
1. Methyl and propyl paraben (common preservatives in many oral pharmaceuticals) produce a tongue sting and numbing that can be unacceptable above a certain level.
2. Benzyl alcohol (solvent/preservative) produces both tongue sting and burn.

No "Off-Flavors."

Flavor leaders are notable for their consistent lack of off-flavors. An off-flavor is the appearance of an unexpected or unacceptable character note (off-note). For most oral pharmaceuticals the API is the principal source of off-notes, which can include basic tastes (e.g., bitter) and/or aromatics (e.g., sulfurous). Other sources of off-notes include excipients, e.g., paraben aromatics poor flavor systems that result in terpy, solventy, or perfumy off-notes, packaging interactions that "taint" or transfer of off-notes from the package to the product and "flavor scalping" or transfer (loss) of flavor aromatics from the product to the package.

Short (or Appropriate) Aftertaste.

The last impression i.e. the aftertaste is especially important to flavor quality. Aftertaste is caused by the persistence of one or a few character notes well after swallowing. For most products, a short, clean aftertaste is important. Products with a short, clean aftertaste encourage the consumer to take another bite or sip, and thereby to consume more of the product. For example, one of the major complaints about saccharin is its particularly long, bitter aftertaste and throat catch.

However, the goal for pharmaceuticals is patient compliance, not consumption. For many APIs, the aftertaste is most critical as many flavor systems provide adequate coverage in the early aftertaste but the beneficial effects quickly decrease, exposing the API.

As a general rule it is easier to mask a strongly bitter (or other) tasting API that "fades" quickly (steep decay curve) versus a moderately bitter API initially that lingers well into the aftertaste (flat decay curve). In any event, the challenge for the formulator is to mask the taste of the active throughout the duration of the aftertaste—be it 30 seconds or 30 minutes.

Drug Product

The study samples in Table 46 were compounded by Custom Medicine Pharmacenter, a compounding-only pharmacy in Beverly, Mass. following SIGA-approved batch records (logged formula worksheets). The Tecovirimat drug active was supplied by SIGA as bulk powder (granulated and micronized), and the excipients provided by SIGA approved suppliers.

TABLE 46

Study Formulations at 40 mg/mL Tecovirimat Concentration

| Ingredient | Manufacturer | Lot Number | Expiry | Form #1 (Strawberry mg/ml) Batch Weight (g) | Form #2 (Cherry mg/ml) Batch Weight (g) | Form #3 (API Granulated 200 mg/ml) Batch Weight (g) | Form #4 (API Micronized 200 mg/ml) Batch Weight (g) |
|---|---|---|---|---|---|---|---|
| Tecovirimat, Granulate | SIGA | 1401165 | Sep. 14, 2015 | 3.465 | 3.465 | 3.465 | — |
| Tracovirimat Monohydrate, Micronized | SIGA | 9199001 | Aug. 25, 2016 | — | — | — | 2.090 |
| Sucralose | EMD | K93441194 | Mar. 8, 2016 | 0.100 | 0.100 | — | — |
| Simethicone Granular Solid | NUSIL | 66777 | May 12, 2015 | 0.200 | 0.200 | — | — |

TABLE 46-continued

Study Formulations at 40 mg/mL Tecovirimat Concentration

| Ingredient | Manufacturer | Lot Number | Expiry | Form #1 (Strawberry mg/ml) Batch Weight (g) | Form #2 (Cherry mg/ml) Batch Weight (g) | Form #3 (API Granulated 200 mg/ml) Batch Weight (g) | Form #4 (API Micronized 200 mg/ml) Batch Weight (g) |
|---|---|---|---|---|---|---|---|
| Methocel, A4C | DOW | 2H22012N11 | Aug. 22, 2015 | 0.500 | 0.500 | — | — |
| Strawberry Flavor, 133.1529 | Bell Flavors | 521145 | Jun. 23, 2016 | 0.500 | — | — | — |
| Cherry Flavor, 23950 | Virginia Dare | T02198 | Aug. 23, 2016 | — | 0.030 | — | — |
| Lactose Monohyrdrate | DFE Pharma | 10700181 | Feb. 28, 2015 | 0.685 | 0.705 | — | — |
| Purified Water | CMP | — | Dec. 31, 2015 | 47 mL | 47 mL | 47 mL | 50 mL |
|  |  | Volume Tasted |  | 50 mL | 50 mL | 50 mL | 50 mL |

Taste Assessment Days

The four formulations shown in Table 46 were evaluated over a three-day period as necessary to ensure that the maximum daily exposure of 600 mg per day was not exceeded. The schedule was as follows:

Day 1:
Tecovirimat Formulation 3 (200 mg/5 mL)—Tasted twice
Tecovirimat Formulation 4 (200 mg/5 mL)—Tasted once
Day 2:
Tecovirimat Formulation 4 (200 mg/5 mL)—Tasted once
Tecovirimat Formulation 1 (200 mg/5 mL)—Tasted twice
Day 3:
Tecovirimat Formulation 1 (200 mg/5 mL)—Tasted once
Tecovirimat Formulation 2 (200 mg/5 mL)—Tasted twice Flavor Profile Results The panelists evaluated the samples by the procedure outlined above. The results are summarized by formulation in tabular and graphical formats below. The tabular format contains the final Flavor Profile for the sample along with interpretation of the results using the Flavor Leadership Criteria.

The challenge for many oral pharmaceuticals is to mask the critical ("undesirable") sensory characteristics of the active in the initial flavor and throughout the aftertaste.

To visualize the temporal sensory effects (aftertaste) it is useful to plot selected attribute intensities as a function of time. Thus, following each tabular summary is a graph. In each graph, the area above a slight intensity (>1) has been shaded. Negative sensory characteristics above this intensity are clearly perceptible to patients and are often found to be unacceptable.

To increase the likelihood of product acceptability the intensity of negative sensory characteristics should remain below this critical intensity throughout a product's flavor profile.

Tecovirimat—Formulation 3 (Granules)

Tecovirimat (200 mg/mL) Formulation #3 (Granule) is characterized by musty aromatic off notes, bitter basic taste and tannin/chalky mouth feels as shown in Table 47.

TABLE 47

Flavor Profile for Tecovirimat - Formulation 3 (Granules)

Flavor Profile SIGA Tecovirimat Formulation #3 200 mg/mL (Granule)

|  | Initial | 1 Min | 3 Min | 5 Min | 10 Min | 15 Min | 20 Min | 25 Min | 30 Min |
|---|---|---|---|---|---|---|---|---|---|
| Musty Aromatic | 2 | 1½ | 1 | ½ | — | — | — | — | — |
| Sour | ½ | — | — | — | — | — | — | — | — |
| Bitter | 1 | 1-1½ | 1 | ½ | ½ | ½ | 0 — | — | — |
| Chalky Mouthfeel | 1 | 1 | ½-1 | ½ | — | — | — | — | — |
| Tannin Mouthfeel | 1½ | 1½ | 1 | 1 | — | — | — | — | — |
| Drying Mouthfeel | ½ | 1 | 1½ | 1½ | 1-1½ | 1-1½ | 1 | ½ | — |

Flavor Leadership Interpretation

| 1 - Aromatic Identity | 2- Amplitude | 3- Mouthfeel | 4- Off-Notes | 5-Aftertaste |
|---|---|---|---|---|
| Not applicable for unflavored products | Not applicable for unflavored products | Chalky, tannin and drying mouthfeels | Slight-to-moderate intensity bitterness and moderate intensity musty aromatic off-notes | Lingering bitterness, mouthfeels and aromatic off-notes |

Figure 12:
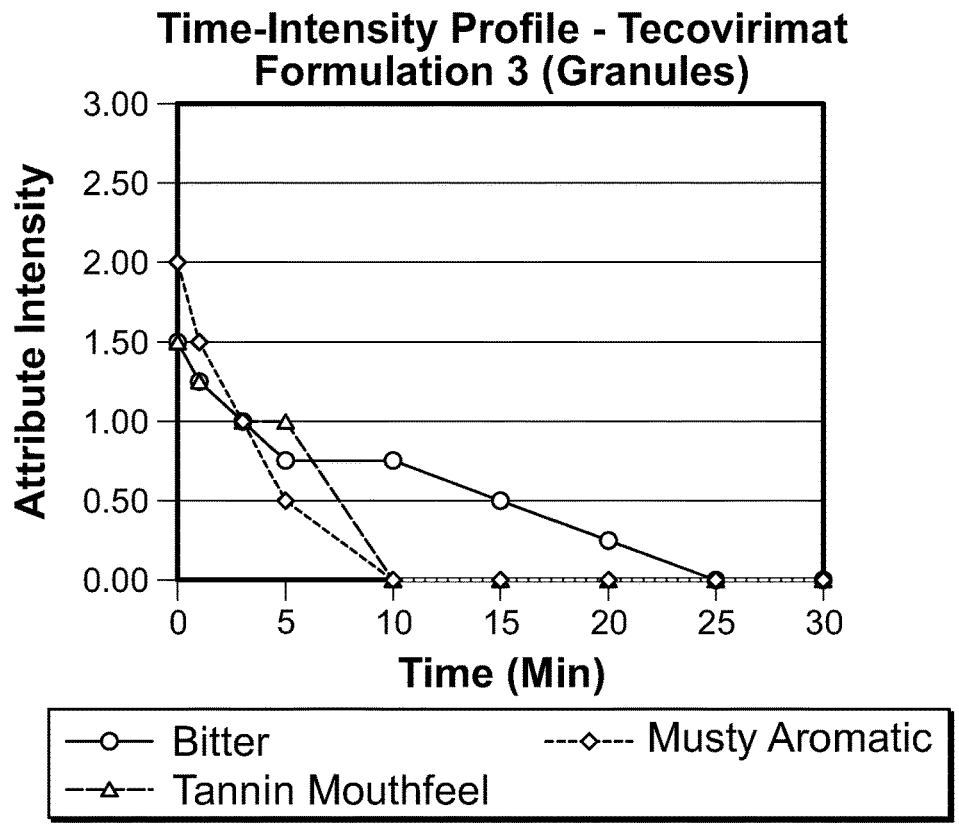
Figure 13:
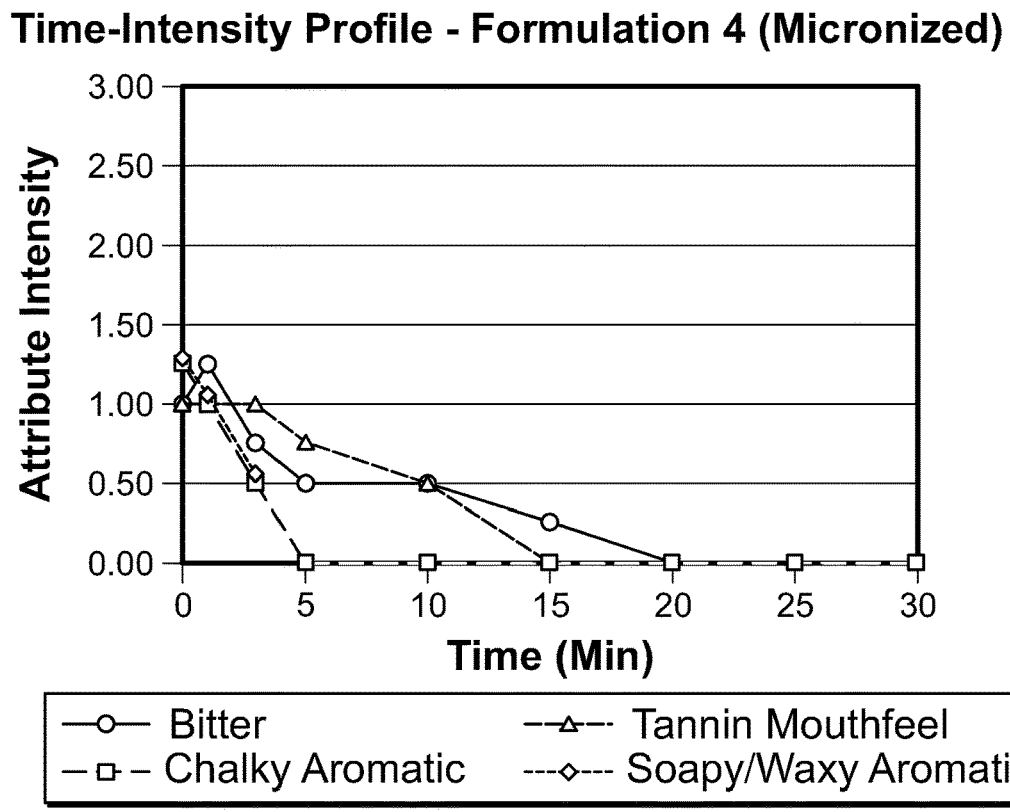

The musty aromatic off-notes, bitterness and tannin mouthfeel of the Tecovirimat granules (Formulation #3) lingered at patient-perceptible levels (1) for about 3 minutes in the Aftertaste, see FIG. 12.

Tecovirimat—Formulation 4 (Micronized)

Tecovirimat (200 mg/mL) Formulation #4 (micronized API) is characterized by aromatic offnotes (chalky, soapy/waxy), bitter basic taste and tannin/chalky mouthfeels, though generally lower in intensity than the API granules as shown in Table 48.

TABLE 48

Flavor Profile for Tecovirimat - Formulation 4 (Micronized)

Flavor Profile SIGA Tecovirimat Formulation #4 200

TABLE 50

Tecovirimat - Formulation 2 (Cherry)

Flavor Profile SIGA Tecovirimat Formulation #2 200 mg/mL (Cherry)

| | Initial | 1 Min | 3 Min | 5 Min | 10 Min | 15 Min | 20 Min | 25 Min | 30 Min |
|---|---|---|---|---|---|---|---|---|---|
| Amplitude | ½-1 | | | | | | | | |
| Sweet | 1½ | 1-1½ | ½-1 | ½ | 0-½ | 0-½ | — | — | — |
| Sour | ½ | 1-1½ | — | — | — | — | — | — | — |
| Strawberry Aromatics(Fresh and Cream) | 1½ | 1 | ½ | — | — | — | — | — | — |
| Chalky/Musty Aromatic | 1½ | 1 | ½ | — | — | — | — | — | — |
| Bitter | 1 | 1 | ½-1 | ½ | ½ | — | — | — | — |
| Chalky Mouthfeel | 1 | 1-½ | 1 | ½ | — | — | — | — | — |
| Tannin Mouthfeel | 1 | 1-½ | 1 | ½ | ½ | 0-½ | — | — | — |
| Drying Mouthfeel | — | 1 | 1-1½ | 1-1½ | 1 | 1 | 1 | ½ | — |
| Synthetic Sweetener Sensation (SSS) | — | 1 | ½-1 | ½ | ½ | — | — | — | — |

| Flavor Leadership Interpretation | | | | |
|---|---|---|---|---|
| 1 - Aromatic Identity | 2- Amplitude | 3- Mouthfeel | 4- Off-Notes | 5-Aftertaste |
| Slight-to-moderate intensity strawberry flavoring aromatics | A low level of balance and fullness | Chalky, tannin, drying and SSS mouthfeels | Slight intensity bitterness and slight-to-moderate intensity chalky/musty aromatic off-notes | Lingering basic tastes, aromatic off-notes and mouthfeels |

Figure 14:
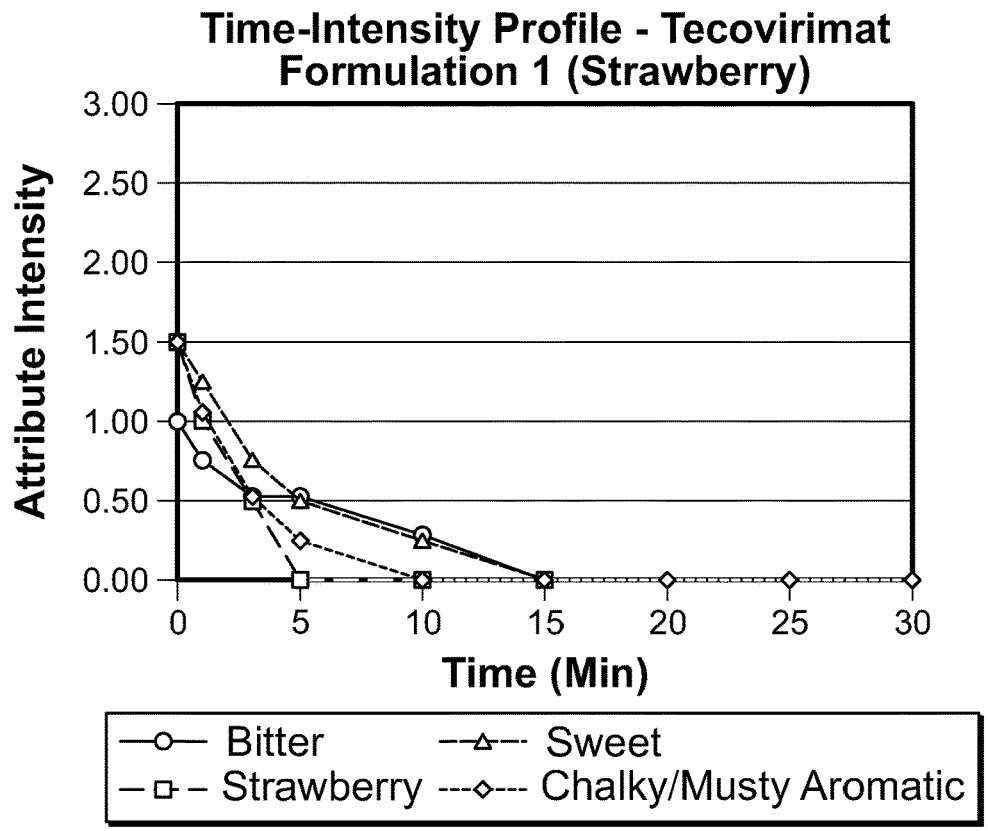
Figure 15:
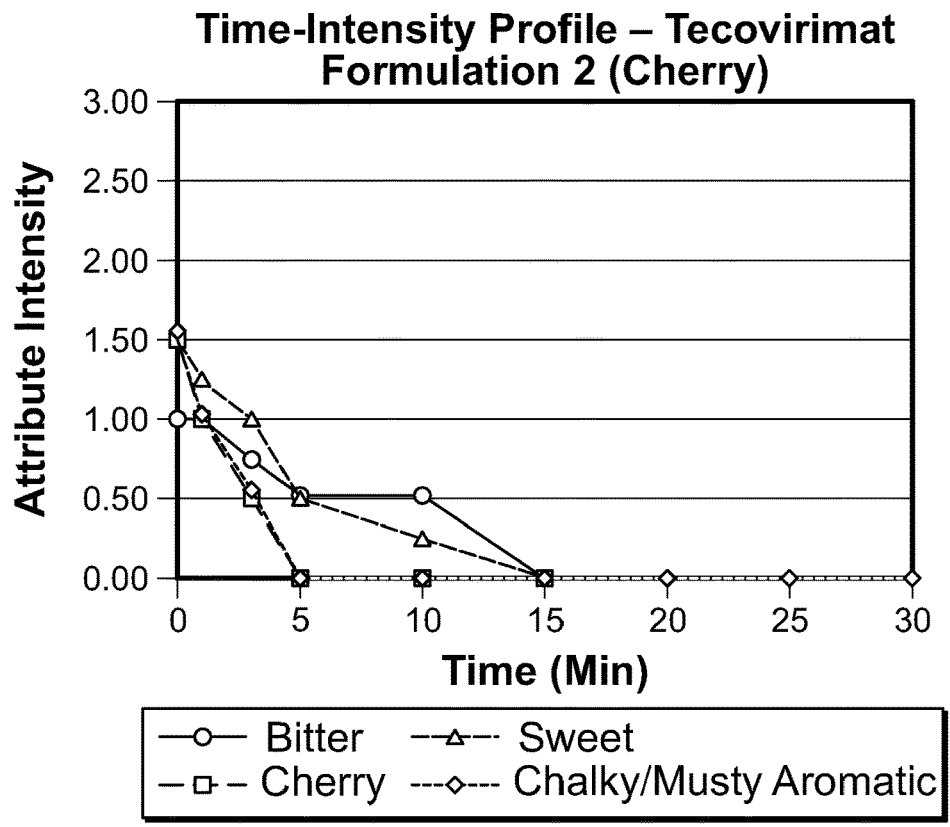

The flavor system (flavoring aromatics and sweet basic taste) of Formulation #2 (Cherry) provides reasonable coverage of the bitter basic taste and chalky/musty aromatics as shown in FIG. 14.

The results show that he unsweetened/unflavored Tecovirimat formulations are characterized by aromatic offnotes, (musty, chalky, soapy/waxy), bitter basic taste and tannin/chalky mouthfeels. However, overall, these attributes are lower in intensity in the micronized API compared to the granules.

The negative attributes of the micronized API are near the perception threshold for most patients (i.e., may not be patient-perceptible).

The two sweetened/flavored Tecovirimat suspensions are somewhat low in overall flavor quality and both flavored suspensions are somewhat low in initial flavor quality as measured by Amplitude (Target=1.) due to their aromatic off-notes (chalky/musty), bitter basic taste and mouthfeels (tannin/chalky).

Both flavored suspensions are somewhat low in flavor and sweetness impact (intensity). However the strawberry-flavored suspension is slightly more blended and full (i.e., higher in Amplitude) than cherry-flavored suspension, which was somewhat "solventy" (benzaldehyde-like) in character and both flavored suspensions provide a reasonable coverage of the bitter basic taste and chalky/musty aromatics, though the flavoring aromatics fade quickly.

Thus it can be seen that Tecovirimat is relatively "bland" in flavor (basic tastes, aromatics, mouthfeel and texture), with the micronized API having a lower flavor than the API granules and the sweetened/flavored formulations are somewhat low in flavor quality (strawberry higher than cherry), primarily due to low impact (intensity) and duration of the flavoring aromatics and to a lesser extent the underlying sweet basic taste.

While the present invention has been described with reference to the specific embodiments thereof, it should be understood by those skilled in the art that various changes may be made, and equivalents may be substituted, without departing from the true spirit and scope of the invention. In addition, many modifications may be made to adapt a particular situation, material, composition of matter, process, process step or steps, to the objective, spirit and scope of the present invention. All such modifications are intended to be within the scope of the invention.

REFERENCES

1. Fenner et al., The epidemiology of smallpox. In: Smallpox and its eradication. Switzerland: World Health Organization; 1988)
2. Bray et al., Antiviral Research 58: 101-114 (2003).
3. Quenelle et al. 2007. Efficacy of delayed treatment with ST-246 given orally against systemic orthopoxvirus infections in mice. Antimicrobial Agents and Chemotherapy February; 51(2):689-95
4. Smee et al. (2002) Antimicrob. Agents Chemother. 46:1329-1335)
5. Vora et al., 2008, Severe eczema vaccinatum in a household contact of a smallpox vaccine. Clinical Infectious Disease 15; 46(10):1555-61).

The invention claimed is:

1. A dry suspension comprising polymorph Form I of 4-trifluoromethyl-N-(3,3a,4,4a,5,5a,6,6a-octahydro-1,3-dioxo-4,6-ethenocycloprop[f]isoindol-2-(1H)-yl)-benzamide (Tecovirimat (ST-246)) and simethicone.

2. A dry suspension according to claim 1 further comprising at least one suspending agent.

3. A dry suspension according to claim 2 wherein the suspending agent is methylcellulose or hydroxypropyl cellulose.

4. A dry suspension according to claim 3 wherein the methylcellulose is methylcellulose 400 Cps; or wherein the methylcellulose is 15 Cps.

5. A dry suspension according to claim 2 comprising methylcellulose and hydroxypropyl cellulose.

6. A dry suspension according to claim 1 further comprising one or more of a lubricant, an excipient, an anti-foaming agent, a sweetener, and/or a flavoring.

7. A dry suspension according to claim 6 wherein the lubricant is magnesium stearate and/or wherein the excipient is lactose monohydrate.

8. A dry suspension according to claim 1 wherein the ST-246 is micronized; or wherein the ST-246 is granulated.

9. A dry suspension according to claim 1 wherein the simethicone is granular form; or wherein the simethicone is in liquid form and adsorbed on lactose monohydrate.

10. A dry suspension according to claim 1 comprising one or more of 10 to 70 wt % of ST-246; 0.2 to 6.0 wt % simethicone; 1 to 5 wt % methylcellulose; 1.0 to 30 wt % hydroxypropylcellulose; 0.1 to 1.0 wt % of lubricant; 10 to 20 wt % of excipient; 1.0 to 3.0 wt % of sweetener; and/or 0.1 to 1.0 wt % of flavoring.

11. A dry suspension according to claim 1 wherein the particle size of ST-246 is 0.5 to 10 μm.

12. An aqueous pharmaceutical suspension formulation comprising a dry suspension according to claim 1 and water; wherein the aqueous pharmaceutical suspension formulation optionally further comprises a pharmaceutically acceptable ingredient.

13. A formulation according to claim 12 wherein the pharmaceutically acceptable ingredient is selected from the group consisting of carrier, excipient, diluent, additive, filler, lubricant and binder.

14. A formulation according to claim 12 having a pH between 4 and 7.

15. A method of treating orthopoxvirus infections and/or eczema vaccinatum comprising oral administration to a subject in need thereof a formulation according to claim 12.

16. The method of claim 15, wherein the subject is administered 400 mg to 2000 mg daily of ST-246.

17. A process of making the dry suspension according to claim 1 comprising mixing ST-246 with simethicone and optionally at least one suspending agent, at least one lubricant, at least one excipient, at least one further anti-foaming agent, at least one sweetener and/or at least one flavoring.

18. A process according to claim 17 wherein the mixing is carried out using geometric mixing.

19. A method of making the formulation according to claim 12 comprising dispersing the dry suspension in water; wherein the water optionally contains a suspending agent.

* * * * *